(12) United States Patent
Kovarik et al.

(10) Patent No.: US 9,750,802 B2
(45) Date of Patent: *Sep. 5, 2017

(54) METHOD AND SYSTEM FOR TARGETING THE MICROBIOME TO PROMOTE HEALTH AND TREAT ALLERGIC AND INFLAMMATORY DISEASES

(71) Applicants: Katherine Rose Kovarik, Englewood, CO (US); Joseph E. Kovarik, Englewood, CO (US)

(72) Inventors: Katherine Rose Kovarik, Englewood, CO (US); Joseph E. Kovarik, Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/270,034

(22) Filed: Sep. 20, 2016

(65) Prior Publication Data

US 2017/0021011 A1   Jan. 26, 2017

Related U.S. Application Data

(63) Continuation of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 15/270,034, which is a continuation-in-part of application No. 15/228,454, filed on Aug. 4, 2016, now Pat. No. 9,585,920.

(60) Provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013.

(51) Int. Cl.

| A61K 35/74 | (2015.01) |
| A61K 39/35 | (2006.01) |
| A61K 35/741 | (2015.01) |
| A61K 35/742 | (2015.01) |
| A61K 35/747 | (2015.01) |
| A61K 9/00 | (2006.01) |
| A61K 45/06 | (2006.01) |
| A61K 39/395 | (2006.01) |
| A61K 35/745 | (2015.01) |
| C07K 16/00 | (2006.01) |
| A61K 39/39 | (2006.01) |
| A61K 39/00 | (2006.01) |

(52) U.S. Cl.
CPC .............. *A61K 39/35* (2013.01); *A61K 9/007* (2013.01); *A61K 9/0034* (2013.01); *A61K 9/0043* (2013.01); *A61K 35/74* (2013.01); *A61K 35/741* (2013.01); *A61K 35/742* (2013.01); *A61K 35/745* (2013.01); *A61K 35/747* (2013.01); *A61K 39/0008* (2013.01); *A61K 39/39* (2013.01); *A61K 39/395* (2013.01); *A61K 45/06* (2013.01); *C07K 16/00* (2013.01); *A61K 2039/505* (2013.01); *A61K 2039/541* (2013.01); *A61K 2039/544* (2013.01); *A61K 2039/55* (2013.01); *A61K 2039/55583* (2013.01); *A61K 2039/577* (2013.01); *A61K 2039/58* (2013.01); *A61K 2039/70* (2013.01)

(58) Field of Classification Search
None
See application file for complete search history.

(56) References Cited

U.S. PATENT DOCUMENTS

| 3,178,341 A | 4/1965 | Hamill et al. |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,277,877 A | 1/1994 | Jeffrey et al. |
| 5,614,501 A | 3/1997 | Richards |
| 6,287,610 B1 | 9/2001 | Bowling et al. |
| 6,569,474 B2 | 5/2003 | Clayton et al. |
| 6,722,577 B2 | 4/2004 | Dobyns, III |
| 7,353,194 B1 | 4/2008 | Kerker et al. |
| 7,540,432 B2 | 6/2009 | Majerowski et al. |
| 7,862,808 B2 | 1/2011 | Isolauri et al. |
| 8,034,606 B2 | 10/2011 | Park et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,420,074 B2 | 4/2013 | Rehberger et al. |

(Continued)

FOREIGN PATENT DOCUMENTS

| WO | WO 2011/020780 | 2/2011 |
| WO | WO 2013/026000 | 2/2013 |

(Continued)

OTHER PUBLICATIONS

U.S. Appl. No. 15/200,210, filed Jul. 1, 2016, Barreca et al.

(Continued)

*Primary Examiner* — Brian J Gangle
(74) *Attorney, Agent, or Firm* — Sheridan Ross P.C.

(57) ABSTRACT

A method and system for targeting the microbiome to promote health involves exposing an expectant mother to a mixture of farm derived manure-containing soil to reduce the chances her baby will suffer allergies and autoimmune diseases. City dwelling expectant mothers are exposed to immunologic agents and allergens in a fashion (e.g., via exposure to farm animal manure-containing soils) that charges their immune system and that of their fetus(es) so that their babies, once born, are provided with immunity against a variety of autoimmune diseases, including allergies commonly and increasingly experienced in modern urban environments.

26 Claims, 8 Drawing Sheets

(56) References Cited

U.S. PATENT DOCUMENTS

| | | |
|---|---|---|
| 8,454,729 B2 | 6/2013 | Mittelmark et al. |
| 8,496,914 B2 | 7/2013 | Bonfiglio |
| 8,585,588 B2 | 11/2013 | Kovarik et al. |
| 8,591,412 B2 | 11/2013 | Kovarik et al. |
| 8,701,671 B2 | 4/2014 | Kovarik |
| 9,010,340 B2 | 4/2015 | Kovarik et al. |
| 9,011,834 B1 | 4/2015 | McKenzie et al. |
| 9,044,420 B2 | 6/2015 | Dubensky, Jr. et al. |
| 9,387,168 B2 | 7/2016 | Barreca et al. |
| 9,408,880 B2 | 8/2016 | Kovarik et al. |
| 9,457,077 B2 | 10/2016 | Kovarik et al. |
| 2003/0206995 A1 | 11/2003 | Bowling et al. |
| 2004/0053352 A1 | 3/2004 | Ouyang et al. |
| 2004/0115223 A1 | 6/2004 | Follansbee |
| 2004/0142463 A1 | 7/2004 | Walker et al. |
| 2004/0166501 A1 | 8/2004 | Azimzai et al. |
| 2005/0118655 A1 | 6/2005 | Weinstock et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0123448 A1 | 5/2007 | Kaplan et al. |
| 2007/0207955 A1 | 9/2007 | Tanihara et al. |
| 2007/0231923 A1 | 10/2007 | Cumberland et al. |
| 2008/0112983 A1 | 5/2008 | Bufe et al. |
| 2008/0305089 A1 | 12/2008 | Bufe et al. |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2012/0029832 A1 | 2/2012 | Dodgson |
| 2012/0039806 A1 | 2/2012 | Lahoud et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0225440 A1 | 8/2013 | Friedman et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0238411 A1 | 8/2014 | Kovarik |
| 2014/0255351 A1 | 9/2014 | Berstad et al. |
| 2014/0349405 A1 | 11/2014 | Sontheimer et al. |
| 2014/0363441 A1 | 12/2014 | Grandea, III et al. |
| 2014/0377278 A1 | 12/2014 | Elinav et al. |
| 2015/0004130 A1 | 1/2015 | Faber et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0132263 A1 | 5/2015 | Liu et al. |
| 2015/0147371 A1 | 5/2015 | Kovarik et al. |
| 2015/0190435 A1 | 7/2015 | Henn et al. |
| 2015/0252358 A1 | 9/2015 | Maeder et al. |
| 2015/0290026 A1 | 10/2015 | Kovarik |
| 2016/0000754 A1 | 1/2016 | Stamets |
| 2016/0000841 A1 | 1/2016 | Yamamoto et al. |
| 2016/0069921 A1 | 3/2016 | Holmes et al. |
| 2016/0095316 A1 | 4/2016 | Goodman et al. |
| 2016/0151428 A1 | 6/2016 | Bryan |
| 2016/0158294 A1 | 6/2016 | von Maltzahn et al. |
| 2016/0175327 A1 | 6/2016 | Adams et al. |
| 2016/0199424 A1 | 7/2016 | Berry et al. |
| 2016/0206666 A1 | 7/2016 | Falb et al. |
| 2016/0206668 A1 | 7/2016 | Kort et al. |
| 2016/0213702 A1 | 7/2016 | von Maltzahn et al. |

FOREIGN PATENT DOCUMENTS

| | | |
|---|---|---|
| WO | WO 2013/107750 | 7/2013 |
| WO | WO 2014/103488 | 7/2014 |
| WO | WO 2015/069682 | 5/2015 |

OTHER PUBLICATIONS

U.S. Appl. No. 15/228,454, filed Aug. 4, 2016, Kovarik et al.

Auerbach et al., "Angiogenesis assays: Problems and pitfalls," Cancer and Metastasis Reviews, 2000, vol. 19, pp. 167-172.

Gura, "Systems for Identifying New Drugs are Often Faulty," Science, 1997, vol. 278(5340), pp. 1041-1042, 5 pages.

Jain, "Barriers to Drug Delivery in Solid Tumors," Scientific American, 1994, pp. 58-65.

Kilkkinen et al., "Use of antimicrobials and risk of type 1 diabetes in population-based mother-child cohort," Diabetologia, 2006, vol. 49, pp. 66-70.

Kimoto et al., "New Lactococcus Strain with Immunomodulatory Activity: Enhancement of Th1-Type Immune Response," Microbiol. Immunol., 2004, vol. 48(2), pp. 75-82.

Norton et al., "The immune response to Lactococcus lactis: implications for its use as a vaccine delivery vehicle," FEMS Microbiology Letters, 1994, vol. 120(3), pp. 249-256, abstract only, 2 page.

Repa et al., "Mucosal co-application of lactic acid bacteria and allergen induces counter-regulatory immune responses in a murine model of birch pollen allergy," Vaccine, 2003, vol. 22(1), pp. 87-95, abstract only, 1 page.

Sporn et al., "Chemoprevention of Cancer," Carcinogenesis, 2000, vol. 21(3), pp. 525-530.

Zhao et al., Microbiome-generated amyloid and potential impact on amyloidogenesis in Alzheimer's disease (AD) Journal of Nature and Science, 2015, vol. 1(7) pp. 1-5.

METHOD AND SYSTEM FOR TARGETING THE MICROBIOME TO PROMOTE HEALTH AND TREAT ALLERGIC AND INFLAMMATORY DISEASES

RELATED APPLICATIONS

The present application is a continuation of U.S. patent application Ser. No. 14/954,074, filed Nov. 30, 2015 (now U.S. Pat. No. 9,457,077, issuing Oct. 4, 2016), which is a continuation-in-part of U.S. patent application Ser. No. 14/574,517, filed Dec. 18, 2014 (now U.S. Pat. No. 9,408,880, issued Apr. 9, 2016), which claims priority from U.S. Provisional Patent Application Ser. No. 62/072,476, filed on Oct. 30, 2014, U.S. Provisional Patent Application Ser. No. 62/053,926, filed Sep. 3, 2014, U.S. Provisional Patent Application. Ser. No. 62/014,855, filed Jun. 20, 2014 and U.S. Provisional Patent Application Ser. No. 61/919,297, filed on Dec. 20, 2013. The present application is also a continuation-in-part of U.S. patent application Ser. No. 15/228,454, filed Aug. 4, 2016. The entire disclosure of the prior applications are consider to be part of the discloser of the accompanying application and are hereby incorporated by reference.

FIELD OF THE INVENTION

The present invention is directed to a method and system to expose expectant mothers to a mixture of farm derived manure-containing soil to reduce the chances that their offspring will suffer autoimmune diseases, including allergies. Other embodiments are directed to the prevention of Alzheimer's disease by modification of an individual's oral microbiome.

BACKGROUND OF THE INVENTION

A person is said to have an allergy when their immune system overreacts to the presence of a substance (an allergen) that is not normally considered to be of danger to the body. When a person becomes hypersensitive to one or more allergens, the body assumes it is being invaded and calls up the defense forces to neutralize the offending substance. Allergy is defined as an "abnormal hypersensitivity to a substance which is normally tolerated and generally considered harmless." Unfortunately, the release of histamine during this response produces unwelcome symptoms such as sneezing, runny or stuffed nose, itchy eyes, breathing difficulties, and, in extreme cases, anaphylactic shock and death.

Autoimmune disease affects an estimated 50 million people at an annual cost of more than $100 billion and the suffering and monetary costs are sure to grow. The prevalence of allergic disease and asthma increased between two- and threefold in the late 20th century, a mysterious trend often called the "allergy epidemic." It is believed that highly hygienic environments, especially in infancy, play an important role in the skyrocketing occurrence of asthma, allergies and autoimmune disease.

One medically accepted treatment for allergies is immunotherapy. Immunotherapy involves the repeated injection of allergen extracts to desensitize a patient to the allergen. Traditional immunotherapy is time consuming, usually involving years of treatment, and often fails to achieve its goal of desensitizing the patient to the allergen. Furthermore, it is not the recommended treatment for food allergies, such as peanut allergies, due to the risk of anaphylaxis, a systemic and potentially lethal.

It has been observed that children born to mothers who work with livestock while pregnant, and who lug their newborns along during chores, seem the most invulnerable to allergic disease later. It has also been observed that there are differences in the placentas of children who later develop allergies such that a critical subset of white blood cells—called regulatory T-cells—seems relatively scarce at birth. It is suspected that a healthy population of these and other "suppressor" cells is important in preventing allergies and asthma. Evidence exists that European farming children are born with a comparative surfeit of these cells. Other findings report that farming newborns have more regulatory T-cells in cord blood than babies of nonfarmers. Moreover, it has been observed that such suppressive ability increases with the number of different types of animals the mother tended while pregnant.

Confusingly, however, it has also been observed that occasional visits to the farm may exacerbate allergic propensities, thus those who believed that simply taking a family outing to a farm would somehow ameliorate allergies has not proven to be effective.

Isolation of the curative agents at issue for allergies has thus far eluded top scientists and researchers. In the meantime, expectant mothers are desperate to do something, but unsure of what to do in a culture that touts a "cleanliness is good" ethos instilled in the developed world—but at the same time stressing the protection of mothers and children from terrible diseases caused by the filthy habitats that exist in underdeveloped regions of the globe.

There is increasing evidence that many aspects of health and disease are determined not only during infancy, but also during pregnancy. This is especially true with allergic disease, where immune responses at birth implicate intrauterine exposure as a primary sensitization event. It has been shown that the human fetus develops IgE-producing B cells early in gestation and is capable of producing IgE antibodies in response to appropriate antigenic stimuli in a manner analogous to the well-recognized IgM responses that are observed in various prenatal infections. Others have documented the various empirical evidence that exposures to various agents has a profound impact on a human's development of a healthy immune system, free of allergies and autoimmune diseases, collectively sometimes referred to as the "hygiene hypothesis." See e.g. Velasquez-Manoff, "An Epidemic of Absence."

The largest microbial community in the human body resides in the gut and comprises somewhere between 300 and 1000 different microbial species. The human body, consisting of about 100 trillion cells, carries about ten times as many microorganisms in the intestines. The gut microbiome contains at least two orders of magnitude more genes than are found in the *Homo sapiens* genome.

The laudable goal of discovering the secret in the immunity benefits of living on a farm has occupied countless hours of skilled and talented individuals and frustrated those experts in the field whose lives are dedicated to discovering the cause of the acquired immunity, and to then bottle up the cure and provide it to the increasing masses of urban dwellers. This objective has been as sought after as it has proven elusive. In the meantime, the rise in allergies increases without abatement and children are daily diagnosed with life threatening allergic conditions that defy explanation. This presents, therefore, a classic case of a long felt but unsolved need, made all the more compellingly frustrating by having the apparent effective agent that confers immunity—present just miles away from city centers: on the farm.

The present inventors submit that in the interim period before the precise agents that confer immunity are discovered and isolated, it is important for expectant mothers to be comfortable with being provided with an effective composition without knowing precisely what agent or agents is responsible for such benefit. It may take decades for such determinants to be "discovered" and isolated. But the lives and tremendous emotional, financial and human capital expended—as well as lives lost—is too precious to simply await the ultimate elucidation of the cure—or at least effective refined treatment of a select agent that confers the desired immunologic factors to a person, and especially to a fetus.

There is therefore a need for a treatment that can be made available to city dweller expectant mothers so that their unborn babies have a significant opportunity to develop immunity to life threatening allergies and other autoimmune diseases in later life. And in addition to food allergies, there is a need to understand and address other autoimmune diseases including type 1 diabetes, Crohn's disease, multiple sclerosis, Alzheimer's, asthma, autism, inflammatory arthritis, lupus, lupus erythermatosis, juvenile rheumatoid arthritis, immune cancers, inflammatory bowel disease, ulcerative colitis, allergic rhinitis, celiac disease, obesity, and oesophageal reflux. The present inventors disclose treatments that are fashioned to avoid and prevent, but at least to reduce, the occurrence of devastating diseases that can be traced back to a particular point in a person's developing immune system—where the absence of particular agents at such a critical time period can be seen as responsible for a failure to develop a better, more disease protective immune system. Such a treatment would preferably be relatively inexpensive, as expectant mothers are often young and without significant resources. It should be available in a fashion that they can be exposed to the immunologic agents in a fashion that does not depend upon their dutiful regimen of taking some medication or treatment—and thus, a system and method that exposes them to the treatment without a daily calendar of duties would be preferred. It would preferably be simple, economical and effective without interfering significantly with the expectant mothers otherwise busy and—by the nature of pregnancy—worrisome, hormonal and often challenging time period in life, with job and family and health issues seemingly changing on a daily basis as their belly grows.

SUMMARY OF THE INVENTION

The prevalence of allergic disease has increased dramatically in the developed world during the second half of the 20th century, and it has been suggested that this increase is in part due to reductions in early microbial exposure. Some evidence for this hypothesis exists in that some propose that exposure to antibiotics early in life increases the risk of developing allergic disease. The present inventors contend that because it is believed that the immune system develops in utero, factors that modify microbial exposure at this time may have a long-term impact on the risk of developing allergic disease.

There is a need for treatments and preventive methods for patients with allergies to allergens that elicit serious allergic responses including anaphylaxis. One object of the present invention resides in providing means that allow treatment of allergy in an efficient, easy and cost effective manner preferably without requiring a physician and without bringing about the negative associations linked with such treatments.

It is, therefore, an object of the present invention to reduce, minimize, or prevent allergies caused by environmental allergens. Asthma and allergies are common in the developed world and rare in the undeveloped world. It is an aspect of the present invention to provide a method of reducing or preventing undesirable allergic reactions and anaphylactic allergic reactions to allergens via exposure of expectant mothers to a selected composition containing allergens such that the fetus, and thus the later born child, will avoid having allergies.

While it is true that particular identified active agents responsible for conferring protection to an unborn child via exposure of such agents to a pregnant mother have yet to be isolated, one aspect of the present invention is directed to inclusion of such as yet unidentified agents in a system and method so as to achieve the desired result of conferring immunity to an unborn child. While it is acknowledged that further work is required to elucidate the particular agents, combinations, best delivery aspects, etc. responsible for conferring immunity, the inevitable reality is that literally thousands of people will acquire allergies and potentially life threatening allergic reactions during the time it will take to identify such agents with precision, and thus, if one were to await such a refined understanding of the mechanisms of actions at issue, many people will suffer and die. Thus, while admittedly a crude embodiment of what in the future will be established as one of the most effective, natural ways to confer immunity to the unborn, the present invention is set forth so as to reduce or prevent the multitude of individuals who would otherwise suffer from the effects of allergic reactions. The prior poorly understood suspicion that something in certain farm environments is effective at conferring immunity has seemingly prevented those in the field from providing life saving systems and methods to achieve conference of such immunity, as it was apparently believed that until such agents could be properly identified, then there was allegedly nothing that could be done in the meantime to provide treatments to the unborn. Thus, one aspect of the present invention relates to the fact that such refined elucidation of the causative agents is not required to achieve desired results. Instead, via an understanding of the source of immunity conferring agents and the provision of the same at the right time and frequency, certain embodiments of the present invention provide a method and system to obtain the desired result: providing immunity to the unborn via exposure of pregnant women to such immunity conferring agents.

In certain embodiments, certain microbes are obtained in a form such that they are placed in an environment effective to stimulate a mother's immune system during pregnancy, preventing allergic disease in her unborn children. In particular, in various embodiments, bovine manure, preferably obtained from farmers who use little if any antibiotics with respect to such cattle (as such can be found on certain Amish farms), is provided in a form and at a time such that expectant mothers achieve the desired immunity for their unborn children. By obtaining samples of material from such farms and bringing such materials to the urban residence of pregnant mothers, the mothers are exposed to the allergens and thus, immunity of the same is conferred to the unborn. The various components and agents of the material preferably include innocuous cowshed microbes, plant material, fungi and agents found in raw milk. More preferably, material is collected and provided in an environment of an urban-residing pregnant mother that has manure derived from one, and preferably more than one of cows, horses, pigs and chickens, and goats.

There has been an epidemic of both autoimmune diseases (in which the immune response is dominated by type 1 helper T [Th1] cells, (such as type 1 diabetes, Crohn's disease, and multiple sclerosis) and allergic diseases in which the immune response is dominated by type 2 helper T [Th2] cells (such as asthma, allergic rhinitis, and atopic dermatitis). The occurrence of these diseases is higher in more affluent, Western, industrialized countries. Although the so-called hygiene hypothesis theory dates back to at least the mid-1960s in relation to Th1-mediated diseases, decades later it was first proposed that this theory might also explain the increase in Th2-mediated diseases. Improved hygienic conditions in Western or developed countries results in less infection-driven or microbial pressure during early but critical time periods in early childhood. This change in pressure, in turn, results in an important failure to maintain an optimal balance between the two opposing T-helper cell responses when cytokine profiles are examined—the Th1 and Th2 responses. Th1 responses are dominated by interferon (IFN)-gamma and interleukin (IL)-12 production, whereas Th2 responses are primarily associated with IL-4, IL-5, IL-13 (and IL-10) production. In association with reductions or altered exposures to infectious agents or their components, Th2 immunity, predominating from birth, dominates through critical childhood periods, resulting in the higher incidence of atopy and asthma. Intestinal microflora is believed to exert a continuous stimulation of the immune system, resulting in immune polarization—the cleaner the intestine or the nature of colonization of the intestine, the more Th2-driven is the immune response. Lower prevalences of allergic diseases are described in rural areas of Africa and China although similar urban-rural differences have not been seen in Europe or North America. The present inventors believe that a reason for such confounding findings involves the prevalence of antibiotic use in the later territories as compared to the former.

The potential of Th1-inducers like endotoxin to reduce asthma and allergy is consistent with the hygiene hypothesis, but endotoxin exposure is not an accepted general treatment as it is also thought to play a central role in determining the severity in asthma. Endotoxin is a lipopolysaccharide that forms the outer layer of the cell membrane of all gram-negative bacteria. Endotoxin levels vary widely but tend to be highest in environments where there are farm animals such as cows, horses, and pigs, because the fecal flora of larger mammals is a major source of endotoxin.

The present inventors submit that the long felt but unsolved autoimmune problems presently experienced in urban environments should be viewed in the context of Occam's Razor: the simplest explanation is usually correct. Here, the present inventors believe that the simple explanation of the mystery as to why there is an epidemic in various diseases in the last 50 years, most now suspected of being autoimmune-based, is found in the root cause of the legendary resistance the Amish have demonstrated to so many of these modern plagues. The Amish seem largely protected—literally immune to—such diseases as: Alzheimer's, allergies, asthma, autism, inflammatory arthritis, lupus, lupus erythermatosis, juvenile rheumatoid arthritis, immune cancers, juvenile diabetes, inflammatory bowel disease, Crohn's disease, ulcerative colitis, multiple sclerosis, allergic rhinitis, celiac disease, obesity, oesophageal reflux, and allergies to specific foods.

While others have speculated as to why the Amish have been spared the fates of those outside its insular community, the present inventors have surmised the underlying rationale for such seemingly divine benevolence. It is not due to some unique genetic trait possessed by the Amish. It is not because the Amish have an aversion to vaccines that may have a mercury component. The "something" that is protecting the Amish from various diseases lies in their exposure to allergens that the majority of mankind has—until recently—experienced at birth and during their first year of life. But the last 50 years has seen the rise of antibiotic use—not just with humans, but in the raising of livestock. The use of antibiotics for farm animals, especially bovine animals, presents a significant shift in the resident populations of bacteria, and especially lactobacilli, that have been regular features of a human's environment. But this general concept, sometimes referred to as the "hygiene hypothesis"—while it has its adherents, also has its detractors, as the numerous attempts to expose individuals to farm environments has failed to result in the immune protection sought to be achieved. Confoundingly, however, the Amish continue to seem to possess that "something" that protects the overall health of their insular community. Others have focused on organic mercury compounds found in multi-dose vaccines, which the Amish do not permit, but whose use fits nicely with the 50 year rise of various diseases. Others have speculated that the protective "something" of the Amish lies within their exposures to raw milk, lots of siblings and farm animals, and/or their particular genetic heritage. But such correlations have proven to be specious.

The Amish have very little allergy—among children ages 6 to 12 years, the percentage showing evidence of allergic sensitization is a mere 7.2 percent, far lower than children in Switzerland who live on farms (25.2 percent), and Swiss non-farm children (44.2 percent). Another example is that the Amish do not seem to suffer autism. In northeastern Ohio, where the nation's largest Amish community resides, the incidence of autism is 1 in 10,000—or even lower. The present inventors submit that the increase of each of these autoimmune diseases is partially explained by the difference in antibiotic use for livestock on such farms in such territories. But that is not the only factor involved. Developmental biology plays a central role in the protection enjoyed by the Amish to allergies and other autoimmune diseases. Timing of exposure of a newborn to certain antigens is believed to be critical in establishing a newborn's immune system at the time of birth and for the baby's first year of life.

The prevalent use of antibiotics over the past 50 years is believed to be more than coincidental to the rise in such autoimmune diseases. Some antibacterials are known to be endocrine disrupters—hampering natural growth and development, of which our immune system is part. The use of such compounds has increased dramatically over the last half century. Agriculture in the US began spraying chemical antibiotics and various chemical germicidals in abundance in the last 50 years, with such antibiotics covering much of our food and being fed to the animals we eat as a matter of course. While direct blood exposure to various microbes is ill advised due to sepsis, there are some safe routes of natural exposure to certain allergens—achieved at appropriate times during the development of the immune system. In several embodiments of the present invention, the treatment for complex auto-immune and inflammatory medical conditions involves the strategic triggering and development of the immune system through targeted application of natural soil-based organisms at critical times in a newborn's life so as to provide the foundation for the proper development of the person's immune system.

The present invention answers the long elusive question as to why are all of these maladies rapidly rising at the same time across the developed world and spilling over into the developing world as it becomes more westernized. It is more than mere coincidence, as the odds that these ten or more modern autoimmune disease plagues have ten or more separate causes is remote. The present inventors contend that there is one underlying cause fueling all these parallel increases.

Humans have coevolved with their microbes over thousands of years, but this relationship is now being dramatically affected by shifts in the collective human microbiome resulting from changes in the environment and societal norms, and especially in the last fifty years, due to the prevalence of antibiotics in our environment. Resulting perturbations of intestinal host-microbe interactions have enhanced the spread of so-called "western" disorders.

Oesophageal reflux, which causes heartburn, was uncommon 50 years ago, but it is now common, as well as the cancer it leads to, adenocarcinoma of the oesophagus, becoming the most rapidly increasing cancer in many developed countries, especially for men.

The theory that such autoimmune diseases may be alleviated via home and personal cleanliness, thus reducing exposure to vital microbes, is flawed, as not only is the idea that homes can be made "sterile" through excessive cleanliness implausible, but whatever microbes are removed from such environments are quickly replaced with still other microbes, via dust and air from outdoors, other living things, food, etc.

What is disconcerting is that at the same time that concerns about allergies and other chronic inflammatory diseases have been increasing, so too have concerns about the spread of infectious disease, which continues to exert a heavy health toll. Preventing pandemics and reducing antibiotic resistance are global priorities and good hygiene is the recommended way to avoid infectious disease threats.

The lack of exposure by an expectant mother and to a newborn to particular infectious agents, including certain microorganisms, viruses and parasites, (e.g. lactobacilli, mycobacteria, and helminthes) leads to the suppression of the natural development of the newborn's immune system, leading to defects in the establishment of immune tolerance.

The human immune system has evolved to anticipate certain types of microbial input, making centuries of inevitable exposure to such antigens into a necessity today in order for our immune systems to properly develop.

During gestation and infancy, exposure to certain organisms builds a "database" that allows the immune system to identify and respond to harmful agents. Elimination of such organisms via the widespread use of antibiotics, while well intentioned, has resulted in the elimination of such previously commonly encountered bacteria and parasites. In their absence, expectant mothers live in an environment that is free of such organisms and thus, the newborns of such mothers are deprived of an exposure that would otherwise have triggered a more typical immune response in a similar environment 50 years ago. The nascent immune system is thus deprived of the previously common primers that lead to immune protection from the above referenced list of devastating immune diseases.

This is supported by evidence that delivery by Caesarean section may be associated with increased allergies, with the newborn infant deprived of exposure to the mother's resident bacteria in her vaginal birth canal, typically the first and perhaps most important bacterial exposure a person has during its entire life. The developing immune system must receive stimuli (from infectious agents, symbiotic bacteria, or parasites) to adequately develop regulatory T cells. Without that stimuli it becomes more susceptible to autoimmune diseases and allergic diseases, because of insufficiently repressed $T_{H}1$ and $T_{H}2$ responses, respectively.

Multiple sclerosis (MS) affects more than 350,000 people in the U.S. and 2.5 million worldwide. In the U.S., prevalence estimates vary between 5 and 119 per 100,000 and healthcare costs are estimated to be more than $10 billion annually in the U.S. alone. It is the most common neurological disease in young adults, with the risk of subsequent chronic functional impairment and disability after 10-15% of disease duration. The disease is characterized initially in 80-90% of patients by recurrent neurological events (relapses) that are attributable to multifocal lesions within the CNS. Further disease courses vary from benign to classical relapsing-remitting (RR), primary (PP) and secondary (SP) chronic progressive or rare fulminant disease course. MS is considered to be of autoimmune origin and is characterized neuropathologically by variable extents of focal inflammation, demyelination, axonal damage, gliotic scarring and atrophy, but also by remyelination and regeneration in the CNS.

Interestingly, when multiple sclerosis patients become infected with helminths, the disease stops progressing and circulating myelin-recognizing regulatory T cells appear in the peripheral blood, indicating that helminths act as adjuvants for regulatory T cells. The incidence of MS is ten times higher for those living in northern countries and the northern United States above the 40th parallel. The rate of MS decreases significantly in populations further south. With reference to the figures, two global maps are shown, one showing the prevalence of MS and the other showing the prevalence of helminths infection. The correlation to the two is not coincidental. The exposure of a newborn to antigens derived from helminths, as well as to other *lactobacillus* and viruses, etc., promotes the normal development of the human immune system. The deprivation of such immune stimulatory factors, however well intentioned, has caused the series of recent modern day plaques as noted herein.

The countries that have seen the most pronounced rise in autoimmunity have over the same period seen tremendous improvements in sanitation and socioeconomic status. Moreover, the steady migration from rural to urban areas has dramatically reduced childhood exposure to infectious organisms. Rapid anthropogenic transformation of the environment and life style has not allowed time for the human immune system to adjust to these changes.

Diseases like T1D and MS are extremely rare in most African and Asian populations, yet increase conspicuously when these same populations migrate to a modern setting. The dramatic rise of T1D in children under 14 years of age in developed countries cannot be explained by genetic factors alone. The T1D epidemic observed over the last 50 years in Western Europe and North America is predicted to plateau. For example, Norway showed no increase over the last decade. The high T1D incidence overall trend is still rising in ex-Eastern Bloc countries and in the Middle East. As depicted in the figures, a global map indicates the prevalence of Type 1 Diabetes (T1D) in certain countries around the world and the inverse correlation between Type 1 Diabetes (T1D) and helminth diseases.

In the United States, as well as most Western societies, helminthic infestation is uncommon, if not rare. This is a fairly recent occurrence in the evolution of humans when examined from an evolutionary viewpoint. The human immune system evolved long before the emergence of modern human societies and independently of their cultural ways. Elimination of parasitic worms from Western society occurred about 50 years ago, coinciding with the rise in various autoimmune diseases. Helminths are elaborate multicellular worms, with nematodes (nonsegmented roundworms) and the platyhelmiuths (flatworms) being two groups of helminths that inhabit the human intestines. Helminth infections are highly prevalent in the human population, particularly in tropical and subtropical countries. The prevalence of helminths is highest in rural and underdeveloped areas characterized by overcrowding, poor sanitation and an impure food/water supply. When compared to areas where the standard of living is higher, asthma and allergies occur at a much lower rate in these rural and underdeveloped regions. There is a considerably lower prevalence of allergic diseases in developing countries. People in industrialized regions live in increasingly hygienic environments and, as a result, acquire helminths much less frequently than those people living in rural areas. The increase of asthma and allergic diseases in the industrialized world has also been explained by a decline in bacterial and viral infections during childhood. A reduction in the overall microbial burden is thought to result in a weak Th1 imprinting and unrestrained Th2 responses that allow an increase in allergy. Others have noted, however, that this theory is contradicted by observations that the prevalence of Th1-autoimmune diseases, such as Crohn's disease, are also increasing and that Th2-skewed helminth infections are disassociated with allergy and asthma. It appears that the worldwide trend toward greater hygiene has resulted in a worldwide "deworming" and thus, the relatively recent elimination of the chronic immune system stimulation induced by a helminthic infection is believed to possibly be a causative factor in the increase of asthma and allergies.

The so-called hygiene hypothesis asserts that bacterial and viral infections early in life direct the developing immune system toward a strong T-h1 imprinting, counterbalancing a proallergic response of T-h2 cells. The hygiene hypothesis asserts that an overall reduction in microbial burden results in an underdeveloped or weak T-h1 imprinting, leading to unrestrained T-h2 responses, resulting in atopy. But it has been noted that T-h1 autoimmune diseases, like type 1 diabetes, are increasing and that T-h2 skewed helminth infections are not associated with allergy. Moreover, more than one billion people worldwide are heavily parasitized by helminths and are rarely afflicted by allergic disease. While not bound by theory, the present inventors contend that a strong T-h2 response is not the sole precipitating factor in an allergic response. It has been shown that asymptomatic infections are correlated with high levels of another T-h2 dependent isotype, IgG4, further demonstrating the flaws associated with the belief that a strong T-h2 response is the sole cause in the development of an allergy. High levels of serum IgE are more representative of human's evolutionary past and thus, one objective of the present invention is to induce such a state to return the human immune system to a previously encountered homeostatic state where such autoimmune diseases were rare.

In one embodiment of the present invention, the effect of high levels of intestinal helminths is stimulated, thus overcoming the disadvantage of direct infection with an helminthic parasite. In a preferred embodiment of the present invention, the production of helminthic-specific IgE is initiated by administering the protein antigen specific to one or more helminths. The aforementioned antigen is isolated and collected from at least one species of helminth, preferably 3-5 separate species. The antigen is extracted from the organism(s) at any stage of development (cercariae, larval, adult worm etc.) and can be isolated from any helminth, including those that don't normally parasitize humans.

In several embodiments, the rarity of *C. hepatica* makes it one of the two preferred choices for use in various embodiments of the present invention. In another embodiment, the trematode *Dicrocoelium dendtriticum*, more commonly known as a liver fluke, is utilized. *D. dendtriticum* is a common parasite that is found primarily in sheep, and can also be used to extract protein antigens for use. In one embodiment, the antigen can derived from the nematode *Loa* that infects the skin and the eyes. Loaiasis, the disease caused by *Loa*, and the parasites themselves are only found in Africa and therefore are seen as preferred to use, except in the continent of Africa. In still other embodiments, a type of trematode or flatworm that causes the disease schistosomiasis is also preferred as its essential snail hosts are not found in the United States.

When a parasitic helminth enters the body, it begins to shed proteins and the body's immune mechanism is activated. In short, the body's immune response to a parasitic helminth causes the production of billions of Y-shaped antibodies to the foreign proteins shed by the helminth. Th2 provide help for B cells and, in so doing, are essential for antibody-mediated immunity. Bacterial, viral and protozoan infections usually stimulate a Th1 response, characterized by elevated levels of Th1 cytokines (i.e., interleukin (IL)-2, IL-12, interferon (IFN)) and effectors such as macrophages, natural killer cells and neutrophils. In such Th1 responses, cell-mediated immunity involving phagocytosis is responsible for the functional immunity. Th1-type inflammations produce large amounts of IFN-.gamma and tumor necrosis factor (TNF)-alpha. In contrast, the immune response to intestinal parasitic helminths depends on the production of Th2 cytokines (e.g., IL-4, IL-5, IL-10), which mediate antibody-dependent effector responses. Because external elements, such as dust mites, pollen and peanuts, are inappropriately determined by the immune system of allergic people to be allergens, they are met with the same IgE immune response as the body mounts against a parasitic helminth infection.

Allergists do know that IgE-mediated disorders, including asthma, food allergies, hypersensitivity and anaphylactic reactions are unlike any other immune reaction, except for one, the immune system's response to parasites. The difference between a parasite and ragweed, dust mites or peanuts, is that parasites can be fatal if the IgE antibodies do not kill them first. Allergens such as ragweed, dust mites or peanuts, however, in a non-allergic individual are harmless to the body. One aspect of the present invention involves the promotion of a mild helminth infection to protect a human against certain allergies, and in particular a peanut allergy, based on the understanding that a chronic helminth infection can block the induction of allergen-specific IgE by influencing the behavior of the peanut antigen. Helminths release a variety of molecules, known in the art as excretory and secretory products (ESP), into the host, playing a role in host immunosuppression.

One embodiment of the present invention is directed to a helminth compound that has an immunosuppressive effect, especially when augmenting the Amish soil as described herein, that is administered (as set forth herein) to an expectant mother and to a newborn during its first year of life. An embodiment of the present invention therefore includes a method using a helminth compound in an amount sufficient to eliminate, ameliorate, or reduce the excessive immune response in an asthmatic and or allergic individual.

Type 1 diabetes (T1D) results from autoimmune destruction of beta cells in the pancreas, the only cells that make the vital hormone insulin. Despite daily insulin injections, individuals with T1D have an increased likelihood of heart disease, stroke, kidney disease, and blindness. T1D incidence in developed countries has been rising at the rate of 3-5 per cent, per year over the past 50 years. One aspect of the present invention is directed to the prevention and/or reduction in the occurrence of T1D by manipulation of the microbiome at the time of birth, preferably also months prior to birth in the expectant mother's environment, and still further preferred in the environment of the newborn for the first year of life. Thus, one aspect of the present invention is directed to the provision of "diabetes-protective" bacterial products that are intended to induce the development of the immune system in a manner that confers protection from T1D, as well as many other autoimmune diseases. Infants living in Sweden had more Clostridia than Estonian infants, whereas Lactobacilli and Eubacteria were more frequent in Estonian infants. Type 1 diabetes incidence is 26 cases per 100 000 population every year in Sweden, but only 10 per 100 000 in Estonia. Thus, one aspect of the present invention is to reduce if not prevent a newborn during birth and for at least the first few days of life, from being exposed to clostridia and *bacteroides*.

There is a strong positive association between occurrence of type 1 diabetes and asthma at the population level, despite the fact that type 1 diabetes is a T-helper-1 (Th1)-mediated autoimmune disease, whereas atopic disorders are characterized mainly by a T-helper-2 (Th2) immune response. In the past 50 years, a progressive increase in the prevalence of type 1 diabetes and asthma has been seen in populations in more-developed countries.

In various embodiments, the augmentation of Amish-derived soil (also generally referred to herein as "Amish-soil", etc.) is accomplished by adding to Amish derived farm soil (as defined herein) an amount of a helminth compound—preferably in an amount equal to at least 10% of the total amount of soil employed—in an urban environment (where an expectant mother resides). The helminth compound augmented portion preferably comprises a pathogen-free, non-human colonizing helminth consisting of one or more of a live adult helminth, ground adult helminth, adult helminth extract, adult helminth ESP, live helminth larvae, ground helminth larvae, helminth larvae extract, helminth larvae ESP, live helminth eggs, ground helminth eggs, helminth eggs extract, or helminth eggs ESP. The helminth compound is preferably made from the group of helminths that colonize other animals, but not in humans, and has no associated pathology in humans. The helminth compound derived from these groups will establish only a transient infection in the human or will simulate the same, and, in doing so, stimulate the immune system in a way in which it may protect allergic humans from the inappropriate immune response associated with allergies and asthma. In one preferred embodiment of the invention, the helminth to be used is *Haemonchus contortus* (*H. contortus*), or ESP therefrom, to simulate a parasitic helminth infection.

The invention thus relates to a method of treating allergic and other IgE-mediated disorders, including, but not limited to, asthma, allergies, specifically, common food allergies, hypersensitivity and anaphylactic reactions, which are marked by an inappropriate IgE immune response including an aberrant and/or enhanced IgE antibody production to benign antigens, with a non-human colonizing helminth compound. In a preferred embodiment, a non-human colonizing helminth compound is used, in an amount sufficient to establish a transitory parasitic helminth infection and or to simulate in a parasitic helminth infection, thereby having an immunosuppressive effect against benign antigens and or stimulating a regulatory immune response as a therapy or prophylaxis of allergy and other IgE-mediated disorders in a newborn. The administration of the helminth compound as an augmented agent to the Amish soil, delivered as disclosed herein to both an expectant mother and to the newborn during its first year, prevents or at least largely ameliorates allergic sensitivity, including but not limited to T1D, MS, peanut allergies, autism and stuttering.

The helminth compound used in the augmentation of the Amish soil is preferably derived from *H. contortus,* or from the group of helminths from the families of Ostertagia, Trichostrongylus, Trichostrongylus, Bunostomum, Nematodiriasis, Oesophagostomum, Trichuriasis and Chabertia.

A helminth-based agent, as defined herein, shall mean any antigen isolated from one or more species of helminths or any antibody directed to such antigen. Derivatives of such antigens or antibodies, including amino acid fragments or synthetic, chemically modified or substituted fragments are also included within this definition. In a preferred embodiment, the antigen is isolated from 3-5 different nematodes, trematodes and/or cestodes. Preferably, the antigen is isolated from *Capillaria hepatica* and/or *Dicrocoelium dendtriticum* and/or Schistosomes.

In comparing breast-and bottle-fed infants, others have found that different diets not only promoted different intestinal bacteria (microbiota), but that there is a dramatic effect of such microbes on shaping immunologic development. For example, breast-fed macaques had more "memory" T cells and T helper 17 (TH17) cells, which are known to fight *Salmonella* and other pathogens. Such differences persisted for months after the macaques had been weaned and placed on identical diets, indicating that variations in early diet has long-lasting effects. In short, infant microbes leave a long-lasting imprint on immune function. Breast-fed macaques had larger numbers of the bacteria *Prevotella* and *Ruminococcus,* (with the bottle-fed group having a greater abundance of Clostridiu); a more diverse microbiota; and a much larger percentage of experienced memory T cells. This supports the present inventors' contention that immunologic characteristics are imprinted at birth and during the first few months of life. Gut microbiota present in early life leave a durable imprint on the shape and capacity of the immune system, essentially programming the system and influencing T cell development. The kind and characteristics of microbes present at birth of a newborn, as well as in mother's milk due to the exposure of the mother during her pregnancy to such microbes, has a direct impact as to whether the newborn child will develop autoimmune disease.

With respect to another aspect of the present invention, one long felt but unsolved problem relates to how to best inoculate an infant so that problematic issues are avoided in its future development of a robust immune system. In one embodiment, devices are employed to increase the exposure of an expectant mother to aerosol-conveyed compounds derived from farm soils obtained from farms where animals (especially bovines) reside and that have had few if any antibiotics administered to them. This ensures that such animals do not have their digestive systems altered in a manner that would detrimentally affect the normal populations of resident bacteria flora in their rumen. In addition to the mother, an infant right after birth, preferably within the first hour to four hours of birth, is also exposed to such compounds, either via an aerosol or by a compound being administered topically or nasally (but which may also be ingested by the infant), and most preferably continuing such exposure to the infant for its first year of life, e.g. during which time the infant immune system is developing. The aerosol and/or topical composition preferably includes a certain population of *B. longum* bv. *Infantis*. It may be provided in the form of a topical lotion, as well as in a form that may be ingested and swallowed by the newborn. In such a manner, the infant is properly exposed to beneficial bacteria that will assist in properly charging the nascent immune system so that it develops in a fashion that avoids later life allergic reactions to nuts, shellfish, dogs, as well as the other autoimmune disease set forth herein.

It is believed that the co-evolution of humans with various farm animals, including bovines, resulted in exposure of humans to the myriad of bacteria, viruses, and other agents that trigger a human mother's immune system, and created an environment so that a natural and beneficial production of mother's milk rich in *B. longum* bv. *Infantis* was generated for the infant's consumption. Mother's milk further includes glycan, which also contributes to defeating pro-inflammatory responses while encouraging anti-inflammatory responses. Also included in mother's milk is 2-fucosyllactose, found to be effective in warding off various pathogenic bacteria. The infant gut is not very acidic and without supplementation by mother's milk, is largely devoid of a significant number of enzymes. Inactive enzymes in the mother's milk are thus converted into a natural, active form in the infant's gut.

Using the present invention, a vast number and array of allergies and autoimmune diseases can be reduced, if not prevented, without fully understanding the admittedly complex mechanisms involved in the evolutionary developed systems that exist between farm animals, human mothers and developing infants, all of which are involved in the development of a robust and effective immune system for an infant. But despite the numerous unknowns in the various details of immune system development, the present invention discloses some of the basic fundamental aspects that are required to properly permit the creation of an environment where an expectant mother's immune system is charged with lactobacteria and other organisms derived from farm animals that humans have long cohabited with, such that an infant, via swallowing amniotic fluid of the mother, exposure to such bacteria in the vaginal tract, and also provided with enzymes, HMOs and other compounds in the mother's milk, that enhance the beneficial populations of various bacteria, including especially, with such environment providing a rich milieu that encourages the development of an infant's immune system.

It is known that meconium most often is dominated by *lactobacillus*. The source of such *lactobacillus* in the infant—while it is in the amniotic fluid—is believed to originate from the mother's exposure to various *lactobacillus*. Thus, the exposure of an expectant mother to particular *lactobacillus*, especially those found in for example, Amish farm soil where bovine and other farm animals reside, is important to convey such particular *lactobacillus* to the developing fetus, thus providing the proper development of the immune system to avoid the occurrence of allergies and other autoimmune diseases. Before birth, the digestive tract of the fetus is purportedly sterile, but within hours of birth, the baby acquires a complex collection of microorganisms which populate the mouth—then eventually the full length of the tract is colonized. The development of specific microorganisms is influenced by the exposure to certain factors, namely maternal microbiota and the infant's diet. Although the mouth is not considered part of the digestive tract, it provides access for microbes to enter and colonize the infant's digestive tract.

The mode by which a baby is delivered can determine the nature of microbes that contact the infant or that may be ingested by the infant. Through normal vaginal birth, an infant is exposed to the mother's vaginal and fecal flora, which results in the colonization of *Lactobacillus, Bifidobacterium, Escherichia coli,* and *Enterococcus*. However, an infant delivered by Caesarian section is exposed to a different assortment of microbes, such as *Clostridium* and *Streptococcus*. These microbes can establish and colonize rapidly within the sterile digestive tract of the newborn, because there are no pre-existing microbes to compete with. Research suggests that babies born via C-section are more likely to develop allergies, asthma and other immune system—related troubles than are babies born the traditional way. Babies born vaginally were colonized predominantly by *Lactobacillus*, microbes that aid in milk digestion. In contrast, C-section babies are colonized by a mixture of bacteria typically found on the skin and in hospitals, such as *Staphylococcus* and *Acinetobacter*. Babies born vaginally carry bacterial populations that match those of their mothers' vaginas, while the C-section babies have a mixture of bacteria similar to that found on the skin of the mothers. Birth by Caesarian section and a formula-based diet increases colonization of Clostridia in an infant's gut. Cesarean section is associated with an increased risk of childhood asthma and eczema. The most common *Clostridium* species found in an infant's gut is *Clostridium difficile*. *Clostridium difficile* can colonize in large numbers in the intestines, increasing the production of toxins. These toxins are what causes diarrhea in infants. Mass colonization of *Clostridium difficile* can be life-threatening to especially infants who are taking antibiotics, because the antibiotics can target potential *C. difficile* competitors, reducing their colonies.

| Breast-Fed Infants | Formula-Fed Infants |
|---|---|
| The digestive tract is colonized by primarily Bifidobacteria. | The digestive tract is colonized predominantly of *Bacteroides* with some Bifidobacteria; but over time the difference in the number of colonies of the two genera decreases. |
| Human milk has antimicrobial factors that lower the growth of facultative anaerobes. | There exists a more complex flora consisting largely of facultative and obligate anaerobes, such as Enterobacteria, *Streptococcus* and *Clostridium*. |
| Intestinal lumen is acidified more easily because human milk does not serve as an efficient buffer. | Intestinal lumen is closer to a neutral pH. |
| Infants are less prone to infections due to a large amount of Bifidobacteria. | Infants are more prone to infections due to the lower amount of Bifidobacteria. This can result in a higher risk of diarrhea and allergies. |

*Bifidobacterium* species colonize in great numbers in the infant digestive tract, regardless of whether the infant is breast-fed or formula-fed. The most common *Bifidobacterium* species in infants are *Bifidobacterium infantis, Bifidobacterium breve,* and *Bifidobacterium longum*. However, *Bifidobacterium infantis* is specifically unique to the infant's digestive tract as they are gram-positive microbes and are oxygen intolerant; hence, they colonize within the intestines rather than the stomach (e.g. since the intestines are not well-oxygenated regions like the stomach). Being Gram-positive bacteria, *Bifidobacterium infantis* have a thick cell wall for extra protection from other residing microbes within the intestines.

Oligosaccharides, such as N-acetylglucosamine, glucose, galactose, and certain glycoproteins found in human milk, are potential growth factors for *Bifidobacterium*. About 50%-90% of human milk oligosaccharides pass through infants undigested. *Bifidobacterium* is able to break down these undigested sugars and obtain energy and nutrients for growth. *Bifidobacterium infantis* prefer glucose over other oligosaccharides due to the availability and abundance of glucose, as well as the lower level of difficulty for them to metabolize glucose. With the assistance of intestinal peptidases, such as alpha-glutamyl transpeptidase, aminopeptidase, oligoaminopeptidase, and carboxypeptidase, the food ingested by the infant can be broken down further for the microbe to access and utilize essential components more effectively.

Increased colonization of *Bifidobacterium* in the large intestine, and its interaction with Lactobacilli, results in enhanced carbohydrate fermentation. Fermentation results in an increased production of acetic acid, butyric acid, and lactic acid, which creates an acidic barrier against pathogenic bacteria. *Bifidobacterium infantis* interacts with *Lactobacillus salivarius* to exert immunomodulatory effects on intestinal immune cells that mediate host responses to flagellin and pathogens. They are able to modulate the intestinal epithelium by making *Salmonella typhimurium* less virulent as well as weakening flagellin-induced pro-inflammatory responses. Both species interact to down-regulate the secretion of basal IL-8, but *Bifidobacterium infantis* specifically inhibits flagellin-induced IL-8 secretion. Flagellin serves as a key activator of pro-inflammatory responses to specifically *Salmonella* intestinal epithelial cell responses. The major point to understand from this is that *Bifidobacterium infantis* interacts with *Lactobacillus salivarius* to modulate intestinal epithelial cell responses by limiting IL-8 secretion. While they are interacting to weaken pro-inflammatory responses, they may encounter other microbes such as *Bacteroides vulgatus* that activate pro-inflammatory gene expression in intestinal epithelial cells.

Lactobacilli are Gram-positive rods that can be found throughout the digestive tract, but are predominantly present in the large intestine. Lactobacilli can infiltrate an infant's sterile digestive tract by means of contact with the mucosal surface of the mother's vagina or from the mother's breast milk. Lactobacilli are second only to Bifidobacteria in dominating the microbiota of breast-fed infants. The most common species of *Lactobacillus* found in infants is *Lactobacillus acidophilus*. Lactobacilli contribute to digestion, stimulate the immune system, and inhibit the growth of pathogens. They live in habitats rich in carbohydrates, such as an infant's digestive tract. Lactobacilli, a member of the lactic acid bacteria group, break down sugars, mainly lactose, into lactic acid using the enzyme beta-galactosidase. Sugar metabolism provides nutrients and energy for its growth and survival. The accumulation of lactic acid lowers the environmental pH, which inhibits the growth of pathogenic bacteria, such as *Helicobacter pylori*. Lactobacilli can regulate their enzymatic activity to achieve a more suitable or optimal living condition. They can also inhibit growth of other bacteria by competing with them for nutrients and adhesion sites on the epithelial lining of the intestinal wall. Lactobacilli are commonly used as probiotics, supplements containing bacteria that are beneficial to humans.

*Escherichia coli* is a Gram-negative, facultative anaerobic, and non-sporulating bacterium that generally reside in the infant's intestines and is one of the first and most abundant bacteria that colonize the intestines. The growth of *E. coli* is suppressed when human milk is present in the digestive tract, because the proteins present in the human milk create a hostile environment for *E. coli*. The presence of Bifidobacteria stimulates the diversity of sugars that the *Bacteroides* can degrade for nutrients and energy. *Bacteroides fragilis* is able to enhance the function of various T cells.

The first bacteria exposed to a baby's system are critical for establishing the microbial environment of that individual. Thus, exposing the infant to beneficial bacteria that can properly prime its immune system is critical to the avoidance of allergies later in the baby's life. Colonization of a baby's system is believed to begin at least in the later stages of pregnancy of the mother and by the time of birth, a microbial community already dwelling in the baby is demonstrated by such populations of bacteria showing up in the first poop of some babies born prematurely. While a baby is in the uterus, it typically swallows 400 to 500 milliliters of amniotic fluid, which harbors some of the mother's microbes. Colostrum, the "first milk" produced by mammals immediately after giving birth, contains compounds involved in supporting the newborn infant's immune system. Colostrum contains an array of antibodies to common allergens that can affect humans. Similar antibodies are built up over time by cows as they themselves respond to allergens in their environment. Praline-rich polypeptide (PRP) is believed to be a main component of colostrum responsible for eliminating or improving the symptoms of allergies. PRP's ability to reduce allergic symptoms is thought to be partly due to the creation of special cells (helper T-cells and suppressor T-cells) which suppress and switch off the immune response. Maternal passive immunity is a type of naturally acquired passive immunity, and refers to antibody-mediated immunity conveyed to a fetus by its mother during pregnancy. Human babies receive passive transfer of immunity via the placenta before birth. Maternal antibodies are passed through the placenta to the fetus by an FcRn receptor on placental cells. This occurs around the third month of gestation. Passive immunity is also provided through breast milk.

In vaginally-born babies, the bacteria destined for the gut microbiota originate primarily in the maternal birth canal and rectum. Thus, one aspect of the present invention relates to the purposeful colonization of a woman's anus and vagina with beneficial bacteria just prior to birth so that the newborn baby will be primarily exposed to such bacteria, rather than other bacteria that may be harmful to the child and preclude a robust development of an immune system that can avoid allergies, asthma, MS, T1 diabetes, and other autoimmune diseases, etc. Thus, one aspect of the invention is directed to a method via which a bacterial containing lotion, gel or cream is administered topically to an expectant mother's vaginal and anal region prior to birth, preferably at least about one hour before birth but in any event prior to the time the baby exits the vaginal canal. In C-section births, the woman is prepared by having such gel, lotion or cream purposefully provided to the infant as soon as the baby is withdrawn from the mother during the C-section delivery. Preferred gut microbes to use in topical compositions include those that cause testosterone levels to rise, as it has been found that small elevations of testosterone has an additive effect in the prevention of autoimmune diseases and a role in the regulation of immune-mediated diseases.

After lactose and lipids, human milk oligosaccharides (HMOs) are quantitatively the third largest and most diverse component of breast milk. *B. longum* bv. *Infantis* facilitate a protective gut colonization in breast-fed newborns. Infants cannot digest HMOs which arrive intact in the large intestine. While having no apparent direct nutritional role, HMOs modulate the establishment of a protective microbiota, enriched in bifidobacteria and exclusively characteristic of breast-fed infants. Modern infant formulas are increasingly supplemented with plant oligosaccharides that elicit an unspecific bifidogenic response, lack the complexity and diversity of HMOs.

Although the *Bifidobacterium* genus shares phenotypic features typical of lactic acid bacteria, such as acid production, they belong to the Actinomycetales branch of the high-G+C Gram-positive bacteria. Bifidobacteria represent one of the most important bacterial groups of the human gastrointestinal tract, their numerical dominance up to 90% in infants.

Metronidrazole kill beneficial bacteria, but is given to women with BV. Thus one aspect of the present invention relates to the avoidance of certain antibiotics by expectant mothers, and especially to mothers at or around the time of birth of a baby. *Bifidobacterium* is a genus of Gram-positive, anaerobic, non-sporulating, usually branched rod-shaped bacteria. They are found in the human gastrointestinal tract and the female vagina and urogenital tract, but only amount to 3-6% of the total flora in adult feces. *B. infantis* is a sub-species of the *Bifidobacterium longum* species and produces predominantly acetic acid. One strain, *B. infantis* BCRC 14602 produces "Bifidin I" that is effective against the growth of many other bacteria, including *Listeria monocytogenes*, a common cause of food spoilage and food-borne diseases.

As set forth herein, various embodiments of the present invention relate to a topically applied composition that comprises a population of pre-selected microbes or components thereof and comprising various non-pathogenic bacteria. In one such embodiment, a formulation comprises a mixture of various amounts of two or more of the following: *Bifidobacterium longum, B. infantis* BCRC 14602; *Prevotella; Ruminococcus, Bifidobacterium infantis, Lactobacillus acidophilus, Bacteroides fragilis, B. longum* bv. *Infantis* isolate UCD272; *B. infantis* BCRC; *B. longum* bv. *Infantis*, AY151398; and *Lactobacillus ruminus*.

As one of skill in the art will appreciate, a suitable topical composition comprising a population of the above bacteria can be, in various embodiments, a cream, lotion, emulsion, gel, ointment, liquid or spray. In one embodiment, the topical composition is formulated to provide at least about $10^2$ bacteria per $cm^2$. In another aspect, a method of treatment is provided, wherein a composition as described herein is topically applied to the skin of an expectant mother at around the time of birth, and also preferably during the first year of the baby's life. In certain embodiments, topically applying includes topically applying to a mucosal surface (nasal, vaginal, rectal, oral surfaces) of the expectant mother and/or directly to the baby.

In yet another embodiment, a topical vaginal lotion comprises a mixture of *Lactobacillus johnsonii*, and *Bifidobacterium longum* bacteria and is applied just prior to birth to provide an opportunity for the newborn to be first exposed to such bacteria, thus enhancing the chances that the baby's immune system will properly form in a manner that avoid allergies and autoimmune diseases.

In still another embodiment, a baby's first bath is in a concoction of a rich variety of *lactobacillus* and other immune enhancing agents to prevent the life threatening diseases as discussed herein. In addition to a variety of the various bacteria, helminthes extracts, etc. as set forth herein, a suitable lotion may also include amounts of sugars that the various *lactobacillus* microorganisms may assimilate to survive and thrive. These sugars and life bacteria supporting compounds are known to those in the art and as otherwise referenced in various incorporated writings. As certain spermicides and contraceptive creams can kill *Lactobacillus* species, it is one aspect of particular embodiments of the present invention to avoid the use of such formulations during pregnancy and during the first year of a newborn's life, as the prevalence of a rich variety of *lactobacillus*, as noted herein, is a desired objective to achieve in the overall environment of the expectant mother and the newborn for the first year of life. In this vein, the avoidance of any type of aerosol sprays that could also kill bacteria in the environment of the expectant mother and the newborn is to be encouraged.

The incidence in the rise of allergies and the increasing non-exposure of individuals to farm environments shows a curious symmetry. The present inventors submit that such correlation is anything but coincidental and that a principal reason why there has been an allergy epidemic is due to the fact that particular allergens, long previously experienced by humans in their living environments, have been purposefully excluded from the modern urban environments where most humans now reside. It has been observed, in analyzing people's gut bacteria by their occupation, that those who had regular contact with livestock, such as farmers and their wives, had bacterial communities dominated by *Prevotella*, a type of bacteria that is also abundant in the gut microbiota of cattle and sheep.

Cattle were domesticated about 6000 years ago by humans. For thousands of years, humans have lived in close proximity to farm animals, and in particular cows. Increasingly over the last century, and especially in the last few decades, humans have gravitated toward urban environments to reside, where exposure to farm animals is limited. Bovines are subfamily of Bovidae family, and they utilize rumination (re-chewing food) as a mechanism of feeding. They have four stomach compartments that allow them to be successful in rumination. Of the four, rumen is special in that it contains billions of microbes that help the bovines to digest the food. The bovine rumen shows an incredible variety of organisms ranging from fungi, bacteria, archaea, protista, and viruses, namely bacteriophages. Their functions are to help in the breakdown of the various foods that would pass through the rumen, namely plant matter such as grasses, and its various difficult components.

The microorganisms that live in the bovine rumen live in a symbiotic manner and utilize the byproducts of one another for their own benefit. Bovines can eat a wide range of feeds because they have many different kinds of microbes to help them digest. The rumen-microbial system is sensitive to sudden changes in feed-types, as well as to antibiotics. Sudden changes in food content or administration of antibiotics to a bovine results in a change in the population of gut microbes, often leading to sudden changes in pH, sometimes causing acidosis. Therefore, one aspect of certain embodiments of the present invention relates to obtaining manure from bovine where such animals have their nutrition maintained so as to preserve the native microbes in the rumen.

Cows appear to have a heightened ability to fight disease. This may be an adaptation in the cow to the large number of bacteria carried in the rumen as a more robust immune system is required to prevent transmission of infections in animals living in large herds. When a bovine eats, billions of bacteria, protozoa, yeast, and molds in the rumen help the animal to be able to eat and digest the great amount of grasses.

There is a symbiotic relationship between the cow and its various bacterial and fungi microorganisms, which include: bacteria, ciliate protozoa, anaerobic fungi, bacteriophages, and archeabacteria. The most common protozoans in the rumen are of the genuses, *Epidinium, Entodinium, Diplodinium,* and *Holotrich ciliates*. In a cow's rumen the most common microorganisms are gram-positive cocci and rods.

Although previously some believed that all cattle had essentially the same bacteria in their gastrointestinal tracts, that has proven to be mistaken. Percentages vary but *Prevotella* is often the most common bacterial genus in the cattle, with *Clostridium* often also prevalent. Bacteria in beef cattle are often not shared with dairy cows and there is often a vast assortment of bacteria varying from individual to individual, even when animals consume the same diet and are of the same breed, gender, and age. Thus, in preferred embodiments of the present invention, the source of manure-containing soil is preferably selected from a combination of at least two or more, and preferably three or more separate sites where different bovine animals are present. This is one way in which to enrich the number and variety of allergens sought to be obtained and disseminated to expectant mothers so as to enhance the immune systems of their unborn babies.

In the last 50 years there has been an exponential increase in various diseases of immune dysregulation in the developed world. However, regions of the world where helminth parasites are still endemic because of poor sanitation, have a lower prevalence of allergies and autoimmune diseases. Various helminths have been shown in many studies to suppress the symptoms of many different types of experimental autoimmune diseases (e.g., experimental autoimmune encephalomyelitis, type 1 diabetes, arthritis, and colitis) as well as allergic conditions of the skin, intestines, and the airways. The present inventors believe that properly timed helminth exposure stimulates a person's immune system in a manner that enhances the immune regulatory response.

Certain embodiments of the present invention involve the addition of one or more allergens to a naturally obtained sample of soil from an Amish farm (which herein will be understood to be a farm on which little, if any, antibiotics are employed that would significantly alter the natural population of *lactobacillus* in a bovine's gut that resides on such a farm). Thus, in several embodiments, the augmentation of a naturally obtained sample includes the addition of portions of helminthic species that elicit a therapeutic immune response, such as immunoepitopes and other antigenic determinants, directed against IgE antibodies. These include molecules that are excreted or secreted from such helminthic species. As a representative of the members of the genus excretion-secretion molecules to which the claimed invention may be drawn, the following guidance and disclosure is intended to reflect preferred embodiments: *Haemonchus contortus,* including concentrated supernatants thereof that may be heated to about 95 degrees Celsius for about 15 minutes. Such a supernatant may be obtained, for example, by harvesting adult *H. contortus* worms from infected sheep, culturing the harvested worms in a suitable medium, collecting and concentration of the supernatant and heating the same for about 15 minutes at 95 degrees Celcius, and thereafter adding such supernatant to the Amish soil as described herein.

The helminth families from which supernatants and useful molecules can be collected include the following: Ostertagia, Trichostrongylus, Bunostomum, Nematodiriasis, Oesophagostomum, Chabertia and Trichuriasis. Ground helminth larvae is a preferred way to obtain such materials for augmentation to the above referenced soil.

Still other embodiments include a composition that augments the soil as described herein, such composition comprising an extract from worms selected from the group of *Capillaria hepatica, Dicrocoelium dendriticum,* such extracts effective to present a pharmaceutical formulation for increasing serum levels of IgE in a human, to greater than about 3000 IU/ml thereby ameliorating the allergic reaction of the human to a plurality of allergens, with a helminth-based antigen being present that includes a protein of at least about 50,000 molecular weight selected form one of the above referenced helminthes. In still other embodiments, a human is treated via exposure of an expectant mother and a newborn during its first year of life to Amish derived soil as set forth herein, augmented by a composition that includes a helminth extract, preferably from a helminth parasite stage of a parasite larvae, such helminth selected from the group (in addition to those listed above): *Ascaris lumbricoides, Enterobius vermicularis, Trichuris trichiura, Ancylostoma duodenale, Necator americanus, Strongyloides stercoralis,* and *Trichinella spiralis.*

While not being bound by theory, one aspect of the present invention is to calibrate a mother's immune system to confer desired immunity against a variety of allergens and associated allergies, thus achieving a naturally occurring immunotherapy. Exposure of allergens particularly those contained in manure-containing soils from farms that have particular animals residing thereon, and in particular bovines, is one effective way in which to achieve the desired immunity conferring objectives of the present invention.

One embodiment of the present invention includes the exposure of a pregnant mother to a composition that includes *Prevotella. Prevotella* are among the most numerous microbes culturable from the rumen and hind gut of cattle and sheep, where they help the breakdown of protein and carbohydrate foods. *Prevotella,* credited interchangeably with *Bactericides melaninogenicus,* has been a problem for dentists for years. *Prevotella* is a human pathogen known for creating periodontal and tooth problems. Thus, one of skill in the art of attempting to confer immunity to pregnant mothers would be disinclined to employ *Prevotella* in such a composition. This is a classic example of a teaching away from the present invention as *Prevotella* are considered to be opportunistic pathogens in humans. The use of such microbes, however, in the controlled dispersion devices and methods as set forth herein, provide a means for conferring the life-saving immunity factors presently lacking in urban environments.

Thus, one aspect of the present invention is to change the composition in pregnant mothers of their gut bacteria, otherwise known as the mother's gut microbiota. In particular, *Prevotella* strains are included in preferred compositions, which are gram-negative, non-motile, rod-shaped, singular cells that thrive in anaerobic growth conditions. In more preferred embodiments, however, it is not just this particular microbe that is sought to be employed to confer immunity—but a collection of microbes and their synergistic relationships with fungi and other microbes, especially those present in the bovine gut.

As one will appreciate in view of one principal theory of the present invention, it is important to obtain microbes that are derived from manure that is produced by animals that are not treated with particular types of antibiotics, and particularly antibiotics that adversely affect *Prevotella,* as well as other populations of microbes in the bovine gut. Moreover, in a preferred embodiment, the diet of the cows from which manure is obtained is maintained at fairly standard levels and is not switched in a manner that causes a radical change in the population of microbes in the animal's gut (which occurs to accommodate digestion and which is causative of the often experienced acidosis of a cow's gut when treated with antibiotics as antibiotics destroy resident population of the gut microbes). Thus, a steady diet to a cow is preferred to achieve the benefits to be derived from collection of its microbial generation from its gut, and the avoidance of antibiotics is preferred so as to obtain the best manure for the purpose of conferring immune resistance to newborns via a mother's exposure to such microbes prenatally. In a preferred embodiment, the soil that contains cow manure is derived from manure of an animal in which no antibiotics or growth hormones were used, including rBST or rBGH. One way to identify appropriate farms for farm soil to employ is to ensure that they are producers, for example, on an "organic" farm where organic farm raised animals are raised, such as on a dairy farm where Amish butter is produced—as that would indicate that the farmers use grass-fed cows raised without antibiotics, chemicals, or hormones. But origination from an Amish farm is no guarantee as many Amish have used antibiotics for years as they have found they have to compete with the rest of the farmers. Thus, in preferred embodiments, farm animal manure, and in particular bovine manure from animals that are not exposed to antibiotics, is sought after so that soil compositions obtained from such farm areas, preferably within 30 to 90 feet around a barn structure where cattle are sheltered, is collected and transported to an urban dwelling where an expectant mother resides. In even further preferred embodiments, the farm having the above referenced farm and bovine animals also has poultry, preferably chickens, and such poultry are similarly also preferably raised free of antibiotics. The soil collected and transported to an urban dwelling is thus preferably soil that contains at least some manure derived from antibiotic-free raised poultry. Most of the chicken industry uses antibiotics and arsenic to support growth but many organic and Amish farms raise chickens that are never given any form of antibiotic or arsenic. Thus, it is important in preferred embodiments, to obtain farmyard soil from organic farms, of which Amish farms may or may not be.

In various embodiments of the present invention, one aspect includes the obtainment of manure from farms that raise cattle and in which particular cattle are largely free of antibiotics, such list of antibiotics including those effective against *Prevotella*. About twenty identified species of *Prevotella* are known to cause infection, including *Prevotella dentalis*. Antibiotics for treating *Prevotella* include metronidazole, amoxycillin/clavulanate, ureidopenicilins, carbapenems, cephalosporins, clindamycin, and chloramphenicol (Pavillion). Thus, in one embodiment, avoidance of one or more of the above antibiotics in the raising of cattle on a farm from which manure-containing soil is obtained—is preferred.

While not bound by theory, one goal of the present invention is to recreate both the substance as well as the timing (e.g., during pregnancy and at least one month thereafter) and frequency of exposure (e.g., at least 3 times a week for at least 5 minutes) to manure-containing soil that is sufficient to achieve an increase in the number of T cells in the cord blood of the mother with a newborn child. Thus, one objective of various embodiments of the present invention is to provide a rich array of microbial stimuli, that resembles the world in which the human immune system evolved, including human's long and close relationship with farm animals, and in particular, bovine animals.

Without being bound by theory, it is believed that the purposeful exposure to expectant mothers to a select group of antigenic materials commonly found on farms in areas where the incidence of allergies of the resident populace is small, is effective in reducing, if not preventing, allergies in newborns. Preferably, the soil material gathered for various embodiments of the present invention are collected at specified times of year so as to increase the prospects that a particular multitude of germs (e.g. those present in manure form farm animals, and particularly cows) are resident therein, thus providing the desired antigenic responses in a fetal nascent immune response. Thus, in one embodiment, the soil is collected in non-summer months as it is believed that various germs are not present in soil samples when such samples are recovered in summer months.

In certain aspects of the present invention, there is both a timing aspect as to when samples are collected, as well as to the location of where the soil samples are taken. A fetus' immune system can be stimulated by certain bacterial cell wall components found in cow manure and similar farm derived soils. It is believed that a fetus' new immune system requires exposure to certain microbes, like those associated with cows, straw, fodder storage rooms, poultry and manure, to calibrate in a manner such that its immune system doesn't overreact to normally safe substances, like pollen, dog fur, or peanuts, or get stuck in a chronic state of overreaction, causing inflammation. In certain embodiments of the present invention, the farm soil samples include populations of at least two bacteria (*Lactococcus lactis, Acinetobacter Iwoffi*, and more preferably further include *Firmicutes, Streptococcus, Actinobacteria*, as well as fungi such as *aspergillus, Wallemia, Mucorales,* and *Russulales, actinomycetes*, filamentous bacteria. Thus, provision of a predetermined sample of farm soil having a certain biomass composition and/or bioaerosols is believed effective to expose expectant mothers, and thus their unborn children, to particular antigens associated with animals and farm dirt while in utero, thus boosting the fetal immunity and lessen the prospects for allergic conditions and asthma later on.

The present inventors submit that modern urban life radically reduces exposure to microbes and parasites that have been part of the human ecosystem for eons. It is believed that one reason why periodic exposure to farms by city dwellers has failed to illicit the desired immune protection is that such visits are too infrequent; do not expose the persons to the microbes at the correct time of year, in the adequate amount and duration; may involve exposures that, while otherwise sufficient, may be negated by the presence of lead; are at the wrong season of the year to achieve maximum benefit, etc. Moreover, having pregnant mothers travel distances when in the months of pregnancy—with all the hassles entailed in traveling, etc.—especially during the cold months when certain microbes are most prevalent—is difficult if not entirely impracticable. Thus, family trips to the farm with mothers-to-be is simply neither a solution nor proven to be effective in passing desired immunity onto the unborn child. The frequency, duration and exposure to appropriate types of microbes and other immunologic agents on such visits is believed to be insufficient to confer immunity to the unborn and/or infants.

It is speculated that exposure to certain allergens prime a person's immune system to develop appropriate responses to dangerous organisms and viruses and that the absence of such exposure is responsible for the sky rocketing occurrence of allergies and other autoimmune diseases. The season in which certain microbes are prominent in the environment may also explain why attempts to purposefully expose individuals to farm microbes is not effective as such microbes are not necessarily present in the amounts necessary for sufficient exposure at certain times of year. For example, celiac disease is more common among children born in the summer, when needed exposure to seasonal germs might be lowest. Thus, one aspect of the present invention concerns the obtainment of microbes from farms at particular times and seasons such that desired microbes and fungi can be obtained in desired and effective amounts. Preferably, manure-containing soil is collected at various times of year and such samples are rotated and used in succession such that pregnant mothers and newborns are exposed to a wide variety of microbes derived from such soils.

Yet another aspect of the present invention relates to a business directed to the provision of at least samples (and either the sale or rental or loaning of devices described herein) of manure-containing soil to customers for use in accordance with one or more of the present embodiments. For example, in one particular embodiment, samples of manure-containing soils are obtained from Amish farms whereby the owners/operators thereof certify and verify and confirm that no antibiotics at all (or at least none of specified antibiotics that are determined to affect the antigenic properties sought to be conveyed by the soil sample) have been administered to particular farm animals, in particular cows and/or poultry that reside on the farm. Samples of such soil are then packaged in user friendly amounts in sealed packages for shipping to urban dwelling customers. Such soil samples are preferably provided to customers on a predetermined basis, such as a weekly, biweekly or monthly basis—thus offering a variety of types of soils with varied characteristics to trigger desired immune responses, and also preserving the native moisture content in the soils and presumably then ensuring that the microbes, fungi, viruses, etc. present in the samples when collected are nearly as viable as when they were collected, hence preserving their immunogenic potential. A variety of other business plans may be offered, similar in a way to established fruit of the month clubs, but here, instead of fruit, soil samples are provided: from different locales; and/or those selected from farms having certain characteristics by either geography, animal makeup, number of animals, kinds of animals, how manure is collected, when manure is collected, by the microbial or fungi or viral content in such samples (as established via periodic testing by the provider); by the region of the country, by particular animal husbandry practices, including, for example, organic animal raising techniques; the absence of antibiotic administration, the type of feed employed for the animals, the mix of manure from different genus and/or species of animals, the particular percentage combination of manure and/or soil from certain farms, the moisture content of the soils, the particular month of the year that a sample was collected and/or shipped, etc. Labeling of such sealed packages with identifying information as to the collection date, locale, etc. is preferred. Thus, a wide variety of different characteristics can be determined via which a customer can order particularly focused soils (as well as any of the devices whereby soils are used therein, including plants having such soils in pots) that possess any particular type of immunogenic characteristic sought by such consumer. Providing the ability to select how often such samples are sent, preferably via an over-night service, but also possibly by regular mail or shipping, presents a consumer with a variety of samples such that the various devices herein described can be provided with such samples to enable dissemination of the immunogenic fractions derived from such soils to accomplish the objective of conferring immunity to unborn babies, as well as newborn babies in accordance with various embodiments of the invention. For purposes of written description and enablement as to how such a commercial system for the ordering and provision of soil samples can be achieved, incorporated herein by this reference in its entirety is U.S. Pat. No. 7,353,194 to Kerker et al. Thus, one of skill in the art will appreciate how to conform and administer a recurring order management system and method for a computer network that is specifically directed to the provision of manure-containing soil samples to achieve the immunity conveying objectives of the present invention. In one embodiment, such a system receives a request for a recurring order for manure-containing soil or services; the system stores the order to facilitate the recurrence of shipping similar such soils in the future in quantities and characteristics (preferably different from prior orders) so the expectant mother receives the samples in a predetermined fashion. Preferably, the order then automatically recurs for a set period of time, correlating with the consumer's desires, but preferably extends from sometime during a pregnancy of the customer and until the newborn baby is around one year to three years old.

Various embodiments of the present invention are distinguished from the prior art in a practical aspect: few expectant mothers—and even fewer new mothers—are willing to administer to themselves—and especially to their newborn babies—anything that requires hooking their tiny baby up to a nebulizer, atomizer or ventilator, nor are they likely to administer a suspension of live bacteria directly into their own noses—and still more unlikely—directly into the small noses of their babies via a nose spray. The practical reality is that unless the administration of the protective agents is relatively easy and an almost unconscious exercise, a new mother and her child will likely avoid extreme treatments, or if they do attempt the same, are likely to cease the required repeated administrations simply due to the difficulties involved in the administrative process. Thus, for example, despite the well-intentioned desire of Bufe et al. to administer to a newborn baby a suspension of an isolated bacteria composition via a "conventional inhaler, nebulizer, atomizer or ventilator" and the admitted need to use such cumbersome devices on such a small, otherwise healthy child at the requisite "regular intervals over a prolonged period"—such regimen involving such administrations to be performed up to "21 times a week, preferably 7 to 14 times a week, for example for up to 10 years" and with the duration of each "administration" being up to 120 minutes, but preferably between 5 to 60 minutes—is simply impractical. The net result of attempting to provide an effective treatment by such a route is destined to fail, as observance of a fairly rigorous administration regimen is required to achieve the desired benefit. Thus, even if the described suspension and/or composition of Bufe, et al. is deemed to be efficacious, the way it is administered renders it ineffective in achieving its objective.

As a practical matter, administration of an effective composition should preferably be in the same fashion as experienced by those residents on a farm where exposure to the protective agents is encountered. Thus, preferably the generation of a stream of airborne agents in an urban environment should closely mimic the manner in which farm residents experience such agents. The mixture of natural manure, soil microorganisms, virus, etc. present in farm environments, and especially those farms that limit the use of antibiotics for their animals, and specifically for their cows, is experienced by individual humans in many ways, simply by walking on, contacting, and living amidst such soil. Thus, to mimic the farm living experience, the provision of farm soil such that an urban dweller experiences a similar exposure to such soil as a farm resident is the preferred way for an expectant mother and later young infant to experience the farm soil. Preferably, administration of effective amounts of farm derived allergens is by making effective amounts of farm soil available such that the immune protective agents present in such soil, including *lactobacillus* species, especially *L. Johnsonii*, are presented to individuals without the need to prepare solutions, water suspensions, isolated bacterial compositions, etc. Preferably farm soil as described herein is provided in an urban dwelling so that the protective agents are permitted, if not encouraged, to be communicated via the air environment. In certain embodiments, the increased dispersion of farm soil ingredients in the urban dwelling environment is achieved by having an air circulating mechanism assist is such dispersion of protective elements. For example, a fan that blows a stream of air across the surface of farm soil in an urban enclosed environment is one of the preferred way to achieve desired increased dispersal of protective agents. By having this air infused farm soil environment, an expectant mother and a new born infant can both experience the protective effects of breathing in farm soil derived agents without the need to undergo some other type of administration, such as via nasal sprays, oral administration, nebulizers, inhalers, topical applications, etc.

In various embodiments of the present invention, the avoidance of antibiotic use with farm animals is preferred so that the *lactobacillus* existing in manure, and thus in farm soil, is of the type that can confer the desired antigenic protection in a human, especially expectant mothers so that such immunity is conferred to their unborn children. Incorporated in its entirety is U.S. Pat. No. 8,420,074 to Rehberger, et al., directed to *Lactobacillus* strains that are useful as direct-fed microbials, as well as US Pat. Publication No. 20140154290 to Peters, for various administrations of compositions, except as specifically contradicted herein; US Patent Publication 20070087020 to O'Connor; 20040115223 to Follansbee; 20050118655 to Weinstock; U.S. Pat. No. 4,568,639 to Weinstock;

Current industry practices to improve health and, more specifically, reduce the levels of coliforms and *E. coli* within the gastrointestinal tract of pigs generally include feeding antibiotics at subtherapeutic levels. However, the practice of feeding antibiotics to livestock has raised concerns about increasing the antibiotic resistance of microbial pathogens in the food supply. Another approach to improving the health of animals is to alter the inhabitants of their gastrointestinal tract. Altering the inhabitants of the gastrointestinal tract of animals has been attempted by feeding direct-fed microbials to animals. The efficacy of single or multiple strains of *Lactobacillus* commonly used in commercial direct-fed microbials has been and continues to be debated. This debate is primarily due to inconsistent performance of previous direct-fed microbials. This inconsistency may be due to the fact that many commercial direct-fed microbials are composed of *Lactobacillus* strains commonly used as silage inoculants or cheese starter cultures. These strains may be effective to inoculate silage or to convert milk into cheese, but have no proven efficacy as direct fed microbials for animal feeding. While the "one strain for all products" approach may be an economical method for the commercial fermentation industry, this does not provide the best strains for each application.

In still other embodiments, bacteria of various strain can supplement the farm soil derived microflora, such as by adding thereto bacteria as described in U.S. Pat. No. 7,862,808 to Isolauri, et al. Thus one aspect of the present invention is directed to the administration of a therapeutically effective amount of a farm soil derived composition in accordance with the present invention to an expectant mother in a manner that confers immunity to her unborn infant, with supplementation of the bacterial species present in such soil in either amount, volume, species state, etc of the microfloa composition. The particular types of bacteria that are most preferred as an added component to farm soil include the following: *Prevotella* and *Ruminococcus, Bifidobacterium infantis, Lactobacillus acidophilus, Bacteroides fragilis, B. longum* bv. *Infantis* isolate UCD272; *B. infantis* BCRC 14602; *B. longum* bv. *Infantis* AY151398.

In yet still other embodiments, certain aspects of the present invention are directed to particular *lactobacillus* strains that have demonstrated antibiotic resistance and that effectively inhibit the growth of harmful pathogenic microorganisms, including for example, microorganisms described in U.S. Pat. No. 8,034,606 to Park, et al., (which is incorporated herein in its entirety) e.g. *Lactobacillus sakei* Probio-65.

Thus, one aspect of the present invention relates to supplementing natively obtained soil samples from Amish farm soil (or the equivalent thereof, e.g. traditional farms that have little if any anti-biotic use) having bovines and other animals resident thereon—with other bacterial and microfloa constituents that are obtained from other sources, such as from biological cultures that have proven to be particularly useful in providing a desired immunogenic response. Such additive soil, when properly handled and disseminated via air-flow mechanisms such that individuals residing at various urban locations are exposed to effective amounts of immunity conferring elements thereof, is a general objective of the present invention, with expectant mothers being a particularly desired population for treatment in accordance with the procedures set forth herein. For example, addition to obtained soil samples from Amish farms with the bacteria species identified in 20080112983 and 20080305089 to Bufe (which are again incorporated in their entireties herein) forms one particular embodiment of the present invention.

In certain embodiments, soil is collected below 0.5 meters at a farm location, and barn dust is avoided. Preferably, there is no homogenization process employed on the sample. Preferably, in most cases, additional water is avoided, and thus, preferably no suspension is made from the soil sample. Preferably, even if an extract is made—e.g. via a suspension in water—smaller molecules are NOT removed from the extract. Preferably, moist or wet soil is collected. Preferably, there is no isolation of one or a few individual species of the bacteria, and thus preferably the bacteria present in the soil sample is not treated in a manner that would result in bacteria being in isolated form. Preferably, there is no fragmentation, and no bacteria-killing step carried out. Preferably, there is no aqueous solution or a hydroalcoholic solution used. Preferably, the bacteria are not derived from a commercial grown culture obtained commercially and grown in culture. Also preferably, there is no use of a drying or lyophilization (freeze drying) of the vital or killed bacteria or of the fragments obtained therefrom.

Dust in certain forms include bioaerosols and consist of endotoxins, bacteria and fungi. They can cause both short-term and long-term health problems such as pneumonia symptoms, asthma symptoms, organic dust toxicity syndrome, and farmer's lung. Farmer's lung is so much more prevalent in winter than any other time of year that some medical doctors define it as a disease of farmers who handle contaminated hay during the winter months. Preferably, no heat sufficient to kill bacteria is employed so as to prevent any significant modification of the soil bacterial mixture that one would otherwise experience on an Amish farm.

Preferably, soil collected on the ground, rather than any material collected at an elevation of above about 2 feet above the ground, such as dust, is employed. Moreover, preferably the soil is not homogenized, nor is it treated to otherwise remove agglomerations, and in particular efforts are exerted to preclude any crushing or digesting such that cells, microorganisms, and spores are preserved.

In certain embodiments, efforts are employed to avoid or limit water and an aqueous solution is not preferred in the preparation of soil for use. Furthermore, preferably no process is employed to remove smaller molecules from and sample or extract.

In certain embodiments, the soil samples collected are tested to determine their content, and preferably those selected include naturally occurring, non-transgenic, isolated bacteria, especially those selected from the group consisting of *Lactococcus* and *Acinetobacter* or fragments thereof or a mixture thereof.

Administration is preferably not via any other way than by natural air-borne dispersal of soil containing aspects deemed effective in conferring immunity to allergic diseases. It is not, therefore, advisable to attempt to administer the soil containing aspects of the immunity stimulating elements by trying to administer in a more conventional oral, nasal, subcutaneously, rectally or vaginally.

The bacteria in the soil collected is believed to be largely harmless as they are ubiquitous in the environment, posing little if any serious adverse effects on physical wellbeing or health. If the bacteria are employed before the occurrence of an allergic or inflammatory disorder, such a disease can be prevented, or the severity of the episode can be alleviated. This is generally referred to as “prevention”.

One aspect of the present invention is to appreciate the developing immune system at a time when, for example, a child's immune system is first developing, such as administration being repeatedly provided to pregnant women, babies and children in the first few years of life. The composition or the medicament is preferably administered to pregnant women, babies or children who, owing to a positive family history, have a distinctly increased risk of developing an allergic disorder. The invention is therefore preferably administered to pregnant women and babies especially in the first year of life.

Disorders which can be prevented in this mild and harmless way or which can be treated in this way are allergic or chronic inflammatory disorders selected from IgE-dependent type I allergies or type IV allergies and chronic inflammatory cutaneous disorders or autoimmune diseases, for example hay fever, food allergies, asthma, neurodermatitis, atopic dermatitis, contact eczema, psoriasis, type 1 and 2 diabetes, multiple sclerosis, collagenoses, rheumatoid arthritis, thyroid disorders such as Hashimoto's thyroiditis and Graves' disease.

In one embodiment, the composition obtained from the Amish farm soil is administered, preferably via having such soil exposed to air flowing over such soil and into the interior of a residential environment where the expectant mother and unborn fetus reside, and/or after the birth of the child, where the newborn baby is exposed to the air that flows over the soil. Thus, the term administered should be understood to include the provision of an effective amount of a composition that is immunologically protective via its ability to charge the native immune system of the individual due to its timely contact with the individual at appropriate times during early human development, such time believed to be relatively limited in duration and literally a narrow window of exposure opportunity for the immune system to properly develop a defense to what later becomes an allergic condition. In certain embodiments, a further administration of certain selected *Lactobacillus* or *Lactococcus* bacteria, preferably isolated strains known to have no substantial adverse effect on physical wellness on health, and in some embodiments is a non-transgenic, isolated composition of particularly desired *Lactobacillus, Lactococcus,* viral and fungal constituents. Such administration is timed to be preferably frequent, such as at least 3 minutes every other day, preferably at least 2 minutes every day, and most preferably for at least about 5 minutes each day for at least 5 out of seven days of a week until the baby is one year old. Preferably, administration is not via oral, injection or nasally sprayed rectal, etc., as the practical aspect of administration to a newborn in such fashion makes it highly undesirable and in any event difficult and impracticable for a mother to do to her small child. In other words, the administration of Amish soil samples via provision of the soil in the residential environment such that an expectant mother and later, a newborn, is easily exposed to the protective aspects derived from the soil blowing or otherwise having its bacterial and viral and fungal constituents presented into the air to make exposure thereto both easy and efficient. Preferably, there is a preference to avoid the use of any type of a conventional inhaler, nebulizer, atomizer or ventilator. While not preferred, certain other embodiments employ a nebulizer, inhaler, atomizer or ventilator as the primary or the secondary source of exposure to the desired protective components included in the Amish soil as otherwise described herein.

One aspect of the present invention is directed to exposing expectant mothers and the born babies of such mothers for their first 12 months outside the womb, to high levels of allergens obtained from selected farm environments, specifically those having bovine manure containing soils rich in specific bacterial families, thus conferring a protective effect against atopy and wheezing in early childhood.

It has long been thought that exposure to perennial indoor allergens contributes to the development of allergic sensitization with subsequent development of wheezing and that indoor allergens contributed to the development of asthma. But the present inventors have found that immunologic protection is afforded by purposeful exposure to urban dwelling expectant mothers—to the compositions as set forth herein—in a manner that confers protection of the mother's child, specifically when the exposure is achieved via a natural air conducting manner such that the pregnant mother is exposed for at least the last 6 months of her pregnancy and the child, once born, is exposed to the same on a regular and periodic basis, e.g. at least a few times each week for at least 5 minutes a time, for the first 12 months of the child's life.

Thus one aspect of the present invention is directed to the exposure to high levels of certain allergens and bacteria during fetal development and for the first 12 months of a child's life to reduce the likelihood that the child will develop wheezing and allergic diseases. Wheezing illnesses affect 35% to 50% of children by the age of 3 years and are a leading cause for outpatient visits and hospitalizations, and wheezing or other signs of atopy during the preschool years is a risk factor for asthma. Because the prevalence and severity of asthma are high in inner cities in the United States, it is especially important to identify risk factors that contribute to the development of allergic sensitization and wheezing in this environment. Farm-related microbial exposures in early life have been linked to protection against allergic diseases but to date, no one has provided a method and device to confer such protection to an urban setting in an effective manner. The timing of allergen exposure is therefore important as only exposures during fetal development and for 12 months of the child's life are believed to be critical for immunologic protection to be achieved. The polysaccharide arabinogalactan is known to have immune modulating effects, reported as increasing immediate immune reactions. Incorporated herein in its entirety is U.S. Pat. No. 5,614,501 to Richards for the disclosures of arabinogalactan containing food for bovines from which manure is particularly desired to be obtained in soil samples for use in the present inventive method and system. Manure from bovine animals, when contained in soil and collected and transported to an urban environment for exposure to an expectant mother, especially when the bovine has fed upon a dietary fiber including a hemicellulose, and more preferably arabinogalactan, is believed to provide a superior immunologic composition as by digesting such arabinogalactan, the bovine increases the amount of beneficial bacteria, such as bifidobacteria, and reduces the amount of putrefactive and pathogenic bacteria, such as *Clostridium*. In certain aspects of the present invention, arabinogalactan is added to collected samples of bovine manure containing soil to enhance the immunologic protections believed to be conferred by exposure to arabinogalactan.

Thus one object of the present invention is to provide a means to reduce the likelihood of a child developing an allergic and/or inflammatory disease. This object is met by a prophylactic antiallergenic composition, comprising manure containing soil that includes bovine manure, and preferably where the bovine has been fed a diet that included at least one arabinogalactan or arabinogalactan protein. The term "arabinogalactan" primarily means the arabinogalactan polysaccharide unit which is part of an arabinogalactan protein or arabinogalactan peptide naturally occurring in e.g. various plants. According to various aspects of the invention, any arabinogalactan can be used, however, preferably the arabinogalactan is one from any grass. One preferred arabinogalactan is from Meadow Foxtail (*Alopecurus pratensis*), timothy grass and timothy grass pollen (*Phleum pratense* L) or Cock's Foot (*Dactylis glomerata*) or Yorkshire Fog (*Holcus lannatus*) or English Raygrass (*Lolium perenne*) or Smooth Meadow grass (*Poa pratense*) or Rye (*Secale cereale*) or grasses from related species. Thus, in a preferred embodiment the feed composition for bovines includes at least one arabinogalactan or arabinogalactan protein, such that the bovine manure includes at least one arabinogalactan and a naturally occurring bacteria of the genus *Lactococcus* or fragments thereof.

In other embodiments, the present invention involves the use of manure containing soils having bacteria of the genus *Lactococcus* as a naturally occurring, non-genetically engineered, particularly non-transgenic microbe. In preferred embodiments, it is believed that the bacteria employed as found naturally on Amish farm soils are harmless for mammal organisms and correspond to natural occurrences of such bacteria. However, to avoid contamination of the selected composition with other microorganisms less harmless than Lactococci, according to certain embodiments of the invention a method for sterilization of the composition can be applied like e.g. using an autoclave, cooking or heating the organisms, use of bactericides, bacteriastatica, fungicides, fungistatica, viricides and/or viristatica, UV rays or use of organic solutions which are toxic for bacteria like e.g. alcohols, particularly ethanol, propanol, isopropanol etc., lyophilisation or sterilization by coldness. Preferably, however, such sterilization is not performed so as to preserve the desired natural components in the manure containing soil that confers the immunologic protection sought to be achieved hereby. Similarly, in preferred embodiments, there is no step of isolation of the naturally occurring ingredients and thus, it is preferred that they not include purified or cultivated (bacteria) and that they not be commercially obtained.

Diseases which can be prevented or treated by employment of the present application are particularly allergic and chronic inflammatory diseases, like IgE-depending Type I allergic diseases or Type IV allergic diseases and chronic inflammatory diseases or autoimmune diseases. Examples therefore are hay fever, food allergy, asthma, urticaria, neurodermitis, atopic dermatitis, contact eczema, psoriasis, diabetes type 1 or 2, multiple sclerosis, rheumatoid arthritis, diseases of the thyroid gland like Hashimoto Thyreoditis and Graves disease.

According to certain embodiments of the present invention, where both manure containing soil and a separate additive including at least one arabinogalactan is employed, the expectant mother is exposed thereto, for at least the last trimester of the fetal gestational period, and continues for a period of at least about 6 months, more preferably 9 months, and most preferably up to 12 months after birth. The composition is suitable for application to expectant mothers for the benefit of their unborn children, as well as for new infants (babies) as it is believed that the method of the invention results in the modification of the infant and such infant's later adult immune system. Preferably, exposure to the various forms of immunologic protective material is limited to the period of gestation of the mother and for the first 12 months of the newborn baby, with the exposure to be limited thereafter to the baby, e.g. stopping or ceasing such exposure after the first year of life. Preferably, application is only via exposure via transmission of the manure/soil compositions in the air of an urban dwelling of an expectant mother using one or more of the devices and methods as described herein, and is not administered via oral, nasal, conjunctival, subcutaneous, intra-articular, intraperitoneal, rectal or a vaginal route.

One aspect of the present invention is directed to providing a method of generating a health-improving indoor air, comprising the step of distributing described compositions to existing urban indoor air, via inclusion in house plant soils, or via existing HVAC systems, or by one of the various devices presented in the figures hereto to provide a prophylactic antiallergenic, i.e. health-improving indoor air that involves the provision of manure/soil from selected farms that do not employ antibiotics and that have bovine animals resident thereon that consume particular grasses, especially those having arabinogalactan, such that the air created by exposure of expectant mothers to the compositions is achieved via the indoor air.

Application routes such as subcutaneous, intra-articular and intra-peritoneal administration routes are unpleasant and painful for mothers and babies and thus, in preferred embodiments the use of even facemasks or a mouthpiece are avoided. Preferably, compositions (as described herein) of the present invention are distributed in the indoor air to generate a health-improving indoor air, thus simulating the healthy air in natural farming environments.

While the preferred method involves the use of soils obtained directly off of the above referenced non-antibiotic using farms, in certain embodiments, a composition may be prepared by combining the aforementioned functional ingredients from natural sources, preferably not from any chemical synthesis. The addition to such farm soils, of an amount of isolated arabinogalactan separated from any further organic (plant or bacterial) material, and included in an indoor air product, is one variant of the present invention, as the naturally obtained soil may be lacking in significant amounts of arabinogalactan for the achievement of desired immunological protective effects. To these extracts naturally occurring, non-pathologic, non-transgenic isolated bacteria, in certain embodiments selected from the group consisting of *Lactococcus* and *Acinetobacter,* are also added, to again enhance the immunological protective aspects meant to be achieved.

One aspect of the present invention relates to not only exposure of the newborn to soil containing bacteria in order to charge the babies immune system, but also to steer the course of the expectant mother's immune system and milk production capabilities so as to generate particular infant protective and immune enhancing compounds. Such compounds, secreted in mother's milk, include those that thwart pathogens, foster a robust immune system and provide inactive enzymes that turn on in the infant gut such that bioactive molecules are clopped out from other milk proteins. While it is known that mother's milk is a combination of fats, proteins and sugars, typically in a ratio of about 1-3-7, such milk also contains a myriad of immune cells, such as macrophages, stems cells for regeneration and a collection of other fat, protein and oligosaccharides (some indigestible) that form a bioactive combination that can protect against infection, ward off inflammation and spur the immune system and organ development of the infant during his/her first year of life.

A preferred bacterial that proliferates on the cocktail of compounds in mother's milk is *Bifidobacterium longum* biovar *infantis* (*B. longum* bv. *Infantis*). This bacterium is believed to enter the infant's intestinal tract in one of several ways, including when the fetus swallows amniotic fluid, when the fetus passes through the vaginal tract in a vaginal birth, and when the infant is provided with mother's milk. While there are hundreds of human milk oligosaccharides (HMOs) the *B. longum* bv. *Infantis* preferentially feast on the same to develop a colony of bacteria in the infant gut, thus leading to further enhancement of the developing immune system of the infant. The HMOs also directly ward off harmful bacteria, such as *Salmonella, Listeria* and *Campylobacter.* HMOs also mimic carbohydrate structures on the infant's gut and thus are believed to swamp the infant's system so that these dangerous bacteria bind to the HMOs rather than to the infant's developing gut, e.g. in a type of competitive defensive mechanism that is known in other natural systems. It is important to have a developed infant immune system that has a sufficient and significant number of *B. longum* bv. *Infantis,* which is correlated with the amount of mother's milk provided—but only if there is a resident and sufficient population of *B. longum* bv. *Infantis* in the first place. This bacterium makes up about 90% of the population of the gut of an infant, which is striking in that only about 3% of the adult gut is inhabited by this bacteria.

It is preferred that administration of antibiotics should be avoided so as not to wipe out the emerging population of *B. longum* bv. *Infantis* in the developing infant gut. Rather than supplement the infant's diet with *B. longum* bv. *Infantis,* as such supplements must typically obtain FDA approval and may suffer from the many problems that are encountered when any supplement is introduced—especially to such a delicate and sensitive system such is an infant's. Thus, it is better to enhance the mother's milk itself by proper exposure of the mother to bacteria that can naturally make it into the mother's milk. However, in certain embodiments, enhancing a mother's milk with additional *Bifidobacterium longum infantis* ATCC 15697=JCM 1222; or alternatively a strain of *Bifidobacterium longum* biovar *infantis* deposited in the Coleccion Espa{acute over (.eta.)}ola de Cultivos Tipo (CECT) under the accession number CECT 7210; or a strain of *Bifidobacterium* (*Bifidobacterium longum infantis* UCC35624; or *Bifidobacterium longum* biovar *infantis* CECT7210; can be done, especially in situations where a mother may not be able to produce milk in sufficient quantity or quality. U.S. Pat. No. 8,197,872 to Mills; US 20100260720; and US 20130059815 is hereby incorporated by this reference. HMOs selectively promote the growth of certain bifidobacteria strains over others, and especially *B. longum* bv. *Infantis,* and their catabolism may result in free monosaccharides in the colonic lumen.

It is believed that due to the co-evolution of humans with various farm animals, including bovines, that exposure to the myriad of bacteria, viruses, and other agents trigger a mother's immune system, thus creating an environment so that a natural and beneficial production of mother's milk rich in *B. longum* bv. *Infantis* is generated and produced for the infant's consumption. Mother's milk further includes glycan, which also contributes to encouraging anti-inflammatory responses. Also included in mother's milk is 2-fucosyllactose, found to be effective in warding off various pathogenic bacteria. The infant gut is not very acidic and without supplementation by mother's milk, is largely devoid of a significant number of enzymes. Inactive enzymes in the mother's milk are thus converted into a natural, active form in the infant's gut. One will appreciate that it is quite possible, using the present invention, that a vast number and array of allergies will be reduced if not prevented, without fully understanding the admittedly complex mechanisms involved in the evolutionary developed systems that exist between farm animals, human mother's and developing infants, all of which are involved in the development of a robust and effective immune system for an infant. But despite the numerous unknowns in the various details of immune system development, the present invention discloses some of the basic fundamental aspects that are required to properly permit the creation of an environment where an expectant mother's immune system is charged with lactobacteria and other organisms derived from farm animals that humans have long cohabited with, such that an infant, via swallowing amniotic fluid of the mother, exposure to such bacteria in the vaginal tract, and also provided with enzymes, HMOs and other compounds in the mother's milk that enhance the beneficial populations of various bacteria, including especially *B. longum* bv. *Infantis,* with such environment providing a rich milieu that encourages the development of an infant's immune system.

In preferred embodiments, one avoids collecting dust from cattle and goat stables, and in particular, collection of material above a height of about 0.3 meters, with collection of material at or above 0.5 meters to be avoided. Preferably, farm soil containing manure of bovine animals is collected inside or within 10 feet of a bovine containing stable and without collecting material in dust form above 0.5 meters in the stable environment. Moreover, while both dry and wet material may be collected for use, preferably moist material is collected and employed as the collection of resident organic materials, bacteria, fungi, etc. is believed to be better represented and preserved therein. In some embodiments, however, while collection of the manure containing soil is preferably performed when such soil is at least somewhat moist, after collection, the soil may be dried to facilitate handling, conveyance, later urban use, etc.

Preferably, one should avoid treating the collected material by various means, such as being later homogenized, for example using a mortar or a mill. Nor preferably should the material be suspended in water or isotonic saline, nor should the collected material be mechanically disintegrated, for example by using a homogenizer or a shaking apparatus, nor should the collected material be separated by centrifugation, dialyzed or lyophilized. Instead, the collected material is preferably maintained in a state similar to that as one would experience the soil on the farm from which it was obtained.

In certain embodiments, the present invention is directed to a method for reducing the occurrence in a child in his or her first year of life of an allergic or chronic inflammatory disorder selected from the group consisting of IGE-dependent type I allergies or to an autoimmune disease to at least one alergen. The method includes administering internasally to the child in its first year of life a composition consisting essentially of a naturally occurring, non-transgenic, isolated *Lactococcus* bacteria strain, administered at least 3 times a week with a dose of between about 2.times.10 (to the ninth) and 3.times.10.sup.9 colony forming unit (CFU) of such bacteria per application. In other embodiments, the dose is up to about 5.times.10.sup.10 to about 6.times.10.sup.10 CFU of bacteria per week. Certain embodiments employ the bacteria *lactococcus lactis,* which may be in the killed state or in a vital state. The dosage for an infant during his/her first year is believed to be about 26 times higher than a dose experimentally applied to mice. It is believed that intranasal administration to an infant (during its first year of life) of a composition of the present invention is more effective than other modes of administration, and thus one aspect of certain embodiments include administering naturally occurring, non-transgenic lactococcus bacteria strain(s)—preferably in certain embodiments being in an isolated state (and/or added as a supplement to the Amish-derived farm soil(s)), so as to achieve the desired stimulation of the infant's immune response. It is believed that other modes of administration, such as subcutaneous, intraperitoneal, oral and intragastric means are not nearly as effective to achieve the desired protective result. Thus, as described herein, intranasal administration, including the breathing of compositions as set forth herein (e.g., the fan distributed Amish-derived farm soils, etc.) through nasal passages, of compositions containing either isolated or naturally obtained mixtures of Amish-soil containing microorganisms, (with certain compositions being enhanced as described herein with particularly selected helminth and *lactobacillus* species), is a preferred method for administrating protective amounts of a composition that is able to trigger the normal development of the infant's immune system. The superior efficacy of intranasal administration of the bacteria (and the other various microorganism components as described herein, such as helminth components) over other routes in allergy and autoimmune disease protection, offers a practical efficacy of the claimed method. Thus, in preferred embodiments, employment of one or more modes of intranasal administration of bacterial strains (and other described combinations that can include helminth components) as set forth herein, especially in an admixture with the other microorganisms, including helminth derived products, the desired stimulation of an infants developing immune system is achieved, leading to the absence of various allergies and autoimmune disease states in later life. While many bacterial strains are believed to be recognized as being effective (as listed herein), especially in combination with the other microorganisms as described herein, certain particular strains that achieve the desired results include: *Lactococcus lactis* G121, which is publicly available from: Ruhr-University Bochum—University Hospital Bergmannsheil, Department of Experimental Pneumology, Burkle-de-la-Camp-Platz 1, 44789 Bochum, Germany. Also included as particularly preferred strains of *lactococcus* bacteria, include *L. lactis, L. lactis cremoris, L. plantarum,* and *L. raffinolactis* (all of such commonly found in food, such as dairy products, with no adverse effects on human health) (see e.g. deposits ATCC 19435; ATCC 19257; ATCC 43199; ATCC 43920). Such strains can be publicly accessed to formulate various combinations of effective compositions that are within the scope of the present invention, and will be available to one of skill in the art with the guidance provided herein.

One aspect of various embodiments of the present invention includes a topical composition that includes certain beneficial bacterial and helminth components, such composition intended to be applied to the skin of a newborn infant within the first day of birth, and preferably within the three hours of birth. It may also be applied to the nursing mother in a fashion that the infant is permitted to ingest such composition and or to have it come into contact with the nasal passages of the infant when the infant, e.g., as the infant is cuddled by the mother. As one of skill in the art will appreciate, one or more of the various bacterial species listed and described herein can be employed in a such a topical composition, whether substantially isolated strains are used or whether certain combinations of the bacterial species are used, alone or in further combination with various helminth components, (with preferably commuted portions of helminth larvae or worms being employed, e.g. such that the portions are not infectious but nevertheless are effective in stimulating immune responses in an infant). The topical compositions will preferably not include anti-bacterial agents and will present a pH environment such that the bacterial species of the composition are killed, but rather, a pH environment is presented so that such selected bacterial species are in a vital state, with the other components of the composition being supportive of such viability of the resident bacteria. One objective of such an aspect of the present invention is to provide a topical composition rich with beneficial bacteria and other microorganism components (such as certain helminth, non-infective—but still allergenic components—that are effective in stimulating and triggering the immune system of an infant), with such composition having significant similarities with respect to microorganism compositions present in the milieu of bacteria and other microorganisms found in Amish-soil. Administration of such a beneficial composition can be done much like the nasal mist administration of flu vaccines, especially in view of the results of how effective nasal administration is with respect to achieving an effective immune response. Thus, in various embodiments, a pharmaceutically acceptable carrier appropriate for mucosal delivery is provided, and especially one with the composition being formulated for mucosal delivery of selected components of the microorganisms as set forth herein, including but not limited to a combination of at least two of the ATCC listed microorganisms herein, in addition to at least one component comprising STH's non-infective, but nevertheless, allergenic compositions.

Soil-transmitted helminthiasis (STH) refers to a group of parasitic diseases in humans caused by intestinal roundworms such as hookworms (*Ancylostoma duodenale* and *Necator americanus*), ascaris (*Ascaris lumbricoides*), and whipworm (*Trichuris trichiura*), collectively called soil-transmitted helminths (STHs), which are transmitted through contaminated soil. It has become the most common parasitic infection of humans worldwide. Helminths is a polyphyletic group of morphologically similar organisms, consisting of members of the following taxa: monogeneans, cestodes (tapeworms), nematodes (roundworms), and trematodes (flukes). Helminths belong to the group of intestinal parasites (the other type of intestinal parasite are the protozoa), where infections by Helminths are responsible for over a million deaths a year. STHs are essentially intestinal parasites and their eggs are liberated along the faeces of infected persons into the soil. *Ascaris* and hookworm eggs become infective as they develop into larvae in soil. Globally more than 1.4 billion people have a soil-transmitted helminth infection and the total annual death toll is as high as 135,000.

In preferred embodiments, helminthes are pulverized so as to obtain their antigenic qualities but sparing humans from infection with intact eggs or larvae. Thus, commutation of the eggs, larvae and the whole organism is believed to be effective in precluding infection, while preserving the allergenic responses desired to trigger the human's immune system. Such pulverized compositions of helminth collections—preferably obtained from Amish-soils, may be employed in various administrative modes as discussed herein, including but not limited to the dispersal of such helminth fragments via the air circulated systems as set forth herein, lotions, creams, topical and nasal applications, etc.

It is believed that helminth-induced immunomodulation is mediated through direct effects on the mammalian immune system. Thus, certain aspects of the present invention are directed to therapeutic ways to administer effective amounts of helminth (fragment)—including compositions as part of a therapeutic strategy for multiple inflammatory diseases including asthma, multiple sclerosis, and inflammatory bowel disease, thus employing fragments of such parasites to influence innate and adaptive immunity. Because Helminth infections can induce shifts in the composition of commensal bacterial communities, one aspect of the present invention involves the triggering of a person's immune system in a manner that modulates a host immune response via commensal bacteria—derived signals, thus modulating lymphocyte responses to infection and antiviral immunity. It is believed that such immunomodulation occurs independently of changes in the microbiota and that coevolution may have resulted in mechanisms that allow helminths to directly regulate host immune responses. Thus, helminth parasites and commensal bacteria colonize a person's intestine and via coevolution, mechanisms have resulted whereby helminthes directly regulate a person's innate immune system and affect antiviral immunity independently of changes in the microbiota.

In one particular embodiment of the present invention, a culture of parasitic flatworm stem cells or echinococcal tapeworms, such as from *Echinococcus multilocularis* or the closely related species *E. granulosus,* is used to produce an "immortal" cell line(s), thus alleviating a need for maintaining complex parasitic life cycles. A stable transgenic parasitic helminths and manipulable cell line is therefore provided to use in the combination of effective microorganisms that together confer an immunomodulation response effective to prevent various long-felt but unsolved autoimmune diseases, such as allergies, asthma, multiple sclerosis, and inflammatory bowel disease, as well as other diseases described herein. Preferably these immortal cell lines are used to produce a fragmented, non-infective composition for administration alone or in concert with Amish-soil derived organisms as described herein.

Helminths are strong activators of T helper cell 2. Helminth infection activates T.sub.H2 cells to release IL-4 and IL-13, both of which ligate the IL-4 receptor (IL-4R) on M2 macrophages. Thus, it is believed that the effects of helminth infection on viral immunity are many and have substantial effects on susceptibility to global microbial pathogens. Thus, one aspect of the present invention relates to the multiple colonization of helminth and microbial organisms to positively affect the proper development of a person's immune system that has for many prior pre-industrialized generations been primed and shaped via natures ubiquitous microorganism population, especially those microorganisms found in the environment of farm animals, especially raised by the Amish, e.g. bovines, where antibiotics have not unduly influenced the otherwise native populations of such microorganisms.

The Amish have the lowest reported prevalence of allergic disease of any population living in a westernized country. But confounding experts in the field, while the Amish have so little allergies or autoimmune diseases, similar traditional communities—known as the Hutterites—conversely have high allergy rates, similar to others in the U.S. Hutterites are Protestants of German descent whose traditional, religious-centered lives have been compared to that of the Amish and Mennonites. But the Hutterites possess a notable distinction: unlike the Amish, they use antibiotics on their cows. The use of antibiotics over the last 50 years parallels the rise in allergic and autoimmune diseases over that same time period. The alteration of the microbiome that humans had previously been exposed to during pregnancy and during the immune system's formative first year of human life, was severely altered by the introduction of agricultural antibiotics being provided to cows. Such antibiotics changed the characteristic population of bacteria in a cow's rumen, and hence, in the cow's manure that human's were traditionally exposed to. The absence of allergies and autoimmune diseases suffered by the Amish is directly tied to the absence of antibiotic use in their farm animals.

The exposure of a newborn to antigens derived from helminthes, and certain *lactobacillus* and viruses, etc. promotes the normal development of the human immune system. The deprivation of such immune stimulatory factors, however well intentioned, has caused the series of recent modern day plaques, including a vast number of allergies and autoimmune diseases. From a developmental biological perspective, there is a temporal window as to when such exposure must be accomplished to properly direct a person's immune system development.

Recent reports reveal that children who acquire four kinds of gut bacteria in the first three months of their lives can be protected from developing asthma, such four bacteria, called FLVR (*Faecalibacterium, Lachnospira, Veillonella,* and *Rothia*). To the present inventors, it is not surprising that these bacteria are all found in the bovine rumen. Moreover, at least three of these bacteria are targeted by commonly used bovine antibiotics, e.g. tylosin, and thus, the removal or reduction of such bacteria from what individuals may have been exposed to years ago, and in particular, bacteria that were more plentiful about 50 years ago, may help explain the correlation with agricultural antibiotic use and the dramatic rise in allergies and autoimmune diseases presently being encountered. Tylosin is a macrolide antibiotic, the properties and production of which are described in U.S. Pat. No. 3,178,341, invented by E. I. Lilly in 1960. The antibiotic has become commercially important and finds extensive use in animal nutrition as a feed additive and as a therapeutic agent in the treatment of mycoplasmosis in poultry and livestock. Tylosin is a bacteriostat feed additive used in veterinary medicine. It has a broad spectrum of activity against Gram-positive organisms and a limited range of Gram-negative organisms. *Lachnospira, Faecalibacterium,* and *Rothia* are all gram positive bacteria, while *Veillonella* is a Gram-negative cocci. Antimicrobial feed additives are used not only for the control and treatment of infectious diseases but also for the enhancement of growth and improvement of feed efficiency. Thus, there has been prodigious use of such drugs over the last 50 years. The effect on the naturally occurring bovine rumen bacterial populations has translated into the incredible increase in the incidences of autoimmune diseases, including allergies, asthma, etc. as listed herein.

In certain embodiments of the present invention, delivery of bacteria is achieved in a manner that comports with where such bacteria are normally located in a person's body. For example, many of the bacteria that confer protection against autoimmune diseases as described herein are normally resident in the human mouth. For instance, one of the FLVR bacteria recently touted as being beneficial in the prevention of disease, namely *Veillonella,* is commonly found in a person's mouth, mostly living on the tongue and saliva. In various embodiments, selected bacteria, such as *Veillonella* is purposefully presented on an oral strip that adheres to the mucosal membrane of a person, preferably around the soft palette region, and thus provides a source of such bacteria for an expectant mother, and therefore to her newborn during the first year of life.

CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to a target sequence in the viral genome. The Cas9 protein cleaves and thereby silences the viral target. In preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing (and incorpoarating 20150252358 to Maeder by this reference).

Spacers in a CRISPR cassette confer immunity against viruses and plasmids containing regions complementary to the spacers and hence, they retain a footprint of interactions between prokaryotes and their viruses in individual strains and ecosystems. The human gut is a rich habitat populated by numerous microorganisms, each having a CRISPR system. To comply with written description and enablement requirements, incorporated herein by the following references are the following patent publications: 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to BRYAN.

In various aspects of the present invention, CRISPR is employed to modify aspects for both bacterial and helminthes gene expression such that undesired normally transcribed proteins are excised or precluded from being expressed, thus precluding the deleterious effects of such proteins. Thus, normally dangerous species of bacteria and helminthes (from a perspective of such bacteria or helminthes causing disease in a human) can be modified so that such undesired effects of bacterial and helminthes infection are disrupted or deleted or lessened in a fashion that still permits the beneficial aspects of bacterial and helminthes proteins to be maintained.

Various embodiments of the present invention combine each of the above referenced four FLVR bacteria and using CRIPR, pathogenic and/or toxic elements are excised to preclude detrimental health issues that would normally be encountered using one or more of such bacteria, while preserving the immune system attributes attained by the presence of such bacteria. Preferably, the CRISPR modified bacteria of the FLVR species are then combined in a formulation suitable for use as a vaginal cream such that a newborn is first exposed to such bacteria when traveling down the birth canal.

In certain embodiments of the present invention, antibiotic resistance of certain bacteria is modulated by employment of CRISPR to insert into the genome of a bacteria antibacterial sensitivity such that it can selectively be killed, if necessary, after it is employed to trigger desired immune responses in a new born or other individual. Thus, the various bacterial and helminthes species mentioned herein that are included in an or added to an Amish-soil may, in certain embodiments, be extracted and modified using CRISPR methods to do one of several things, including adding antibiotic sensitivity to various species so that they can be employed for triggering immune responses of an individual, and then later killed or rendered ineffective by the use of targeted antibiotics or anti-helminthes drugs.

In particular embodiments, directed to a topical composition of a bacterial and/or helminthes containing composition, such composition includes cells that have been transformed by use of CRISPR to delete particular undesired attributes of wild-type species, including the expression of disease causing proteins. Thus, the creams, ointments, etc that may be employed as a vaginal pre-birth composition so that a new born, traveling down the vaginal canal, is exposed to a plurality of beneficial bacteria and/or helminthes proteins and other constituents such that a new born innate immune response is triggered to protect the new born from developing the variety of allergic and autoimmune diseases as described herein.

The use of CRISPR to tailor bacterial and helminthes components to either add desired characteristics and/or to delete known deleterious aspects of such bacteria or helminthes, provides a novel system and method for treating a variety of diseases such that bacteria and helminthes that would normally be considered too dangerous to employ as an agent to treat allergic or autoimmune conditions is now rendered available for such purposes.

In various embodiments, DNA is injected into bacteria to restore antibiotic sensitivity to drug-resistant bacteria, and to also prevent the transfer of genes that create that resistance among bacteria. The CRISPR-CAS system may also be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference.

The microbiome of an individual is disrupted by antibiotics and thus, the employment of CRISPR as a way to bypass common modes of multidrug resistance, while being selective for individual strains, is employed in various embodiments of the present invention to attain the benefits derived by the presence of particular bacteria and helminthes, including the triggering of desired immune development by newborns and other individuals, (e.g. those with multiple sclerosis, etc.). CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Another aspect of certain embodiments include making synthetic CRISPR-containing RNAs that target genes of interest and using them with Cas enzymes. The specificity of CRISPR-Cas systems permits one to design methods to target a single bacterial species so that only essential genes form that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is still ~100 nt long. Cpf1 is apparently directly responsible for cleaving the 43-base cRNAs apart from the primary transcript.

With respect to the cleavage sites on the target DNA, the cut sites are staggered by about 5 bases, thus creating "sticky overhangs" to facilitate gene editing via NHEJ-mediated-ligation of DNA fragments with matching ends. The cut sites are in the 3' end of the protospacer, distal to the 5' end where the PAM is. The cut positions usually follow the 18th base on the protospacer strand and the 23rd base on the complementary strand (the one that pairs to the crRNA). In Cpf1 there is a "seed" region close to the PAM in which single base substitutions completely prevent cleavage activity. Unlike the Cas9 CRISPR target, the cleavage sites and the seed region do not overlap. One advantage of the present invention, as compared to techniques that rely on CRISPR systems to modify mammalian cells, is that the system and method of preferred embodiments are directed to bacterial systems—rather than eukaryotic systems. It is believed that Cpf1 may be better than Cas9 for mediating insertions of DNA, namely because its guide RNA is only 43 bases long, making it feasible to purchase directly synthesized guide RNAs for Cpf1, with or without chemical modifications to enhance stability.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modern word processors, Cas9 can be guided to specific locations within complex genomes by a short RNA search string.

In certain embodiments, various particular bacterial species are focused on to delete or modulate their gene expressions, such species including the following: *Streptococcus; Escherichia coli, Streptococcus pyogenes,* and *Staphylococcus epidermidis*. This prokaryotic viral defense system has become one of the most powerful and versatile platforms for engineering biology.

In various embodiments, the CRISPR-Cas systems is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs. Thus, in many embodiments, CRISPR-Cas systems provide for the selective removal of microorganisms to trigger certain predictable development of the immune system, especially in the context of an expectant mother and her child.

The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

In certain other aspects, particular embodiments of the present invention are directed to the use of CRISPR to excise certain prior infectious adenovirus DNA sequences that are considered responsible for the increased obesity of individuals harboring the same. Reference is made to Kovarik, U.S. Pat. No. 8,585,588, "Method and system for preventing virus-related obesity and obesity related diseases." After determining whether one has been infected with an obesity causing virus, the viral DNA can then be excised via CRISPR to remove the previously inserted DNA, thus effectively reducing if not eliminating the adenovirus gene from the individual. Thereafter, to avoid being infected with such adenovirus again, practice of the method as set forth in U.S. Pat. No. 8,585,588 will lessen, if not prevent, reacquisition of such obesity causing DNA.

Controlling the composition of microbial populations is important in the context of desiring to expose expectant mothers to particular species of bacterial and other micros, helminthes, etc. and especially those that have not been previously exposed to antibiotics, antimicrobial peptides, and lytic bacteriophages. Use of CRISPR-Cas provides a generalized and programmable strategy that can distinguish between closely related microorganisms and allows for fine control over the composition of a microbial population for use in the present invention. Thus, the RNAdirected immune systems in bacteria and archaea called CRISPR-Cas systems is employed in various embodiments of the present invention to selectively and quantitatively remove individual bacterial strains based on sequence information to enable the fine tuning of exposure of desired antigens present in an Amish soil microbial consortia. Thus, such genome targeting using CRISPR-Cas systems allows one to specifically remove individual microbial species and strains, leaving other microes to trigger an infant's immune system in desired ways.

In various embodiments, it is desirable to remove—using CRISPR-Cas systems—particular pathogenic bacteria and/or simply the pathogenic portions of such bacteria—while sparing other desired commensal bacteria, in order to provide exposure to desired immune developing proteins.

In various embodiments, one of skill in the art will appreciate that removal of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

Particular embodiments of the present invention are directed to the employment of four specific bacterial genera—*Lachnospira, Veillonella, Faecalibacterium* and *Rothia*—during the first 100 days of life to address, for example, the severity of the inflammatory response by supplementation with these four genera.

An individual's microbiome includes the collective genomes of all the microorganisms that are part of the body's ecosystem. As stated herein, various autoimmune diseases are capable of being ameliorated by the practice of the present invention, including Crohn's disease. Prior researchers have found that several specific microbes were more prevalent in patients with Crohn's than in their healthy counterparts, while other bugs were less common in Crohn's cases. Addressing this dysbiosis, or imbalance, in the microbial ecosystem is one aspect of the present invention. In certain embodiments, certain microbiota that were known to disappear in the guts of Crohn's cases, are reintroduced, including *Faecalibacterium prausnitzii*, and at the same time, several bacteria that are known to proliferate in Crohn's cases, including those linked to IBD and colorectal cancer, are targeted to remove pathogenic abilities. In particular embodiments, providing a collection of microbes, preferably including, for example a higher than normal (e.g. that is found in any random sampling of Amish soil) amount of Faecali, more preferably *Enterococcus faecalis*, is achieved to expose expectant mothers and infants thereto in order to trigger desired immune system responses. Enhancing the growth and viability of this particular bacterium in the gut—and then use of such modified bacterium to treat individuals with various diseases, such as Crohn's disease and other autoimmune diseases. Similarly, *Faecalibacterium prausnitzii,* which represent more than 5% of the bacteria in the intestine, is encouraged to populate the guts of patients. Such enhanced growth of this bacterium may also be employed to combat certain forms of inflammatory bowel disease. In various embodiments of the present invention, *Enterococcus faecalis* is are subjected to CRISPR-Cas procedures to remove undesired virulence and pathogenicity factors, such as several genes isolated from resistant enterococci (agg, gelE, ace, cy1LLS, esp, cpd, fsrB) which encode virulence factors such as the production of gelatinase and hemolysin, adherence to caco-2 and hep-2 cells, and capacity for biofilm formation. Deletion and removal of certain antibiotic resistance, for example the acquisition of vancomycin resistance by enterococci, is desired also so as to properly and safely employ this bacteria in the present invention. In a particular embodiment, the addition of *E. faecalis* LAB3 1 is employed to trigger desired immune system responses.

On aspect of many embodiments of the present invention include the use of specialized viruses to supply CRISPR/Cas to rid bacteria of antibiotic-resistance plasmids and/or other virulence factors. Virulence factors of Gram-negative anaerobes such as *Prevotella* include, for example, fimbria, hemolysins, adhesions and hemagglutinins. These bacteria commonly produce immunoglobulin-degrading enzymes and some produce tissue-degrading enzymes. Additionally, bacteria of the genus *Prevotella* are often resistant to antibiotics, such as tetracycline, erythromycin, and β-lactam antibiotics. In practice, a *Prevotella*-targeting lambda phage is created that encodes the CRISPR genes plus spacers that target two conserved β lactamases, enzymes that confer resistance to β-lactam antibiotics. Once integrated into the *Prevotella* genome, the phage prevents the transfer of β lactamase-encoding plasmids and can also delete these plasmids from individual bacterial cells. These lambda phage-encoding bacteria then become sensitive to treatment with antibiotics.

Similarly, it is desired to increase the presence in samples provided to urban dwelling expectant mothers of other bacteria, and in particular, *Bacteroides-Prevotella*, bifidobacteria, *Desulfovibrio* spp., *Clostridium clostridiforme,* and *Faecalibacterium prausnitzii*. Avoidance of antibiotics by the expectant mother during the period to which she is exposed to the various Amish soil constituents is desired if not critical in certain embodiments due to the profound changes due to such during antibiotic treatment. In other embodiments, the use of CRISPR-Cas systems is employed to increase butyrate production of these bacteria. For example, *F. prausnitzii*), one of the most abundant species in the colon, is an important producer of butyrate, a major product of carbohydrate fermentation which is implicated in providing protection against colorectal cancer and ulcerative colitis.

Modifying the human genome, made possible by the CRIPSR technique, has its own wonderful upsides and equally daunting downsides. Permanent deletion of genes from the human genome is much more controversial than deletion of bacterial genes. Thus, one desirable aspect of the present invention is directed to the far less controversial modification of gut microbes resident in the human being to promote health and to trigger the desired immune responses as described herein.

CRISPR-Cas can be used on the various identified microbiome constituents to modify gene expression, including cutting of a gene, repress or activate a gene, etc. It can be employed to deliver desired regulators or any protein to a desired place on a geneme of a microbe, thus permitting one to tailor the attributes of the microbiome of an individual to promote the health thereof, including the programmed triggering of particular immune responses in an infant. Because CRISPR-Cas acts before transcription occurs, it is able to be employed to target regulatory and other elements on the DNA of microbes that make up the microbiome. In certain embodiments, CRISPR-Cas is employed to deliver fluorescent markers to certain DNA sequences, thus permitting one to determine whether any particular sample has been treated in accordance with the present invention, thus ensuring, for example, identity of various materials, safety issues, types of enhanced soils, etc. This permits labeling of living cells with a desired color. Still other embodiments of the present invention are directed to the use of stool samples from Amish to transplant to other humans, especially expectant mothers, such that the attributes of the microbiome of the Amish can be enjoyed by both the expectant mother and her child.

Still other embodiments involve the collection of Amish soil and the subsequent use of CRJSPR to remove infectious components (whether bacterial or helminthes in origin)—at least most prominent ones—so as to provide a safer sample for use by urban dwelling residents. So modified poop for use in process.

While a preferred way in which to administer the benefits as described herein is via transmission through the air of beneficial bacterial and helminth derived components, other embodiments rely upon the ability to deliver agents via mucosal adhesive strips, such as described, for example, in U.S. Pat. No. 8,701,671, which is fully incorporated herein by this reference. In such a manner, one objective is to accept the beneficial traits of the microbiome's interaction with the human immune system while avoiding the infectious aspects of bacterial, viral and helminth aspects of such exposure to a human being. Thus, in various embodiments of the present invention, the engineering of communal bacteria with improved properties using a CRISPR/Cas system is employed to provide for the enhancement of health by prevention of allergies and other autoimmune diseases as set forth herein.

Thus, in certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 1 6S ribosomal DNA (rDNA). Preferably the delivery vehicle is a bacteriophage.

As is the case with many inventions, after the disclosure thereof, the invention seems to be pre-ordained. The linking together of what at first would appear to be disparate and unrelated elements congeal into a method and system that reveals the simplicity of the solution once the inventor shows how the various parts can be arranged to address the problem. Here, the problem is long felt and unsolved: the terrible and costly epidemics of diseases that have arisen in the past 50 years of human history throughout the world— except for the tantalizing and small pockets of individuals seemingly immune to such diseases, such their insulated society is largely spared such a fate: the Amish. It is not their genetics. It is not what food they consume. It is not their alleged aversion to flu shots. It is something that is subtle only when one fails to appreciate the entire environment that the Amish live in and the various agents to which they are exposed throughout their lives, but most importantly, at a critical stage of human development—the gestation of a child and its first year of life on earth.

The microbes that humans have been exposed to for thousands of years have now been altered by mankind's intervention with antibiotics—specifically agricultural antibiotics that have been touted (See tylosin's patent praising its use in U.S. Pat. No. 3,178,341) as being particularly beneficial in the agricultural industry. Such antibiotics were even used by many that lived lives otherwise almost and seemingly identical to the Amish—e.g. the Hutterites. But the lure of higher profits and the seemingly health benefits to farm animals through the administration of agricultural antibiotics was viewed as a small trespass into the modern world that did not broadly violate the Hutterite's traditional aversion to modern agents and medicines, etc. But the last 50 years has shown that the use of agricultural antibiotics by the Hutterites has resulted in profound changes to human health. Such a seemingly minor change in the way farm animals, and especially cows, were raised, has changed the very character of the microbiome to which humans have traditionally been exposed. The use of agricultural antibiotics has now spread worldwide and is truly ubiquitous across the earth. The ecological experiment that is the Amish society reveals, perhaps as an isolated but nonetheless most valuable instance, of how such a global change in the world's raising of animals has adversely and unexpectantly affected the health of millions of human beings.

One aspect of various embodiments of the present invention include the use of CRISPR-Cas, a new technology that was only recently discovered as the bacterial world's immune system. Various aspects of the present invention involve the recognition that this system can be employed to benefit human health by modifying the bacterial and other microbe communities that humans have long been exposed to in a fashion such that the beneficial aspects of such microbes can be preserved, while the disadvantageous aspects can be "cut out" of the microbe d\DNA—rather than attempting to change or modify the DNA of a human.

The recent appreciation of the important of gut microbes—as well as other microbes that humans are exposed to (e.g., skin, vaginal, etc.) to human health, has lead others to focus on probiotics and food diets, etc. While these clearly play a part in human health, such a focus fails to address the above referenced plague of diseases.

The thought of exposing human's to otherwise odious material, such as manure, and especially animal manure and soil,—literally "dirt" (from which "dirty" and all its negative connotations emanate)—is a classic case of teaching away from an invention. That one would purposefully expose humans to potentially—if not known—pathogenic containing substances—and especially to the most vulnerable of our society: expectant mothers and newborns—borders on the absurd—until one appreciates that such exposure may be the thing that actually saves a child from suffering terrible autoimmune diseases. With the advent of CRISPR-Cas— and its employment with particular microbes that can be readily located and found in Amish soil, the ability to lessen, if not eliminate entirely, the above referenced fear that pathogenic agents would be purposefully employed—is addressed. Thus, one aspect of the present invention is the tying together of the seemingly disparate threads of Amish living and the absence of autoimmune diseases; the content of microbes in Amish soil—as they exist due to the refrain of the Amish in employing traditional antibiotics that have been employed in animal husbandry for the last 50 years (which tellingly tracks the same period of the rise of autoimmune disease around the world); the use of CRISPR-Cas to focus on bacterial and microbe DNA—rather than human DNA modifications to achieve the objective of enhancing human health; together form a twisted and strong cord that supports the many aspects of the present invention.

There exist various concerns about how CRISPR-Cas systems and method will be employed with respect to attempting to improve human health through and using a technology that cuts sections of DNA out of a genome, effecting permanent changes to the human DNA. Indeed, many in the scientific community are considering whether a moratorium on the use of this powerful and yet simple technology should be implemented until such time as all the risks involved can be better assessed. In the context of the present invention, however, this particular issue is either absent or of lesser importance due to one focus of many embodiments being relegated to the modification of DNA of the microbe genomes, rather than the human genome. Thus, the present invention is one way in which the human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system. Moreover, the use of such a DNA modification system for microbes, but not for the direct deletion of genes from a human, and the use of such a system prior to the exposure of a human to such modified microbes, has not previously been done, especially with the added step of modifying select microbes having immune beneficial attributes—and especially using modified microbes that one would otherwise have considered to be pathogenic, and thus, undesirable as an exposure agent to benefit some of the most cherished and vulnerable individuals in our society: expectant mothers and the unborn. The selection of particular microbes that would be subject to processing using CRISPR-Cas is rendered understandable to one of skill in the art as the ability to discern what microbes are in any particular sample of Amish soil is well within the skill of the art. After assessing what particular microbes are present in a sample, the appropriate processing of such microbes using CRISPR-Cas to delete undesired genetic elements or features is relatively straightforward (especially in view of the guidance provided herein and in conjunction with the references incorporated herein by reference.) Thus, as perhaps one of the main potential downsides of simply taking Amish soil and transplanting it to an urban environment is that the bacteria and other microbes therein may be pathogenic, the ability to take the contents of Amish soil and modify the constituents thereof using the CRISPR-Cas system provides a way to ameliorate such concern such that a safer mixture of microbes is transported and delivered to such urban environments. In comparison, the use of antibiotics can be viewed as an too all-encompassing technique to destroy pathogenic microbes entirely—and by doing so, potentially precluding the beneficial aspects to be derived from an individual's immune system being exposed to various antigenic elements that would otherwise be presented by such pathogenic microbes. What is needed is to retain the immune triggering elements of Amish soil without the downsides of being exposed to pathogenic features of potentially dangerous organisms. The CRISPR-Cas system provides such a way to achieve this objective.

The human microbiome (HM) of the GI tract contains the largest reservoir of microbes in humans, containing about 1014 microorganisms from at least 1000 distinct microbial species, and outnumbering human somatic cells by about 100 to 1. The total HM has been estimated to encode about $4\times10^6$ genes versus the ~26,600 genes of the human host, so the quantity of HM genes outnumbers host genes in the order of about 150 to 1. Of the 55 bacterial divisions currently identified, only two are prominent in mammalian GI-tract microbiota, including the anaerobic Bacteroidetes (~48%) and Firmicutes (~51%). Human mitochondria originated from bacteria via endosymbiotic relationships from very early in the evolutionary history of eukaryotes.

As noted previously, it has been observed, in analyzing people's gut bacteria by their occupation, that those who had regular contact with livestock, such as farmers and their wives, had bacterial communities dominated by *Prevotella*, a type of bacteria that is also abundant in the gut microbiota of cattle and sheep. *Prevotella* are among the most numerous microbes culturable from the rumen and hind gut of cattle and sheep. Percentages vary but *Prevotella* is often the most common bacterial genus in the cattle. While certain aspects of particular embodiments are directed to the *Prevotella* genus, others are more focused on particular species within such genus, namely *P. intermedia*.

The present inventors contend that the contributions of microbes to multiple aspects of human physiology and neurobiology in health and disease have up until now not been fully appreciated.

There is evidence that the human microbiome, including not only gut microbiome, but also the human oral microbiome, is involved in the progression of Alzheimer's disease (AD). AD is the most common form of dementia in the western world. There is no cure available for this devastating neurodegenerative disorder, now the leading cause of cognitive and behavioral impairment in industrialized societies. The cause of AD is unknown. While about 5% of all AD cases have a genetic or familial cause, the vast majority of all AD cases (~95%) are of sporadic origin. The present inventors believe that AD has an infectious origin and that with such a recognition, various treatment protocols can be implemented to thwart what has been a very long felt but unsolved problem. It is submitted that pathogenic microbes are the main agents with respect to the acquisition of AD, and that AD is not, as some have thought, a genetic disorder. Results from recent genome-wide association studies indicate that a significant portion of AD-relevant gene signals are not located within gene coding regions. There exist Amish communities that are so seldom victimized by Alzheimer's that many wrongly concluded they must be genetically protected. The sporadic form of late-onset AD constitutes approximately 98% of all AD cases. While there exist certain genetic susceptibility traits for AD, it is believed that such focus on genetic factors has obscured the true cause of the disease and diverted resources from where they should be spent in order to combat AD. Apart from the two main hallmarks, amyloid-beta and neurofibrillary tangles, inflammation is a characteristic feature of AD neuropathology. It is notable that virtually all AD patients die, not as a direct consequence of AD itself, but rather from pneumonia. The accumulation of amyloid-beta (Aβ) peptides in the inflammatory degeneration of neurons in the human central nervous system (CNS) drives Alzheimer's disease pathogenesis. Aβ acts as an antimicrobial peptide (AMP), part of the brain's immune defense mechanism that targets Gram-negative and Gram-positive bacteria, enveloped viruses and protozoans. Aβ peptide accretion is the result of an imbalance between Aβ peptide production and clearance. The microbes of the human microbiome naturally secrete large amounts of amyloid. The clearance of Aβ peptides is critically impaired by deficits in the microglial plasma-membrane enriched triggering receptor expressed in microglial/myeloid-2 cells (TREM2).

Important periodontal pathogens related to AD are *Fusobacterium nucleatum* and *Prevotella intermedia*. Clinical and epidemiological studies reveal that the loss of teeth is associated with poor memory. In the cascade of events causing AD, oral microorganisms play a significant role, particularly anaerobic bacteria such as *Prevotella* spp. and, *Fusobacterium*. The recent observation of microbiome-derived small non-coding RNA (sncRNA) and micro RNA (miRNA) translocation and signaling across endothelial barriers, between cells and tissues, indicates that human neurobiology is impacted by the actions of HM-mediated sncRNA or miRNA trafficking.

One aspect of the present invention is directed to the reduction of cerebral Ab amyloids by modifying the microbiome, and in particular the oral microbiota of an individual, by exposing such individuals to particular bacteria, especially those bacteria that have been genetically modified via the CRISPR-Cas system, such that otherwise pathogenic characteristics of such microbes are deleted, but such microbes are otherwise relatively intact such that the native character of the genus and species of oral bacteria for a particular person is preserved.

The microbiome of a person seems to be individual and resistant to change. The microbiome of a person varies depending upon what tissues are involved. For example, the intestinal microbiome plays a critical role in mucosal inflammation, but the stool microbiome poorly correlates with colonization of the mucosa. Thus it is essential to obtain the particular species of microbes in the microbiome colonizing the particular tissue of a person, rather than other species that may be present in other tissues of such person. US pat. Publication No. 20150190435 to Henn is incorporated herein by this reference. Tissues of all humans are colonized by microbes in the gastrointestinal (GI) tract, on the skin, and in other epithelial and tissue niches such as the oral cavity, eye surface and vagina.

One aspect of the present invention is directed towards the modification of an individual's microbiome, and in particular the oral microbiome of an individual, such that via microbial alterations, the development of the Alzheimer's disease pathology and the development of neurodegenerative diseases is substantially reduced if not precluded. Specifically, the bacterial genes targeted by using CRISPR-Cas include those responsible for a myriad of secretory products known to be extremely powerful pro-inflammatory and innate-immune activators. Collecting samples of a person's oral microbiome and then selecting for various pathogenic bacteria form such sample, processing such pathogenic bacteria using the CRISPR-Cas system to remove undesired pathogenic or other identified characteristics of the bacteria, and returning such modified bacteria to the oral cavity of such person, is one method for deterring, treating and/or combating AD, as well as other inflammation origin diseases. In various embodiments, pre-treating such individual (after obtaining the bacteria to be modified) with antibiotics such that the altered microbes, when they are returned to the oral cavity, have a competitive advantage over any resident bacteria that may still reside in the oral cavity.

Fecal microbiota transplantation (FMT) is the introduction of a fecal suspension derived from a healthy donor into the gastrointestinal (GI) tract of a diseased individual. While not a new therapeutic concept it has, over the last few years, experienced a significant growth in interest, with an evolving methodology and clinical indications largely due to two factors: (1) the global *Clostridium difficile* infection (CDI) epidemic and (2) a growing appreciation of the complexity of the GI microbiome and its active role in health and disease. FMT is no longer considered an "alternative," last-resort medical practice but, rather, is now gaining mainstream acceptance as a valuable, although still poorly understood, therapy with biological plausibility.

CDI is primarily a GI dysbiosis with *Clostridium difficile* overgrowth. CDI has traditionally yet counterintuitively been treated with antibiotics such as metronidazole, vancomycin, and, more recently, fidaxomicin or rifaximin. However, antibiotic therapy results in further microbiota damage and in recurrence rates of at least 20%, which rise with each subsequent CDI episode. Furthermore, antibiotics do not correct the abnormal microbiome but, rather, potentiate the problem. In view of the description provided herein, sufficient guidance is provided to one of skill in the art in order to tailor any particular regimen required to implement a given method to address similar microbiome based diseases, such as Crohn's Disease, IBD, Irritable Bowel Syndrome, diabetes mellitus, obesity, multiple sclerosis, Parkinson's disease, chronic fatigue syndrome, rheumatoid arthritis, sacroileitis, halitosis, acne, insomnia, and major depression, Autism spectrum disorder, etc.

Yet other aspects of other embodiments of the present invention are directed to fecal transplantation from healthy Amish individuals to others who have various diseases or in need of preventative treatments to thwart disease. While in the past, fecal material from donors of close relatives has been used, the present inventive embodiments contemplate and involve the transplantation of fecal matter from healthy Amish individuals to non-related, non-family individuals. Careful screening of the feces is performed to insure that contagious diseases are not conveyed. Thus, in various embodiments, the present invention also relates to a composition comprising anaerobically cultivated intestinal microbiota that constitutes a functional seeding culture for re-establishing normality of a disturbed human microbiota and gastrointestinal functions and the use of such composition for the prevention and treatment of disease, including but not limited to various autoimmune diseases, as well as to Alzheimer's Disease. In various embodiments, a micro-ecological system of strictly anaerobically re-cultivated human intestinal microbiota obtained by anaerobic cultivation of a stool sample in a cultivation medium is employed to promote the proliferation of the anaerobic bacteria, including at least two of the following Phyla: Bacteroidetes, Firmicutes, Proteobacteria and Actinobacteria, and more preferably at least two of the following: *Faecalibacterium, Lachnospira, Veillonella, Rothia; Lactobacillus johnsonii* and *Prevotella*. In yet other embodiments of the present invention, stool samples of healthy Amish individuals is obtained, the microorganism content thereof identified, and components thereof extracted for use with other individuals in need of a transplant of a healthy microbiome in their colon or gut. "Stool banking" is gaining popularity in some sectors, and thus, one of skill in the art will appreciate the basic techniques involved in obtaining and conveying fecal material to another to achieve desired health benefits therefrom. One of skill in the art of fecal transplant will understand how best to refine the microbiota product employed, the administration methodologies used, including timing, doses, etc.

In many embodiments, Amish donors are identified and selected to create a pool of tested healthy donors and preliminary screens are performed to avoid complications between a donor and a recipient's shared genetic or environmental susceptibilities. In one embodiment, donor stool is preferably delivered obtained within a few hours of passage to undergo (1) dilution, generally with normal saline, (2) homogenization with a blender to achieve a liquid slurry, and then (3) filtration to remove particulate matter to facilitate administration. Even more preferably, however, highly filtered human microbiota is mixed with a cryoprotectant and then frozen for storage until required for use. This processing removes the fecal smell and reduces the volume of the filtrate. While various modes of administration may be employed, including naso-duodenal, transcolonoscopic, or enema based, the later is preferred as bowel preparation therefore assists in "flushing out" the abnormal host microbiota and facilitates "implantation" of the donor microbiota. Enema administration is also effective, inexpensive, and safe. In certain embodiments, Amish healthy volunteers donate fecal samples and such donor stools are utilized after they have been filtered to remove all but the microbiota and a substantial amount of water content via lyophilization (freeze-drying) with the resulting component (largely faecal microbiota) being a powder containing the full spectrum of gastrointestinal microbiota (FSM). This would be encapsulated and could be immediately administered as an oral medication. Such an optimized product would do away with transport issues, the discomfort associated with faecal enema infusions, and minimize the 'lck' factor of handling human stool.

Human gastrointestinal bacteria often share their environment with parasitic worms, allowing physical and physiological interaction between the two groups. Such associations affect host health as well as the bacterial and helminth populations. The interaction between the microbiome and parasitic helminths in humans offers the potential to improve health by manipulating the microbiome. Previously, supplementation with various nutritional compounds has been found to increase the abundance of potentially beneficial gut commensal bacteria. Thus, nutritional microbiome manipulation to produce an environment which may decrease malnutrition associated with helminth infection and/or aid host recovery is one aspect of the present invention. In other embodiments, the present invention provides a method and system for preventing Alzheimer's disease in a manner that deals with the causative agents of the disease—and thus focuses on steps that can be taken decades in advance of the symptoms of Alzheimer's disease first appearing. For the first time, the present invention provides a way for individuals to adopt positive behaviors, techniques and compositions that can thwart the progression of Alzheimer's disease. The present invention is directed, from a more general perspective, on the human microbiome and its relationship to chronic diseases that have, to date, been unresolved and misunderstood. The relationship between the oral microbiome and Alzheimer's disease is focused on to determine effective method and systems to prevent the initiation and the progression of the disease.

Humans have co-evolved with micro-organisms and have a symbiotic or mutualistic relationship with their resident microbiome. As at other body surfaces, the mouth has a diverse microbiota that grows on oral surfaces as structurally and functionally organized biofilms. The oral microbiota is natural and provides important benefits to the host, including immunological priming, down-regulation of excessive pro-inflammatory responses, regulation of gastrointestinal and cardiovascular systems, and colonization by exogenous microbes. On occasions, this symbiotic relationship breaks down, and previously minor components of the microbiota outcompete beneficial bacteria, thereby increasing the risk of disease.

Researchers have analyzed people's gut bacteria by their occupation and have found that those who had regular contact with livestock, such as farmers and their wives, had bacterial communities dominated by *Prevotella*, a type of bacteria that is also abundant in the gut microbiota of cattle and sheep. The anaerobic black-pigmented *Prevotella intermedia* is a Gram-negative rod-shaped bacterium whose habitat is the strictly anaerobic environments of the gastrointestinal tract and gingival crevice. *P. intermedia* plays an important role in the onset and subsequent development of the polymicrobial periodontal diseases. It is known that *Prevotella intermedia* adaptation to oxidative stress influences the virulence of the microorganism.

There is increasing evidence that the reach of gut microbes extends beyond the intestine, affecting systemic processes, such as metabolism and organ functions of brain, cardiovascular system, liver, and others. Several metabolomic studies have identified hundreds of compounds in blood that are specifically derived or dependent on the presence of gut microbes.

Researchers have theorized for some time that mitochondria—the organelles that produce energy in human cells—play a role in aging and disease. There is evidence that people who experience less destructive aging have genetically different mitochondria when compared to the general population. Furthermore, mitochondrial lineages described by patterns of common genetic variants (or "haplogroups") have also been shown to be associated with increased longevity in different populations.

One aspect to the mystery of Alzheimer's disease etiopathogenesis lies in the relative absence of Alzheimer's disease in certain Amish communities. The prevalence of *Prevotella* in the oral cavity of the Amish, the production of nitric oxide by this bacteria, and the reduction of spirochetes in the brains of the Amish, all present evidence as to an effective avenue for therapeutic intervention in Alzheimer's disease prevention and/or progression.

One aspect of the present invention is directed to the pathology of Alzheimer's disease as it relates to inflammation. Reactive microglia and astrocytes adjacent to Aβ plaques is a common observation in the brain of Alzheimer's disease sufferers. It is thought that activated glia is at first beneficial for degrading Aβ plaques. Chronic inflammation, however, leads to the production of several cytokines that have been demonstrated to exacerbate other Alzheimer's disease pathologies. An increased infectious burden and higher serum levels of inflammatory cytokines have been associated with serum Aβ markers in Alzheimer's disease patients. Chronic infections caused by these pathogens have been shown to result in cardio-cerebral vascular disorders, which subsequently promote the development of Alzheimer's disease. These studies provide supporting evidence that accumulative infections are associated with Alzheimer's disease and supports the role of infection and inflammation in the etiopathogenesis of Alzheimer's disease. Certain aspects of the present invention are directed to a reduction in the risk of Alzheimer's disease through a combination of antibiotic and anti-inflammatory therapy.

The fact that Alzheimer's disease usually develops in later life suggested that a slow-acting unconventional infectious agent acquired at an early age and requiring decades to become active may be involved in its etiology. Spirochetes are such unconventional infectious agents.

Spirochetes have been found in about 90% of Alzheimer's patients, while these bacteria were virtually absent in the brains of healthy age-matched controls. Once a spirochete infection begins in the brain, it causes disease by forming plaques or masses along the cerebral cortex. In Alzheimer's disease, the brain's normal defenses become dysfunctional as the macrophages (microglia) become trapped and then attacked within the core of the spirochete plaque. With immune dysfunction setting in, the spirochete infection intensifies involving more and more brain cells. Damaged brain cells produce amyloid-beta protein as an adaptive response to the infection. As an adaptive response to infectious organisms, like invading spirochetes, amyloid-beta protein is produced, which we now know has anti-bacterial properties, amyloid-beta deposits grow and begin to affect brain cell connections and communication highways. With damaged connections and communication highways, dementia symptoms begin and gradually worsen.

Spirochetes is also a commonly isolated microorganism in moderate to severe periodontitis. These organisms are also detected in patients with Alzheimer's disease, suggesting that periodontopathic bacteria can invade the brain by systemic circulation as well as peripheral nerve pathways. The presence of oral bacteria in systemic circulation is usually expected when heavy bacterial plaques are present. AβP, the main component of amyloid plaques, which is instrumental in the pathogenesis of Alzheimer's disease.

Alzheimer's disease is characterized by the salient inflammatory features, microglial activation, and increased levels of proinflammatory cytokines which contribute to the inflammatory status of the central nervous system. The present inventors believe that, like other spirochetes based diseases, prevention and treatment decades in advance of the appearance of symptoms is at the heart of the Alzheimer's disease mystery. For example, in various ways, Alzheimer's disease shares certain similarities with syphilis. *Treponema pallidum* (*T. pallidum*) persists in the syphilitic brain, which sustains chronic infection and inflammation and causes slowly progressive dementia. Dementia develops years or decades following the primary syphilitic infection. Historic observations and illustrations published in the first half of the 20th Century indeed confirm that the pathological hallmarks, which define Alzheimer's disease, are also present in syphilitic dementia. Cortical spirochetal colonies are made up by innumerable tightly spiraled *Treponema pallidum* spirochetes, which are morphologically indistinguishable from senile plaques, using conventional light microscopy. Local brain amyloidosis also occurs in general paresis and, as in Alzheimer's disease, corresponds to amyloid beta. Thus, chronic spirochetal infections can cause dementia and support a causal relationship between various spirochetal infections and Alzheimer's disease. They also indicate that local invasion of the brain by these helically shaped bacteria reproduce the filamentous pathology characteristic of Alzheimer's disease. Chronic infection by spirochetes, and co-infection with other bacteria, is therefore involved in the etiology of Alzheimer's disease. The similarities of the clinical and pathological manifestations of syphilis and Lyme disease are well documented. Lyme disease, like Alzheimer's disease, involves the creation of plaques in brain tissue. Thus, one aspect of the present invention is to adopt a similar treatment regimen with respect to Alzheimer's disease as has been found to be effective with syphilis and Lyme disease. Syphilis is easy to treat with a penicillin, one of the most widely used antibiotics. People who are allergic to penicillin may be treated with a different oral antibiotic, such as doxycycline, azithromycin, or ceftriaxone. Like syphilis, however, the damage already done by Alzheimer's disease cannot be reversed. It is thus imperative that early diagnosis be followed up with an appropriate treatment plan to avoid the dire consequences of Alzheimer's disease progression.

There is compelling evidence that treponemes, spiral-shaped, are involved in the etiology of several chronic diseases, including chronic periodontitis. Treponemes are members of the normal oral microbiota of healthy individuals, albeit in very low numbers. Treponemes are members of the Spirochaetes phylum, a clade now believed to be distinct from both Gram-positive and Gram-negative bacteria, that is believed to have undergone extensive horizontal gene transfer with Archae and possibly with eukaryotic organisms. Chronic periodontitis is a polymicrobial disease, and co-infection of *Treponema denticola* with other periodontal pathogens can enhance alveolar bone resorption. The bacterium has a suite of molecular determinants that enable it to cause tissue damage and subvert the host immune response. The human oral cavity harbors more than 60 different *Treponema* species, previously considered to be commensal spirochetes, but now revealed to be predominant and invasive periodontal pathogens. Spirochetes frequently co-infect with other bacteria and viruses.

When considering the virulence characteristics of *T. denticola*, it is imperative to understand that it is part of a pathogenic bacterial consortium, and its interactions with other bacterial species are important for disease pathology. The bacterial composition of subgingival plaque in individuals with chronic periodontitis often find *P. gingivalis* and *T. denticola* and *T. forsythia* together.

Uncontrolled inflammation of the periodontal area may arise when complex microbial communities transition from a commensal to a pathogenic entity. Communication among constituent species leads to polymicrobial synergy between metabolically compatible organisms that acquire functional specialization within the developing community. Keystone pathogens, even at low abundance, elevate community virulence, and the resulting dysbiotic community targets specific aspects of host immunity to further disable immune surveillance while promoting an overall inflammatory response. Inflammophilic organisms benefit from proteinaceous substrates derived from inflammatory tissue breakdown. Inflammation and dysbiosis reinforce each other, and the escalating environmental changes further select for a pathobiotic community.

According to various aspects of the present invention, one critical appreciation relates to the inventors' contention that bacterial infections are at the heart of many of today's chronic diseases. For example, it is believed that periodontal disease is a risk factor for cardiovascular disease and stroke, as well as a host of other diseases mentioned herein, including Alzheimer's disease, IBD, Crohn's Disease, etc. Because periodontal disease is a modifiable risk factor that can be prevented and treated—the long felt but unsolved treatments for various chronic diseases can also be prevented and treated. Thus, employing a combination of a restorative microbiome approach and an antimicrobial approach, provides for the implementation of treatment that is specifically designed to improve a person's periodontal condition so as to reduce and/or delay future chronic disease, with Alzheimer's disease being one of many. It is believed that one of the reasons such an approach has not earlier been adopted is that when it comes to dental health, there exists several centuries of dental teaching that states that periodontal disease results from a "dirty mouth." Thus, suggesting the use of microbes in the oral cavity to alleviate disease may appear to many as being counterintuitive and a teaching away from long held beliefs and practices.

There are two main forms of periodontal disease: gingivitis and periodontitis. Both are pathologic periodontal inflammatory processes that are the result of an accumulation of dental plaque. The most common is the plaque-induced gingival disease called gingivitis, which is a reversible form of periodontal disease. The other form of periodontal disease is periodontitis, a destructive, irreversible, chronic inflammatory process due to dental plaque, which results in atrophy or loss of the underlying bone and connective tissue support around the teeth. Periodontitis is the most common chronic inflammatory disease known to mankind.

The present inventors believe that effective management of periodontitis is a key to the prevention of Alzheimer's disease, as periodontitis is both treatable and preventable. Thus, oral health is directly related to brain health and with purposeful exposure to certain bacteria species, such as in certain embodiments, Prevotella, the benefits of decreased periodontitis, and thus, the reduction in the emergence of Alzheimer's disease, can be achieved. Prevention of Alzheimer's disease through the use of microbiome products is believed to be one of the best ways to avoid the prevalence of Alzheimer's disease and the public expenses related to its management.

Periodontitis is a common oral infection associated with the gram negative anaerobic bacteria. Periodontitis is an inflammatory disease caused by a microbial biofilm, characterized by periodontal pocket formation, attachment loss and loss of supporting alveolar bone. Periodontally compromised teeth lose function and may have to be extracted, which often requires costly prosthetic rehabilitations. In industrialized countries, approximately 50% of the adult population suffers from moderate or severe periodontitis. Once a periodontal pocket forms and becomes colonized by bacteria, the pathologic situation becomes irreversible.

Periodontitis can be marked as a "low-grade systemic disease" by release of proinflammatory cytokines into systemic circulation and elevation of C-reactive protein (CRP). Dental plaque is unlike any other bacterial ecosystem. Plaque is divided into two distinct types based on the relationship of the plaque to the gingival margin, i.e., supragingival plaque and subgingival plaque. The subgingival plaque harbors an anaerobic gram-negative flora has been associated with Periodontitis.

Although bacteria are involved in periodontal infections, it is not the scenario of a typical infection, as the offending bacteria generally remain outside the body, attached to the tooth. When gum disease reaches a bleeding stage, the bacterial components of the plaque changes and there is an increase in various species, including Prevotella species, which have nutritional requirements derived from the host, such nutrients becoming available as a result of the tissue inflammation and bleeding.

While there are over 500 species of microbial species that are believed to be primary etiologic agents for periodontal disease, only a relatively small number most frequently associated with active periodontal disease, including gram negative, anaerobic pathogens: Porphyromonas gingivalis, Tanneralla denticola, Tanneralla forsythia; Fusobacterium nucleatum, Prevotella intermedia, Prevotella nigrescens, Peptostreptococcus micros, Campylobacter rectus, Centruroides gracilis, Campylobacter showae, Eubacterium nodatum, and Streptococcus constellatus. While only a limited number of gram-negative anaerobes are significantly associated with periodontal disease, the prevailing treatment philosophy remains unchanged as the standard of care in clinical dentistry is supported by a well established economic infrastructure of clinical periodontology. Thus, various embodiments of the present invention are focused on the more refined selection of an appropriate drug to employ to combat particular gram negative, anaerobic pathogens.

Current treatment for periodontitis involves removal of all bacteria from the subgingival pockets. Removal of subgingival plaque by current treatment methods is temporary, since the subgingival packet may be re-colonized after cleaning by organisms from the supragingival reservoir. For individuals suffering periodontal disease, current practice also involves the use of antimicrobial agents that are typically chosen to kill as many bacterial types as possible, often employing broad-spectrum agents such as tetracycline, amoxicillin and metronidazole, and often leading to the overuse of these agents. While use of antimicrobial agents plays a part in various embodiments of the present invention, such use is more nuanced and the destruction of beneficial bacteria in the oral cavity is either prevented or reestablishment of such bacteria is fostered so as to maintain a healthy oral microbiome that can prevent periodontal disease, and thus also prevent the onset of Alzheimer's disease. The uncritical use of antibiotics could increase bacterial resistances. One goal of the present invention is to preserve the maintenance of an ecologically balanced biodiversity of the microflora within the oral cavity as it is crucial not only to the oral health but also to the general health of the individual, especially in avoiding Alzheimer's disease.

Surprisingly, clinicians have been advised that they do not really have to test for what microbe might be involved in periodontitis, and instead may simply use antibiotics on an empirical basis to see how they might work. Thus, one aspect of the present invention is to halt such indiscriminate use of antibiotics—and to have the clinician carefully evaluate the presence of specific gram positive anaerobic bacteria that cause periodontistis. Indeed, current practice for the treatment of chronic periodontitis includes a recommendation to use more than one antibiotic with different antibacterial spectra under the misguided belief that a broad diversity of periopathogens must be killed, including anaerobic, microaerophilic, and aerobic bacteria, both Gram negative and Gram positive. One aspect of the present invention is to target particular gram negative organisms, specifically not including other organisms, such as A. Actinomycetemcomitans, as the use of antibiotics against this organism is believed to hinder, rather than promote, the objective of establishing a healthy microbiome that prevents Alzheimer's disease.

The progress in finding treatments for periodontal disease has been hindered in that there has been no consensus as to whether an anaerobic or microaerophilic infection is involved. Only recently have studies shown that A. actinomycetemcomitans is not, as was previously assumed, an important periodontopathogen in major periodontal diseases.

A broad based antibiotic therapy as part of an early treatment regimen in patients diagnosed with Alzheimer's disease, without an appreciation of the wider beneficial aspects of the oral microbiome—could lead to a worsening of Alzheimer's disease, rather than a treatment for it. Indeed, in various embodiments of the present invention, there is a fostering of the establishment of Prevoletta bacteria, which would be killed by indiscriminate use of antibiotics.

In various embodiments, one aspect of the present invention is directed to therapies to treat or prevent the onset of periodontal disease, which in some embodiments that target agents that inhibit the adherence of P. gingivalis to supragingival plaque, such as can be included in mouth rinses and toothpaste formulations, so that they may be easily and non-invasively administered. *P. gingivalis* gains systemic exposure through damage to gingival tissues. Therefore, limiting the *P. gingivalis* adherence to supragingival plaque in the oral cavity has a dramatic effect on systemic diseases, including atherosclerosis and Alzheimer's disease.

In preferred embodiments, the prevention of the growth of particular pathogenic organisms is achieved without destruction of other helpful organisms that inhabit the oral cavity. In certain embodiments, agents are employed to prevent particular biofilms, such as *P. gingivalis* biofilms, to establish an oral microbiome environment that will halt the progression of Alzheimer's disease. Incorporated herein by this reference are the following US patents and patent publication nos.: 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie is also incorporated herein by this reference in its entirety to provide a background and method of populating a subject's gastrointestinal tract with a diverse and useful selection of microbiota in order to alter a dysbiosis. The inclusion within this specification of reference to published documents is not to be taken to be an admission that any one or more of those documents, nor the disclosure of any one or more of those documents, is part of the common general knowledge.

Alzheimer's disease was thought to be a disorder related to synthesis and decline in the degradation of AβP. There is recent and compelling evidence that the Aβ, however, is not simply a misfolded protein that accumulates in the brain, but is instead a protein with physiological roles that responds to several pathological contexts. The pathological process of Alzheimer's disease is thought to begin long before the diagnosis of dementia is made and thus, an appropriate targeted treatment should start early in order to prevent dementia.

Periodontal disease is an inflammatory disease in which the inflammatory response, followed by the acquired immune response, drives the pathogenesis of periodontal tissue destruction. Periodontal pathogens, which are more or less universally present in low numbers, use inflammation to provide an environment to foster their growth. While for a long time it was thought that bacteria was the factor that linked periodontal disease to other diseases in the body, more recent research demonstrates that inflammation may be responsible for the association. One aspect of the present invention is directed to the appreciation that in preventing and treating inflammation involved in periodontitis (and the resultant increase in host-derived, tissue-destructive enzymes, e.g., collagenase plus other MMPs), it will help with the management of other chronic inflammatory conditions, including Alzheimer's disease. Collagen degradation can be inhibited, for example by using TIMP proteins (tissue inhibitors of metalloproteinases). To reduce potential degradation of polypeptides, certain tripeptides may be employed as collagenase inhibitors, as well as other collagenase inhibitors, e.g. such as paquinimod, and those one of skill in the art will appreciate can be employed for the present purposes, see e.g., U.S. Pat. Nos. 4,687,841 and 4,720,486 to Spilburg, et al; US patent publication no. 20070207955 to Tanihara; all incorporated herein by this reference).

The foundational characteristics of all inflammatory diseases is the up-regulation of cytokines, prostaglandins, MMPs (i.e. host derived, tissue-destructive matrix metalloproteinases), reactive oxygen species, etc. A major event in the link between local periodontitis and relevant systemic/medical conditions is the release, from the inflamed periodontal tissues of inflammatory mediators into the bloodstream, which subsequently travel to the liver. Once inflammatory mediators are present in the blood (i.e. derived from the inflamed gingiva), the liver is stimulated to produce acute phase proteins, which are diagnostic markers and mediators of inflammatory disease; one being C-reactive protein or CRP. To add insult to injury, LDL (low density lipoprotein) cholesterol, when oxidized by the inflammatory response, then forms a chemical reaction with CRP. The end result is a complex of oxidized LDL combined with CRP, which is taken up by macrophages in the atheroma and these macrophages differentiate into foam cells, found in lipid-laden plaques in the arteries and that are associated with increased risk of heart attack and stroke. The foam cells, in turn, release MMP's, such as MMP-8, also known as collagenase. Collagenase's primary function is to break-down collagen. A collagen rich protective cap that encapsulates atherosclerotic plaque is thus destroyed by collagenase, often leading to a thrombosis, followed by stroke or a heart attack. Thus, while a principal focus of the present invention is on the prevention of Alzheimer's disease, one of skill in the art will appreciate the various other important diseases' that may also be addressed via the guidance provided in the present specification, and such other aspects should be understood as also being a part of the present invention.

While the human body is continually destroying old collagen, followed by a renewal process of normal turnover, in chronic inflammatory disease, collagenases, particularly MMP-8, become excessive and the normal repair process is halted. The inflammatory mediators (cytokines, prostaglandin, MMPs) present with oral inflammation, flow into the blood bi-directionally from the gingiva into the circulation, resulting in systemic inflammation. Thus, unless there is a cessation of the inflammatory response, treatment is rendered difficult, if not impossible.

Slowing down the breakdown of collagen and/or inhibiting the production of collagenase is thus one aspect of the present invention and is one way in which to prevent the progression of Alzheimer's disease.

It is known that tetracyclines, a class of drugs that had previously been recognized only as antibiotics, were unexpectedly found to block collagenase in mammals. This lead to the development of a formulation of doxycycline that inhibits collagenase (MMP-8) and other MMPs at a blood level so low that it would NOT perform as an antibiotic known under the trade name, of Periostat®. Low dose or subantimicrobial dose doxycycline is the first systemically administered collagenase inhibitor drug approved by the U.S. FDA. In particular embodiments of the present invention, a topical and locally acting collagenase inhibitor agent, similar to doxycycline, is employed to treat periodontitis, which will act to prevent the progression of Alzheimer's disease. In one embodiment, an individual at risk of further developing periodontitis is administered doxycycline plus methotrexate (MTX), preferably a low dose (about 20 mg) of doxycycline twice daily with MTX.

One aspect of the present invention is to provide antimicrobial agents formulated into oral care products to augment mechanical plaque control. A delicate balance is needed, however, to control the oral microbiota at levels compatible with health, without killing beneficial bacteria and losing the key benefits delivered by these resident microbes. In certain embodiments, laser therapy is employed to kill bacteria in the gum pockets around teeth. One of ordinary skill in the art will appreciate the many tools and techniques involved in such procedures.

In particular embodiments of the present invention, an oral strip, preferably mucoadhesive in nature, is employed to apply the locally acting collagenase inhibitor agent. After applying such strip to the oral cavity, it releases the drug slowly as it is dissolved, so that the drug concentration in saliva exists for an extended time and maintains the desired inhibitory concentration. Use of the strip overcomes certain problems with conventional formulations of doxycycline hydrochloride, including undesired gastrointestinal reactions that produce systemic toxicity, and further eliminates complications arising from the use of drug infused chips, which are inserted into periodontal pockets as well as other resorbable gel compositions, which provide for controlled-release of doxycycline for approximately one week. As Periostat® requires twice daily dosing and raises concerns about patient compliance, the strips of the present invention are believed to be superior and highly beneficial in terms of compliance and effectiveness, without overdosing of drugs in a manner that may cause problems stemming from the long-term administration of antibiotics and consequential reduction or elimination of healthy biotic flora, such as intestinal flora, which can lead to the production of antibiotic resistance organisms or the overgrowth of yeast and fungi. Thus, the strips of the present invention provide a unique way to achieve the benefit of anti-collagen destructive enzymes while avoiding other undesired antibacterial effects.

One aspect of the present invention is directed to the maintenance of a population of *Prevoletta* bacteria in the oral cavity that is similar to populations found in healthy Amish individuals where Alzheimer's disease was a rarity. Amish individuals were found to have elevated levels of *Prevotella* in their oral cavity as compared with other individuals. *Prevotella* is known to produce nitric oxide. Nitric oxide (NO) is known to participate in the complex mechanism of tissue injury as a major mediator of inflammatory processes and apoptosis. NO has potent antimicrobial properties and is an important cellular signaling molecule. NO is a free radical with an unpaired electron. Although the earliest studies in the field suggested that NO is a strictly pro-inflammatory macrophage product, it is clear from the current literature that, in fact, NO is made by numerous cell types and is often anti-inflammatory. Much of this dichotomy can be explained by the particular responses of given cells involved in the inflammatory response, but another variable involves the complex chemistry in which NO can participate.

Nitric oxide is a ubiquitous intercellular messenger molecule with important cardiovascular, neurological, and immune functions. Nitric oxide is a short-lived, reactive free radical that participates in a variety of reactions and in small controlled concentrations in the body, it acts as a physiological and pathophysiological mediator and it plays an important role in biological systems. The assessment of the stable end products of NO, nitrite and nitrate (NOx), is commonly used as a measure of the NO production in biological fluids. The production of nitric oxide (NO) represents another mechanism of pathogen destruction in activated neutrophils. Production of NO or expression of inducible NO synthase (iNOS) by peripheral neutrophils or in gingival tissues is associated with periodontal disease. The massive presence of neutrophils and their enhanced activity at sites of periodontal disease have sparked debate as to whether neutrophils are responsible for the destruction of periodontal tissues or whether they play protective roles in controlling pathogenic bacteria involved in periodontal disease. Neutrophils from periodontitis patients produced significantly lower levels of NO levels when compared to neutrophils from healthy subjects. Low NO levels were produced by neutrophils from chronic periodontitis patients. So the presence of NO seems to be desired in avoiding periodontitis. *Prevoletta* is associated with increased NO production and thus, *Prevoletta*—while also associated with periodontitis, is oddly beneficial to individuals. The recruitment of neutrophils and other leukocytes in the periodontal pocket is an important feature of the inflammatory process in periodontal disease. Neutrophils play an important role in periodontitis by producing nitric oxide (NO) and antimicrobial peptides, molecules with microbicidal activity via oxygen-dependent and -independent mechanisms, respectively. The use of nitric oxide to disperse biofilms may be employed to improve infectious disease treatments. The use of low levels of NO to exploit its signaling properties to induce dispersal represents an unprecedented and promising strategy for the control of biofilms in clinical contexts.

*Prevotella* is also well-known as a preventative agent for the bovine disease of rumen acidosis. Rumen acidosis greatly affects milk production of cattle by disrupting the typical digestive processes of the stomach. This leads to an increased susceptibility to other pathogenic forces which also affect the health of food provided from the cattle. Communities of vaginal microbes change during pregnancy in preparation for birth, delivering beneficial microbes to the newborn. At the time of delivery, the vagina is dominated by a pair of bacterial species, *Lactobacillus* and *Prevotella*.

Periodontal diseases are chronic inflammatory infections associated with gram-negative bacteria which stimulate macrophages to generate NO. *Prevotella intermedia* has conventionally been considered to be one of the causative pathogens of periodontal disease. The increased population of such bacteria in healthy Amish individuals, however, coupled with the scarcity of Alzheimer's disease in the Amish population, presents a classic case where one of ordinary skill in the art of periodontitis treatment, would not promote the use of *Prevoletta*.

*Prevotella*, previously classified in the genus *Bacteroides*, is a genus of an obligate anaerobic gram-negative rod-shape bacterium. Although they generally have a limited ability to ferment amino acid and require heroin and menadione to grow, *Prevotella* is a versatile genus which has been observed in various niches, such as oral cavity, upper respiratory tract, urogenital tract, rumen and human feces. *Prevotella intermedia* ATCC 25611 is a strain isolated from empyema.

Chronic inflammation is characterized by a proliferation of fibroblasts and formation of blood vessels (angiogenesis), as well as an influx of chronic inflammatory cells, namely granulocytes (neutrophils, eosinophils, and basophils), lymphocytes, plasma cells and macrophages. Nearly two decades ago, the production of nitrogen oxides was associated with inflammation. The metabolic pathway known as the Larginine: NO pathway is the main source for the production of NO in mammalian cells by a group of enzymes known as the nitric oxide synthases (NOS). The enzyme primarily responsible for the roles of NO in inflammatory processes is the inducible NOS (iNOS; NOS2; or type II NOS), which is not typically expressed in resting cells and must first be induced by certain cytokines or microbial products.

In recent years, NO has emerged as a major mediator of inflammation. As might be expected from such a pleiotropic molecule, there are contradictory reports in the literature concerning its role as an anti-inflammatory or proinflammatory agent. The inconsistencies reported probably are due to the multiple cellular actions of this molecule, the level and site of NO production, and the redox milieu into which it is released. Little evidence of an association between salivary NO and periodontitis in the general population has been reported.

The dichotomous role of NO in inflammation, often referred to as the NO paradox, is based mainly on the conflicting data showing the effects of NOS inhibitors of varying selectivity in different animal models. The physiological and pathological functions of NO are diverse and often contradictory. NO acts as a useful endogenous free-radical scavenger. NO may provide a chemical barrier to cytotoxic free radicals. NO may have a considerable protective effect on cellular viability and can act as an antioxidant protecting cells from oxidant-induced damage and preventing endothelial apoptosis. Low NO concentrations contribute to endothelial cell survival and high NO levels induce the apoptosis of endothelial cell. Any assessment of the role of NO in human disease must take into account the dual role of NO.

Many of the regulatory and physiological functions of NO can be considered as protective or "anti-inflammatory," and are mainly related to NO produced by the other isoforms of NOS. Other data exists, however, that iNOS expression is found in an increasing number of human disorders, for example, nitric oxide is crucial in the pathogenesis of septic shock. It is believed that certain microorganisms have developed means for suppressing the expression and/or activity of iNOS, perhaps by co-opting the host's own regulatory machinery. Viewed from this perspective, the balance between induction and suppression of iNOS may underlie much of the physiology and pathology of inflammation. Nonspecific inhibition of iNOS also has been reported to be detrimental, rather than beneficial. Release of NO has been reported in inflammatory responses initiated by microbial products or autoimmune reactions. The effects of NO on specific immunity is under investigation. Most of the existing data suggest that NO suppresses, rather than enhances, lymphocyte activation and proliferation. One possible explanation for these often contradictory results is that iNOS inhibition is detrimental to the host during priming of pathogenic T-cell responses in the periphery, but largely protective at the site of disease. It appears that NO plays an important role in the pathogenesis of chronic inflammation. Nitric oxide stimulates TNF-_production bysynoviocytes and its catabolic effects on chondrocyte function promote the degradation of articular cartilage implicated in certain rheumatic diseases. Studies indicate that NO is at least partly responsible for IL-1-induced suppression of glycosaminoglycan and collagen synthesis. In human chondrocytes, IL-18 has been identified as a cytokine that regulates chondrocyte responses and contributes to cartilage destruction through stimulation of the expression of several genes, including iNOS, inducible COX, IL-6, and stromelysin. Although most experimental findings suggest that the actions of NO in the cartilage are detrimental, there is also evidence for protective functions of NO. In a recent study, intravenous inoculation with *S. aureus* induced significantly increased clinical severity of septic arthritis, with attendant septicemia in iNOS deficient mice, compared with similarly infected heterozygous or wild-type mice. This was associated with enhanced production of IFN-_and TNF-_in vivo and in vitro, which indicated a shift towards increased production of Th1-type cytokines. Apart from antimicrobial activity, other beneficial effects of NO include stimulation of proteoglycan synthesis during certain conditions, participation in wound healing, and stimulation of collagen production. Furthermore, NO also is reported to promote mucosal integrity. The isoform nonselective NOS inhibitor L-NAME worsens acute edematous and necrotizing pancreatitis; whereas, NO donors reduces pancreatic injury. Indeed, there is increasing evidence that iNOS is beneficial, rather than detrimental, for resolving intestinal inflammation. Evidence for the dual roles of inducible NO in modulating gastrointestinal mucosal defense and injury is presented in a recent review. In endothelial cells, NOS prevents apoptosis; whereas, it induces apoptosis in smooth muscle cells. The presence of iNOS in atherosclerotic plaques suggests a role for NO in atherosclerosis but its exact role is still unknown. One of the primary functions of the inflammatory response is to heal wounded tissue. Healing commences soon after injury, while acute inflammation in still in full swing. Interestingly, the cytokine most associated with wound healing, TGF-_1, may be the most potent suppressor of iNOS. The recent finding that exposure to NO of cells, which express latent TGF-_1, could lead to the activation of this cytokine. This raises the intriguing suggestion that one of the roles of iNOS in wound healing is to modulate TGF-_1. Most importantly, these findings suggest caution with the use of iNOS inhibitors in settings that require appropriate wound healing.

It is now clear that NO cannot be rigidly catalogued as either an anti-inflammatory or a proinflammatory molecule, but it can be considered a true inflammatory mediator. Inducible, high-level NO production mediates a number of inflammatory and infectious diseases by acting both as a direct effector and as a regulator of other effector pathways.

Thus, while in a preferred embodiment, the production by Prevoletta present in a person's mouth is adjusted to mimic the levels observed in healthy Amish individuals, in certain embodiments, e.g. where other factors indicate that excessive, and thus detrimental levels of NO are being produced, one aspect of the present invention is to address the cytotoxic and damaging actions of NO/RNOS without interfering with essential protective functions. Besides selectively inhibiting iNOS, a number of other therapeutic strategies are conceivable in order to alleviate the deleterious effects of excessive NO formation. These alternative therapies involve scavenging of NO/RNOS, and/or inhibition of metabolic pathways triggered by these molecules. The advantage of preserving the beneficial effects of iNOS also needs to be considered when implementing any therapeutic approach. The identification of the roles of NO and of the cells that produce it, as well as the more complete elucidation of the mechanisms that regulate its cellular production in inflammation, will help in the development of therapeutic applications for both acute and chronic inflammatory diseases. Mitochondria preserved some key features of prokaryote synthesis, demonstrating the evolutionary basis to the NO synthesizing prokaryote world.

In particular embodiments, a strip is provided with an effective amount of Azithromycin, which has been found to be effective against anaerobes and gram-negative bacilli. The provision of an oral strip enables such drug to be contacted directly with the sites of inflammation. Still other strips contain an effective amount of metronidazole, which targets obligate anaerobes. In preferred embodiments, ciprofloxacin and other similar drugs that target facultative anaerobes—*Staphylococcus, Corynebacterium,* enteric GNRs, etc. are not employed. The use of strips as described herein is a local delivery method to administer antibiotics and offers a novel approach to the management of periodontal "localized" infections. The primary advantage is that smaller doses of topical agents can be delivered inside the pocket, avoiding the side effects of systemic antibacterial agents, while increasing the exposure of target microorganisms to higher concentrations and therefore more therapeutic levels of the medication.

Another approach to antimicrobial therapy in the control of infection associated with periodontitis is the concept of full mouth disinfection. The procedure consists of full mouth debridement and the brushing of the tongue with chlorhexidine gel and then the mouth is rinsed with chlorhexidine solution so that periodontal pockets are irrigated with chlorhexidine solution. Chlorhexidine rinses are preferred and continued for several weeks to aid healing and augment plaque control. Systemic administration of doxycycline with full mouth disinfection is designed to result in better improvement of periodontal parameters and elimination/suppression of putative periodontal pathogens. Repopulation of the mouth with beneficial bacteria, and preferably those found in healthy Amish individuals, is believed to be the most effective way to maintain oral health in a manner that will prevent later Alzheimer's disease.

Periodontitis is basically a result of inflammation caused due to wide array of pathogenic microorganism. These microorganisms release numerous proteolytic enzymes, resulting in destruction of soft and hard tissues supporting the teeth. Release of LPSs from the gram negative bacteria results in the expression of proinflammatory factors/cytokines like IL-1α and -1β, IL-6, TNF-α, prostanoids, MMP, and by the host tissue cells (neutrophils and monocytes); ultimately paving way to more destruction of periodontal tissues. Hence, host response plays a role of diabolical "dual role" leading to self-destruction, due to the exaggerated expression of tissue proteolytic enzymes. Protease or peptidase is one of the major virulence factors of *Prevotella intermedia*. Besides its role in degrading the host tissue, proteolysis is also an important part of the signaling pathway involved in various pathologies including inflammatory diseases.

Antimicrobials have been used extensively as growth promoters in agricultural animal production, but the specific mechanism of action for them has not yet been determined. Tylosin administration has been found to decrease the proportion of bacteria in the phyla Bacteroidetes, of which *Prevotella* is a member. Despite widespread use of antibiotics for the treatment of life-threatening infections and for research on the role of commensal microbiota, our understanding of their effects on the host is still very limited. Several studies have demonstrated that tetracyclines, the antibiotics most intensively used in livestock and that are also widely applied in biomedical research, interrupt mitochondrial proteostasis and physiology in animals ranging from round worms, fruit flies, and mice to human cell lines.

Prophylactic low-dose antibiotics administered to livestock populations result in an increase in the rates of growth and weight gain, prompting their widespread use as agents to promote growth in commercial animal herds. Although some of this effect is likely due to changes in the gut microbiome, some believe that these effects result from a low-level increase in the release of mitochondrial ROS. Low levels of mitochondrial ROS are essential for cellular proliferation, differentiation, and metabolic adaptation.

In particular embodiments, the use of CRISPR systems to target virulence factors of bacteria is employed to enable the maintenance and destruction of such populations when desired. For example, some of the virulence factors that may be targeted include the following: Gingipain; Capsular polysaccharide; fimbriae; etc. In various embodiments, *Prevotella intermedia* ATCC 25611 and/or *Prevotella*—345885718 *Prevotella* sp. C561 are employed in the present invention, especially in embodiments that employ CRISPR systems to reduce the virulence factors thereof. While antibiotic therapy is non-discriminatory in its action, the use of CRISPR systems permits one to fine tune the selective elimination of particular microbes. One survival mechanism of

*Prevotella* cells is the possession of natural antibiotic resistant genes, which prevent extermination. Modification of *Prevotella* using a CRISPR-system, provides a way to render *Prevotella* susceptible to antibiotics, thus permitting its regulation. Having said this, certain antibiotics found useful in treating *Prevotella* include metronidazole, amoxycillin/clavulanate, ureidopenicilins, carbapenems, cephalosporins, clindamycin, and chloramphenicol.

In one embodiment, an antibacterial rinse is employed, such as that described in U.S. Pat. No. 8,496,914 to Bonfiglio, and such method comprises rinsing with an antibacterial oral rinse formulation for a period of time immediately prior to engaging in oral hygiene activities. After effectively killing a majority of *Prevotella* in a person's mouth, the person reestablishes a population of *Prevotella* in their mouth by swishing their mouth with a solution containing *Prevotella* bacteria that have been modified as described herein. In certain embodiments, virulence factors that are targeted include proteins involved in host cell attachment and invasion (e.g., fimbriae and adhesins), cytotoxicity (e.g., haemolysins and toxins), iron-acquisition (e.g., siderophores) and evasion or disruption of host-cell defences (e.g., capsule). Genes encoding these factors have been shown to be linked to plasmids and the distinct chromosomal regions that are termed pathogenicity islands.

In various embodiments of the present invention, bacterial DNA is altered from pathogenic to non-pathogenic using various methods known to those of skill in the art. One such method is the employment of a CRISPR-Cas to introduce a mutation to the bacterial genome, and/or to specific genes encoding for membrane or secretory products, and/or other genes that regulate virulence genes. Interference with the expression or efficacy of various pathogenic characteristics of certain bacteria, such as by affecting particular virulence factors possessed by bacteria, viruses, fungi, and protozoa, including but not limited to immunoglobulin (Ig) proteases, capsules, endotoxins, mobile genetic elements, plasmids, and bacteriophages. Specifically, and to provide representative examples, virulence factors for *Staphylococcus aureus* include hyaluronidase, protease, coagulase, lipases, deoxyribonucleases and enterotoxins. Examples for *Streptococcus pyogenes* are M protein, lipoteichoic acid, hyaluronic acid capsule, destructive enzymes (including streptokinase, streptodornase, and hyaluronidase), and exotoxins, including streptolysin. Examples for *Listeria monocytogenes* include internalin A, internalin B, lysteriolysin O, and actA. Examples for *Yersinia pestis* include an altered form of lipopolysaccharide, and YopE and YopJ pathogenicity. Other virulence factors include factors required for biofilm formation (e.g. sortases) and integrins (e.g. beta-1 ad3). In addition to bacteria, helminthes possess similar factors, such as neutrophil inhibitory factor. Thus, one aspect of the present invention is to employ CRISPR systems to achieve interference with specific virulence factors or with regulatory mechanisms that control the expression of multiple virulence factors, and in such a manner, provide a way for such microbes to positively affect a person's immune system without attendant pathogenicity. In certain embodiments this may take the form of employing CRISPR loci to control, for example, the dissemination of antibiotic resistance in bacterial species, such as staphylococci. For example, CRISPR targeting of *Streptococcus pneumoniae* capsule genes, essential for pneumococcal infection, provides a way to thwart bacteria virulence and pathogenic effects. In certain embodiments, the CRISPR-Cas system is effectively employed as a regulator of gene expression and in such manner, provides a way for bacteria, especially pathogenic bacteria, instead of being eliminated by the use of broad based antibiotics, are transformed into non-pathogenic microorganisms, thus maintaining the positive attributes that they provide in a microbiome of an individual.

Typical applications and administration techniques of antibiotics may not eliminate oral spirochetes as in other spirochetal diseases, such as syphilis. Typical administration of antibiotics is believed to only force the spirochetes into a more protected spore form, thus triggering a survival strategy that allows them to resurface at a later date. One aspect of the present invention is directed to effective administration of an antibiotic that will effectively reduce the population of spirochetal microbes that are causative of Alzheimer's disease via the direct application of antibiotics via oral mucosal adhesive strips, and preferably in an environment where the pH of saliva is adjusted to be below 6.5, which is believed to be a level where spirochetal activity is often observed. Most spirochetes are free-living and anaerobic. Therefore, they flourish in an environment that supports this condition. Acidosis (an acidic condition of the body) which reduces available oxygen to the cells can contribute to the increased presence of this bacteria. Certain embodiments of the present invention are directed to the purposeful infection of a person with spirochetes bacteria that have been treated with a CRISPR-system to render them sensitive to antibiotics, thus making it possible to later kill them.

Recent reports have documented that infectious agents also occur in atherosclerosis, cardio- and cerebrovascular disorders, diabetes mellitus, chronic lung and inflammatory bowel diseases, and various neurological and neuropsychiatric disorders. As the focus of the present disclosure is admittedly on Alzheimer's disease, one of skill in the art will nevertheless appreciate that there is a wide over-lap of the fundamental mechanisms involved in the treatment of Alzheimer's disease as described herein and that the teachings herein find application in one or more of the above listed conditions, and thus, this specification is intended to and should be considered as encompassing the treatment of such conditions. For example, Autism spectrum disorder (ASD) affects a significant number of individuals worldwide with the prevalence continuing to grow. It is becoming clear that a large subgroup of individuals with ASD demonstrate abnormalities in mitochondrial function. As described herein, given the ties between microbes and mitochondria, the use of particular antibiotics to kill microbes must also be considered as to the affect such drugs have on mitochondria and the impacts on various disease states such as ASD.

For example, many host tissues, including the endothelial lining of blood vessels, produce hsp60 as they respond to certain stressors like high blood pressure. It is postulated that an autoimmune mechanism in which the host responds to foreign hsp60, such as bacterial hsp, could be important in the development of an undesired formation of a lipid-containing material on the endothelial lining of arteries. It has been found that inflamed gingival tissues of periodontal patients exhibit a positive antibody response to both the hsp produced by oral bacteria (e.g. *Porphyromonas gingivalis*) and to human hsp60. This reveals that oral bacteria not only play a role in periodontal disease, but also are involved in diseases related to humoral immune mechanisms. For example, antibodies against the hsps of *P. gingivalis* react with human hsps exposed on the endothelium and produce cellular damage.

Similarly, the destruction caused by the inflammatory pathway when a transient infection becomes chronic demonstrates that the treatments employed to address a transient infection can literally turn the body against itself when the inflammation becomes chronic. The role of chronic inflammation, and in particular periodontitis and its association with many of today's most prevalent diseases, such as cardiovascular disease, Alzheimers, cancers, diabetes and autoimmune disorders, is at the heart of the various embodiments of the present invention. Coronary Artery Disease remains the number one cause of death in the world. While traditional risk factors partially account for the development of Coronary Artery Disease, chronic inflammation plays a role in the development and propagation of this disease.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

DETAILED DESCRIPTION OF PREFERRED EMBODIMENTS OF THE INVENTION

Figure 1:
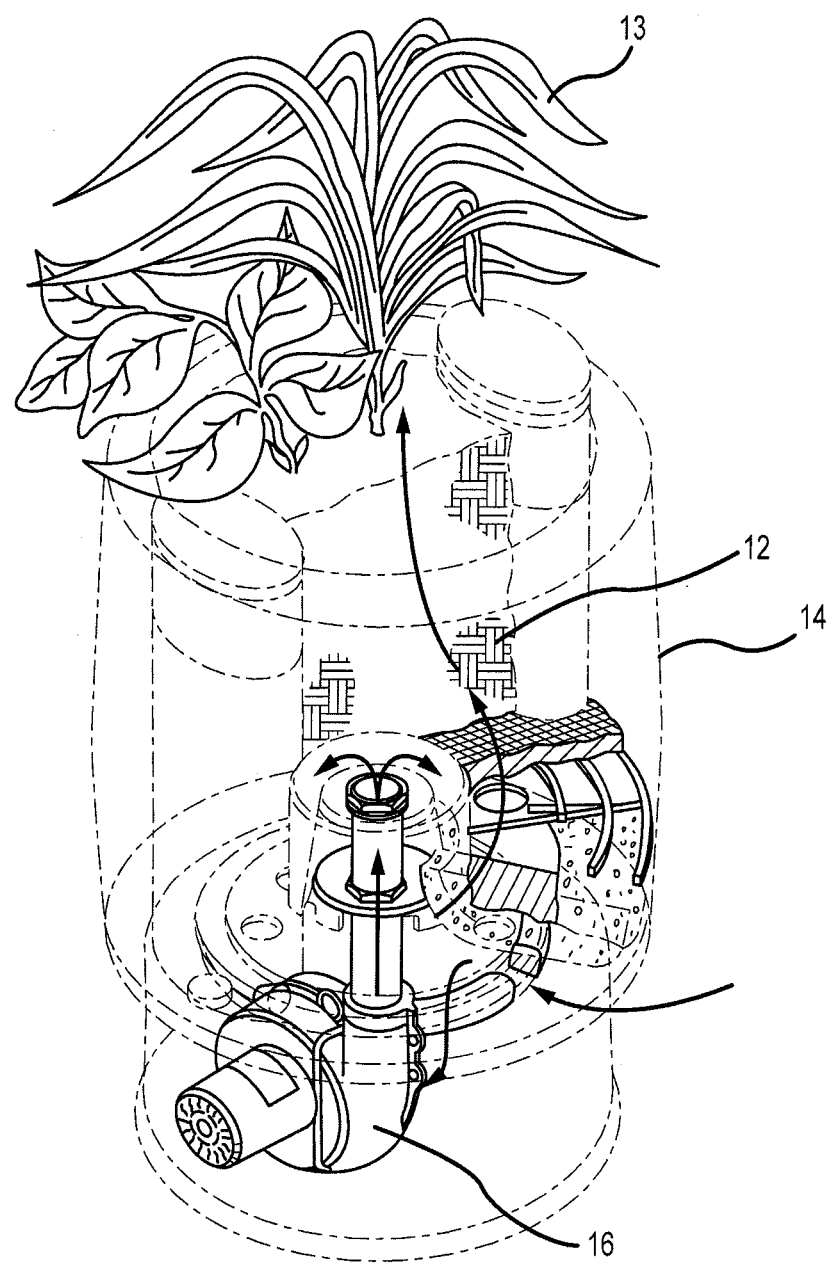
FIG. 1 shows one embodiment where manure-containing soil is placed in a container that also facilitates the growth of plants such that the placement of manure-containing vessels about a resident dwelling can be disguised and made innocuous.

In certain embodiments of the present invention, a system and method includes creating conditions in a residential urban dwelling where an expectant mother resides that provides a rich array of microbial stimuli generated by the presence of air being circulated that contains components derived from manure obtained from bovine animals, and preferably in addition, at least manure from poultry, and even more preferably manure from animals that have been administered few if any antibiotics. In one preferred embodiment to a system of the present invention, farm soil obtained from a farm having the above described manure (and thus the rich array of microbes, fungi, and other allergens associated with such soil, and as referred to herein generally as being manure-containing soil) is included in a container that preferably further includes an air circulating mechanism such that air containing such allergens is circulated throughout the room or predetermined area within a dwelling such that an expectant mother exposed to and breathing such air is able to inoculate her unborn child in a manner such that the child will be free of allergies that might otherwise be encountered. In preferred embodiments, the system and method generate the desired (albeit perhaps as yet unidentified at present) allergens such that they are made available in effective amounts and at relevant times such that expectant mothers are effectively exposed thereto. Thus, effective dispersion devices of such allergens can vary widely, from stand alone units to those that involve circulation though building or dwelling, or at least a room. The objective of such systems and method is to create a residential environment such that an expectant mother achieves an increase in the number of T cells in the cord blood of the mother with a newborn child, such goal accomplished by predetermined exposure of such woman to allergens derived from farm soil that contains an appreciable amount of bovine manure, and preferably manure that has undergone minimal if any treatments that would substantially reduce the number and variety of microbes and fungi present therein when the farm soil was collected.

While not bound by theory, one goal of the present invention is to recreate both the substance as well as the timing and frequency of exposure sufficient to achieve an increase in the number of T cells in the cord blood of the mother with a newborn child. Thus, one objective of various embodiments of the present invention is to provide a rich array of microbial stimuli, that resembles the world in which the human immune system evolved, including human's long and close relationship with farm animals, and in particular, bovine animals.

One aspect of the present invention is directed to an indoor air emitter that includes a soil bed reactor through which room air is passed such that certain manure containing particulates, microbes, fungi, etc. is emitted into the indoor environment where a pregnant woman resides. Indoor air purifiers have been employed to remove various particulate elements and noxious agents. But the purposeful emission of microbes and fungi into a residential environment is unusual, and in fact, many would be deterred from the concept of purposefully exposing individuals, and especially expectant mothers, to microbes and fungi that are derived from farm soil containing manure. Modern urban life radically reduces exposure to microbes and parasites that have been part of the human ecosystem for eons. The immune system is known to be stimulated by the inhalation of bacterial cell wall components called "endotoxin" that become airborne as cow manure dries up. In evolutionary terms, the removal of many of these microbes from daily life in the last two generations is very sudden. It is believed that babies' new immune systems need these microbes to calibrate themselves, so as to respond with the right firepower for the threat at hand. Without adequate calibration, the immune system overreacts to normally safe substances, like pollen, dog fur, or peanuts, and/or gets stuck in a chronic state of overreaction, causing inflammation. It is believed that under-exposure to microbes skews gut bacterial ecosystems to create inflammatory immune responses. The present inventors contend that controlled exposures of pregnant mothers to microbes creates an immune-boosting desired effect for the unborn child, and as long as there is post-natal exposure to such allergens, the child will have a vastly reduced occurrence of allergies.

In one embodiment, the system comprises an air treatment device comprising: a container having at least one opening therein, a supply of manure-containing soil held in a container for the receipt and retention of the received manure-containing soil, an apertured housing through which a blowing device is directed so as to emit air into a room after it has been exposed to said manure containing soil.

In one embodiment of a particular unit that can be employed in the present system and method is a device that includes a base and an open container on top of the base. The container comprises an upper chamber, having a layer of soil supporting the growth of aerobic microorganisms, and a lower chamber having a water bath. Preferably, the container on top of the base can freely rotate upon the base. Means are provided for drawing air from a room into the base, passing the air upwardly into the container through a duct connecting the base to the bottom portion of the container, directing the air passed from the base through a soil bed retainer plate and into the soil layer, and discharging the air from the surface of the soil back into the room.

Such an air emitter is designed to be aesthetically pleasing and may be incorporated with a soil layer suitable for supporting growth of plants selected by the homeowner or office worker.

To comply with appropriate written description and enablement requirements and to provide sufficient guidance in how one of skill in the art can make and use the various and numerous embodiments of the present invention, incorporated herein in their entireties are the following: U.S. Pat. No. 4,995,555 to Woodruff; U.S. Pat. No. 8,454,729 to Mittelmark et al., U.S. Pat. No. 6,722,577 to Dobyns, III and U.S. Pat. No. 5,277,877 to Jeffrey.; WO2013107750 to Holvoet; WO2011020780 to Holvoet; US 20140044677 to Qvit-raz; 20140363441 to Grandea; and WO 2014103488 to Hasegawa and 20150064138 to Lu et al.

Still other embodiments include the use of air flow devices, such as bladeless fans, including those described in US patent publication No. 20130330215 to Li; 20130323100 to Poulton, 20130323025 to Crawford; U.S. Pat. No. 7,540,432 to Majerowski et al., and 20070057086 to Van Kippersluis, all of the preceding incorporated herein in their entireties. In a particular embodiment, a sample of manure-containing soil is positioned in the proximate region of an opening of the bladeless fan, such that the exiting airflow carries the microbe-containing air into the room environment. As in certain embodiments the fan speed as well as temperature of the air flow can be adjusted, it is preferred that a warm (e.g. 75 F. degree) flow of air be employed to disperse desired constituents of the soil sample employed.

Thus, one embodiment comprises an air treating device that may include a liquid reservoir, an opening, a base supporting and surrounding a liquid absorbent material, a liquid metering control mechanism, and a container within which soil containing manure (preferably derived from bovine and other animals selected from the group consisting of sheep, goats, poultry, and pigs) so that the device provides a rate of dispersion of antigenic materials sufficient to expose an expectant mother so as to inoculate her unborn child and thus reduce the incidence of allergies of the child when born. The maintenance of the soil in a moist state is preferred in many embodiments such that the level of microbes and fungi present originally in the soil (e.g. when it was collected) remains fairly consistent, taking into account the anticipated and normal die off of such microbes over time. In other words, maintaining conditions such that the desired viability of allergenic properties that are derived from having the soil containing microbes present, if not viable and reproducing, will vary in view of the various temperatures, humidity and other environmental conditions where the present invention is indeed to be employed.

Referring now to the figures, FIG. 1 illustrates another embodiment where manure-containing soil 12 is placed in a container 14 that also facilitates the growth of plants such that the placement of manure-containing vessels about a resident dwelling can be disguised and made innocuous. Moreover, it is believed beneficial to have growing plants indoors to provide a source of oxygen, to naturally absorb and ameliorate harmful agents in soil 12, and to facilitate the wetting of the manure containing soil 12 when the plants grown in or associated with such soil 12 requires water for survival. In particular embodiments, it is beneficial to have an air circulating device 16 associated with the manure-containing soil vessel such that air passes over and picks up the allergens in the soil 12, such that such allergens are dispersed throughout a dwelling room (e.g. where a pregnant mother would inhabit for certain periods of time and at certain frequencies. In one particular embodiment, such an air circulating device 16 comprises a bladeless fan 26 (see e.g. FIG. 4), such as one manufactured by Dyson™, and even more preferably one where the adjustment of temperature of the air stream is adjustable. Thus, in a preferred embodiment, the temperature of the air surrounding the manure-containing soil 12, as well as the rate of airflow across the surface of such soil 12, is controllable.

Figure 2:
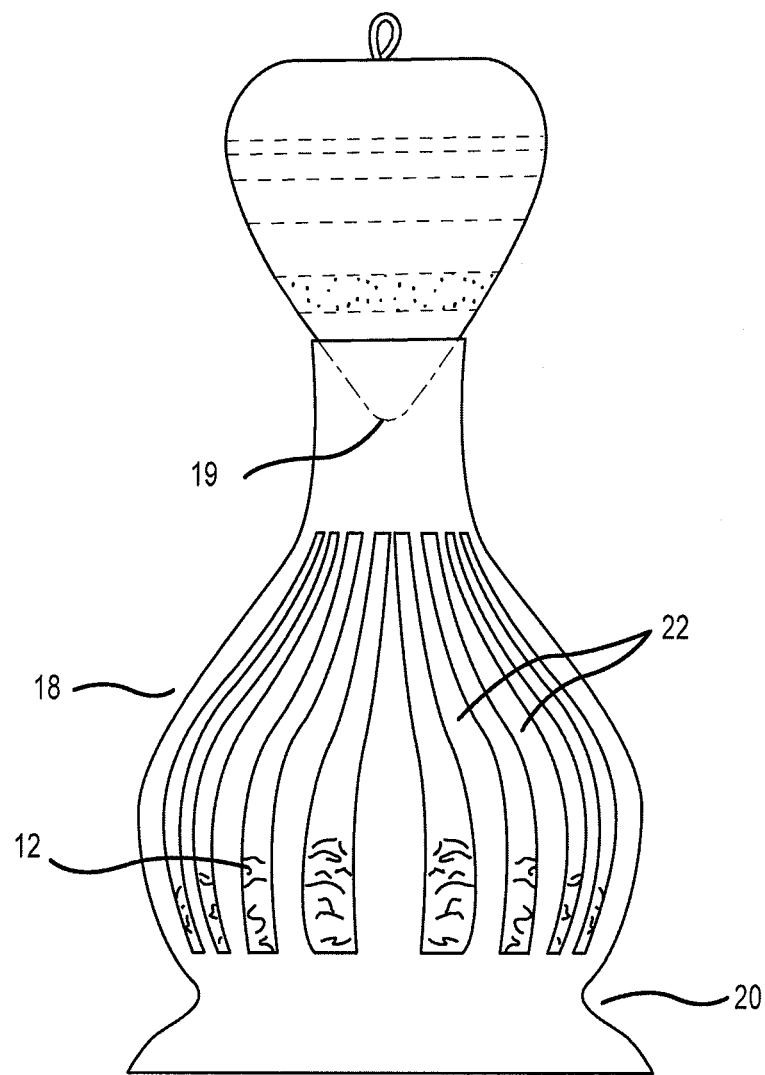
FIG. 2 shows one embodiment of a dispensing unit for manure-containing soil depicting a conical shape vessel with openings through which desired portions of microbes can be dispersed into a room environment.

FIG. 2 shows one embodiment of a dispensing unit 18 for manure-containing soil 12 where a conical shape vessel 20 has controlled openings 22 through which desired portions of microbes can be dispersed into a room environment. The top portion 19 of the device 18 can be provided with liquid, such as water, to periodically wet the manure-containing soil 12 positioned in the lower section of the vessel container 20.

Figure 3:
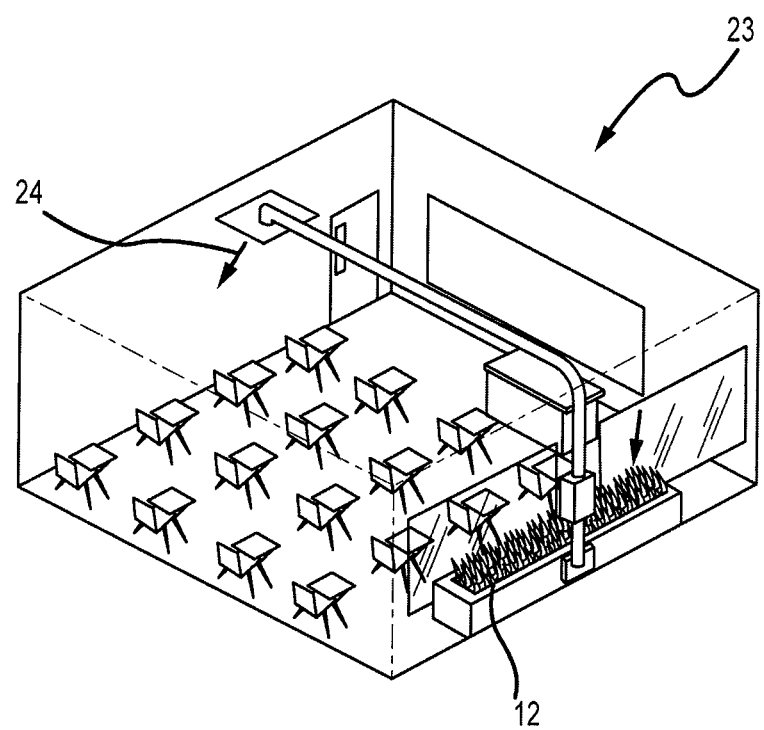
FIG. 3 shows another embodiment where the system is employed to dispense air throughout a room after the air has contacted the manure-containing soil.

FIG. 3 depicts another embodiment where the system is employed to dispense air throughout a room 23 (such as a classroom, but alternatively a living room, nursery, family room, etc.) after the air has contacted the manure-containing soil 12, thus picking up and dispersing allergens derived from microbes, fungi and other desired materials contained in such soil 12. As will be appreciated, various embodiments include the employment of existing air circulating systems in a building, such as HVAC systems, such that manure-containing soil 12 can be brought into association with an airstream 24 emanating from such HVAC systems, thus dispersing the allergens produced from such soil 12 into the air of the building, or select rooms 23 of the building.

Figure 4:
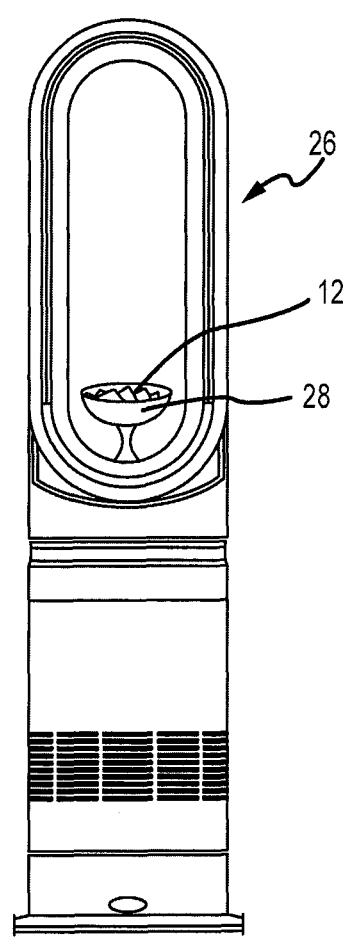
FIG. 4 shows a system that employs the use of a bladeless fan to facilitate the communication of microbe containing air through a predetermined region of an interior space.

FIG. 4 depicts one system of the invention that employs the use of a bladeless fan 26 to facilitate the communication of microbe containing air through a predetermined region of an interior space where an expectant mother is to inhabit for particular time spans. As explained herein, the use of a bladeless fan has certain aesthetic as well as practical advantages, including the absence of the pulsing nature of a bladed fan and the provision of a steady and consistent stream of air containing the desired allergens present in the manure-containing samples brought into close proximity to the operating fan. The ability to adjust the rate of air flow across such soil sample 12, and the additional ability to regulate the temperature of such air flow, can be used to maximize the dispersion of desired allergens derived from the manure-containing oil. In one embodiment, a separate container 28 for holding such soil is provided in association with the bladeless fan 26, preferably positioned just in front of the emerging airstream developed by the fan 26.

Figure 5:
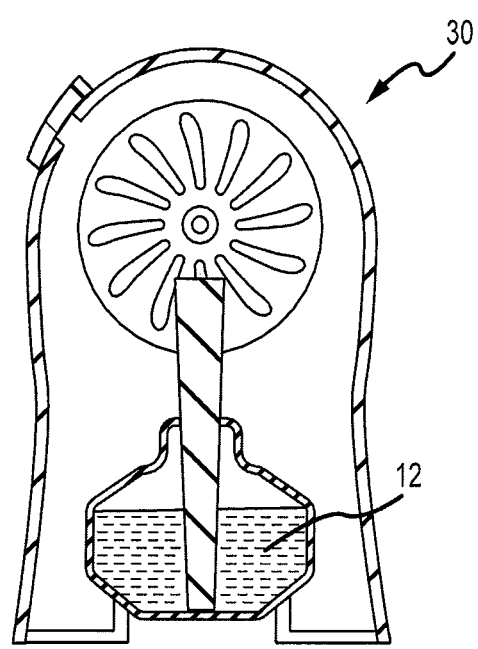
FIG. 5 shows another device for disseminating microbe laden air in an interior enclosure.
Figure 6:
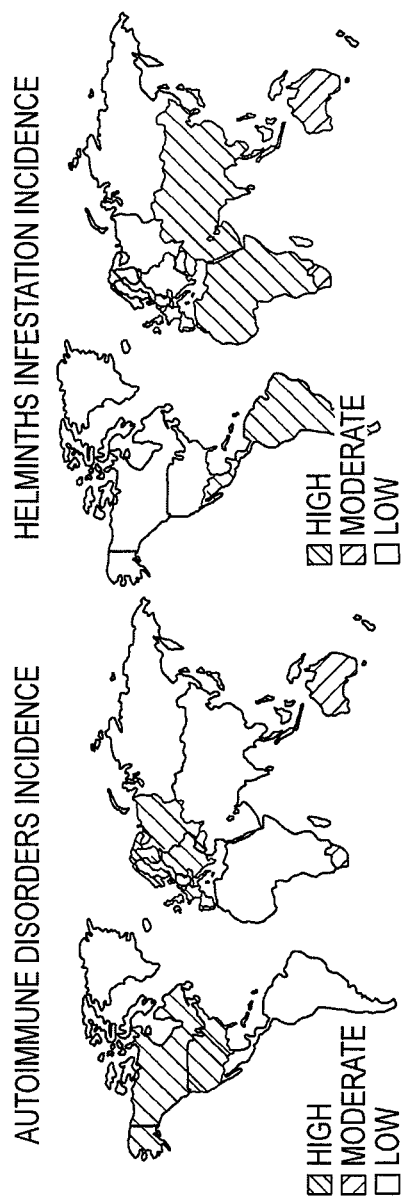
FIG. 6 shows a global map indicating the incidence of autoimmune disorders and helminth infestations in certain countries around the world.
Figure 7:
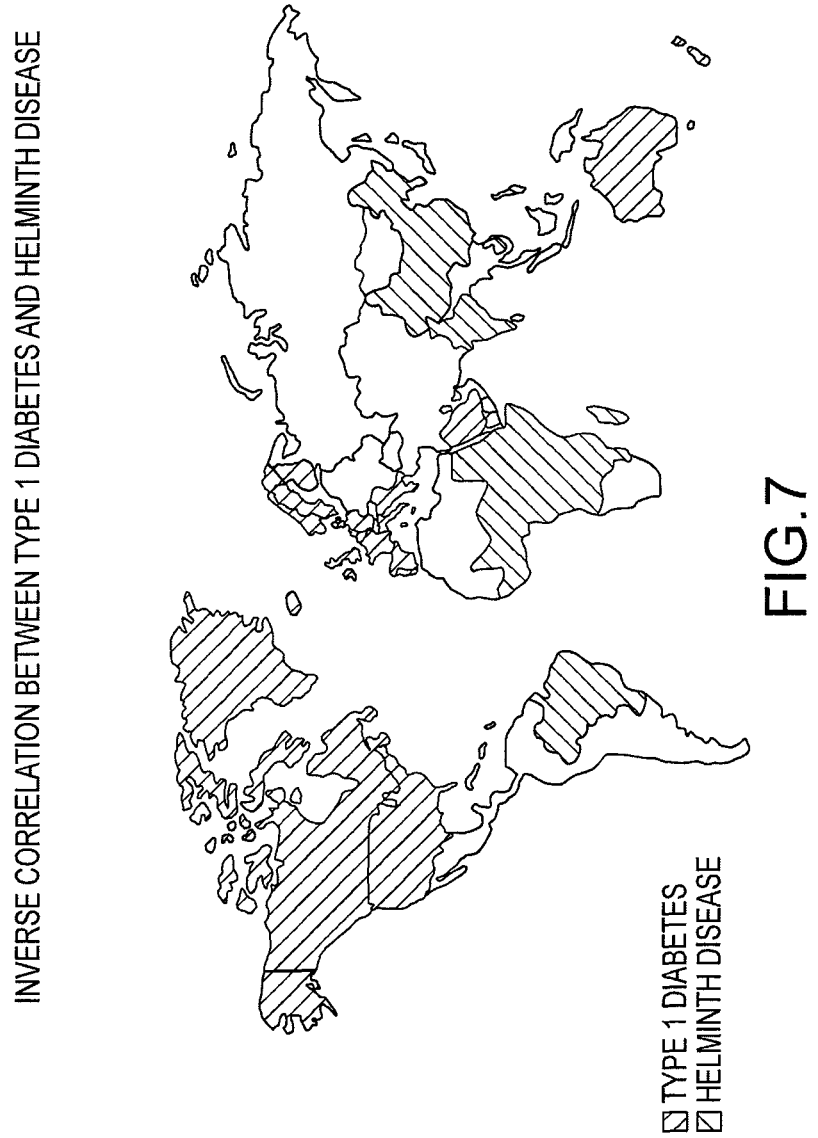
FIG. 7 shows a global map indicating the prevalence of Type 1Diabetes (T1D) in certain countries around the world and the inverse correlation between Type 1 Diabetes (T1D) and helminth diseases.
Figure 8:
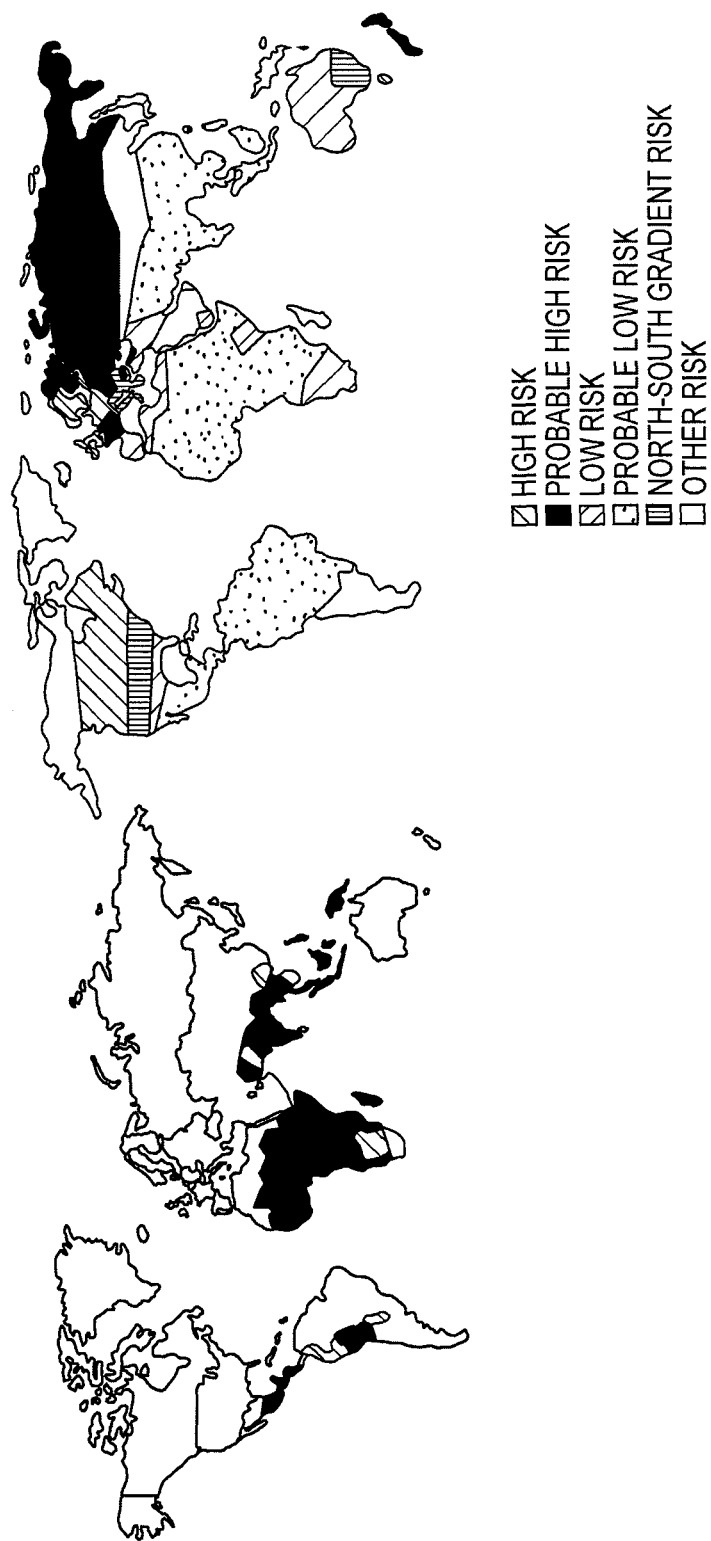
FIG. 8 shows a global map indicating the inverse correlation between Type multiple sclerosis and helminth diseases in certain counties around the world.

FIG. 5 depicts yet another embodiment of a device 30 suitable for disseminating microbe laden air in an interior enclosure such that a pregnant woman would be exposed to the variety of microbes (and related particles) emanating from the conveyance of air-borne material picked up from the surface of manure-containing soil 12 that is positioned such that the air flow produced by the device 30 passes over such soil.

In practicing one embodiment of the method of the present invention, one provides a device 14 that contains manure-containing soil 12; provides manure-containing soil 12 (preferably replaced every month during and after the pregnancy of a woman for a total period of between about 3 months and 24 months, more preferably at least about 4 months of pregnancy and at least about 3 months after the baby is born); providing (or operating) the device 14 such that the pregnant mother is exposed to the microbes (or portions thereof having allergenic properties) for periods of time sufficient to trigger a response from the woman's immune system in reaction to such allergens (preferably such exposure occurring for at least 10 minute time intervals and at least every three days); operating the device 14 for a period of time after the baby is born (preferably for at least 3 months after birth, where the baby is exposed to the air flow emanating from the device that is operatively situated next to the manure-containing soil 12 such that the baby is exposed to the allergens in such soil 12. It is believed that by the practice of such method, the pregnant mother's immune system during her pregnancy, as well as the baby's immune system at birth or shortly thereafter, will be sufficiently charged such that the baby will be spared allergic disease.

Periodic replacement of soil with "fresh" soil is preferred, and especially soil from another separate batch of soil that possesses manure from different animals. In this way, it is possible to promote the diversity of allergens that an expectant mother is exposed to, thus protecting the health of her as yet unborn child. Preferably, soil is replenished or replaced at least every two months, more preferably at least once a month, and even more preferably after about every three-five days. The amount of soil provided can vary, but preferably is at least about five ounces, more preferably at least about 20 ounces and most preferably more than about one half pound. In some embodiments, such as were potted indoor plants are provided, the manure-containing soil samples are placed within the potted plants, such that a considerable amount of manure-containing soil may be provided within the confines of a dwelling where an expectant mother may live.

The frequency with which an expectant mother should experience an environment having one or more of the systems described herein can vary, but preferably the mother should experience the interior space having the manure-containing soil (e.g. walk through the interior space and remain therein for a period of time) at least once a week for a period of 5-10 minutes; more preferably at least once every three days for at least 10 minutes; and most preferably at least once every other day for a period of at least 15 minutes. In such a manner, it is believed that the expectant mother will be exposed to a sufficient amount and frequency of allergens contained in and emanating from the manure-containing soil that the mother's immune system will then be triggered in a positive way, thus conferring protection to the unborn child in the various ways described herein.

In preferred embodiments, the manure-containing soil is comprised of a mixture of several soils collected on different farms from different regions and at different times, and especially at different seasons. It is believed that various microbes, viruses, fungi, etc are present in animal manure at different times of year, often dependent upon the temperature, the feed provided to the animal, and the ambient conditions where the manure-containing soil is collected. The general objective is to maximize the types and varieties of allergens that are present on a natural farm such that the immunity boosting benefits derived from having exposure thereto can be enjoyed and experienced by those living and residing far from such farm locales. Thus, in one embodiment, soil is collected from Amish farms where cattle are raised and where the cattle are not provided with antibiotics other than tylosin. In more preferred embodiments, the soil is collected from more than one of such farms and combined so that a used of the present method and system can derive the benefit of having a mixture of allergens that may be present and distinct from each locale.

One of skill in the art will appreciate that while the description herein has focused on bovine manure-containing soil, it should be understood that other types and kids of farm animals can, and preferably are, included with respect to the source of the manure obtained. Thus, in preferred embodiments, soil is collected from farms that not only raise cattle, but also poultry, particularly chickens, goats, pigs and sheep. It is believed that the most robust immune response will be achieved via the exposure of an expectant mother to a myriad of different allergens derived from farm animals that humans have traditionally over the last thousand years, experienced in close proximity during the human's life. Thus, while the particular identity of microbes, fungi, pant material, viruses, etc. is admittedly long and varied, the ultimate objective of exposure to a vast variety of allergens derived from farm animal manure is deemed necessary to confer immunologic protection from the allergy epidemic that we are experiencing today.

As mentioned herein, due to the effects of lead on the formation of a robust immune system, one aspect of preferred embodiments of the present invention involve the avoidance of lead exposure, for example, via lead-based paint environments, when the present system and methods are employed in a residence where expectant mothers visit. Thus, in one embodiment, the avoidance by expectant mothers during their 9 month pregnancy of lead containing environments, in addition to exposure to allergens emanating from farm animal manure-containing soils, is believed to be most efficacious to establish immunity to common allergies by newborn babies.

It should be understood that manure-containing soils, as used herein, includes the provision of the collection of allergens typically included in such naturally occurring soils. Thus, for purposes of clarity, such term includes the refinement of manure and/or manure containing soils that contain such allergens such that separation of the allergens from such manure and/or soil and use of the same in a system or method where expectant mothers are purposefully exposed to the same in confined indoor spaces, would be covered by the present invention. Preferably, conditions of the manure-containing soil in an urban dwelling is maintained in a manner such that certain harmful bacteria propagation is reduced. Thus, for example, soil may be pretreated (before use in the household) at certain higher temperatures to kill of certain undesired bacteria, such as *E. coli* and certain fecal coliform populations, such temperatures being as high as about 41 degrees C. and above about 27 degrees C. US patent publication No. 20070231923 to Cumberland et al is incorporated herein by this reference to provide guidance and support for the various different ways that Diagnostic assays can be employed to determine specific microbes, fungi, viruses and proteins in biological and environmental samples to assist in assessing with the determination of the presence or absence of undesired components of any given sample.

Moreover, moisture content of the soil can have a dramatic effect on the survival of certain undesired bacteria, and thus, it is preferred to maintain the soil at below about 80% moisture content. In certain embodiments, however, particularly desired genus and species of bacteria are added to soil after treatment of such soil to destroy certain undesired bacteria. In such situations, the temperature and moisture content of the soil can be adjusted to afford desired levels of bacterial propagation, fungi viability, etc. to effect the desired dispersion into the atmosphere of allergens that will promote the immune response in an infant's developing immune system.

In preferred embodiments, it is appreciated that the malodorous components of manure-containing soils will be distasteful to many people, especially to scent-enhanced pregnant women. Thus, in various embodiments the present invention includes various masking agents to reduce, eliminate or at minimum, ameliorate the undesired odiferous components of such soil. For example, in certain embodiment, cyclodextrin, or other Frebreeze™ compositions are used in association with the systems and methods described herein. In such a manner, the benefits of the allergens associated with the manure-containing soils is attained without the undesired odors associated with farm animal manure. Various perfume-type agents can be employed to cover or mask the unpleasant smells that may be associated with various farm animal manure and one of skill in the art will appreciate the variety of ways such odor-reducing devices and methods can be employed in conjunction with the present embodiments of the present invention.

In various embodiments of the present invention, one objective is to increase airborne bacteria into a residential environment such that microbes present in manure containing soil, especially those as described herein that contain manure from bovine and one of pigs, sheep, horses, oxen, lamas, poultry and goats, are the source of allergens that act to increase the number of T cells in a mother's cord blood. One aspect of the present invention is directed to prenatal exposure to a farming environment by having an expectant mother provided with access to a room where manure containing soil is present such that allergens are emitted from such soil into the environment in a manner and in a sufficient amount such that the mother can be sufficiently exposed to microbes and fungi present in such soil. In particular, one aspect of the present invention is directed to the purposeful exposure of an expectant mother to environments rich in microbial compounds in order to promote the development of atopic sensitization, asthma, and corresponding alterations in the innate immune system in offspring. It is believed that maternal exposure to an environment rich in microbial compounds acts to protect against the development of atopic sensitization and leads to upregulation of receptors of the innate immune system. In one embodiment, the allergens to which the expectant mother is exposed comprises a variety of ordinary germs, such as those present in farm soils having resident bovine, and more preferably bovine, porcine, sheep, poultry, cats dogs, horses.

The recent increase in allergic diseases such as atopic dermatitis, atopic eczema, and allergic rhinitis has been, and continues to be, a serious social problem in many countries. There is a theory which implies that allergy and asthma have increased during the last 20 to 50 years because of a reduced exposure in childhood to bacterial and viral infections brought about by improvements in public health measures such as vaccination and sanitation. Allergic diseases are reported to be caused by a skew in the balance between T helper type 1 (Th1) and 2 (Th2) cells. Classical allergy is a type 2 hypersensitivity reaction mediated by the interaction of mast cells and eosinophils coated with allergen-specific IgE and a cross-lining allergen. Certain lactic acid bacteria have been shown to stimulate Th1 related cytokines secretion and are believed to have the potential to either prevent or ameliorate disease conditions or both. While the current state of evidence suggests that probiotic effects are strain specific, the present inventors contend that the multitude of allergens involved in establishing a robust immune response are not so confined. Immunotherapy has been used in the treatment of a variety of conditions ranging from allergies to cellular proliferative diseases such as cancers. Allergen immunotherapy attempts to reduce sensitivity to allergens, i.e. suppress an immune response. In addition to microbial factors that may suppress immune responses, potent immune activators are also believed to be of microbial origin, including bacterial enterotoxins, parasite-derived excretory-secretory products, and viral nucleic acids.

One objective of the present invention is to shift the microbe population in the guts of individuals towards species that prevent their immune systems from overreacting to airborne allergens. While single bacterial species may be employed, in preferred embodiments, a plurality of bacterial species are used to attain such benefit. It is believed that exposure at appropriate times to allergens (e.g. those previously typically encountered by humans due to the farming origins of ancient societies) is able to reduce the risk of allergic conditions for unborn babies and thus provide them with protection later in life. Thus, by purposeful and predetermined exposure to a plurality of allergens during fetal development, it is possible to influence the immune system of the unborn child, especially if such allergen exposure continues after birth for a predetermined time. By such purposeful exposure, it is possible to change a propensity for allergies by affecting the microbes presence in the environment of pregnant women and thus influence the immune systems of the unborn child.

In preferred embodiments, certain microbes from the genus *Lactobacillus*, and more particularly, the species *Lactobacillus johnsonii*, are employed, preferably derived directly from manure of farm animals. *L. johnsnoii* is a known human gut colonizer and becomes a dominant member of the maternal vaginal microbiome just before birth and is believed to assist in structuring the initial community of microbes in a baby's gut. In order to suppress allergic symptoms, it is believed effective to lead the immune balance towards "Th1-type" dominant, and generally, lactic acid bacteria are said to have an activity to lead the immune balance towards "Th1-type" dominant. In one embodiment, *Lactobacillus crispatus* KT-11 strain (FERM BP-11332) is used to lead the immune balance towards "Th1-type dominant", with such strain used in combination with other lactic acid bacteria belonging to the genus *Lactobacillus*, genus *Bifidobacterium*, genus *Leuconostoc*, genus *Enterococcus*, and genus *Pediococcus*.

While *L. johnsonii* is a preferred bacteria in many embodiments, other bacteria are employed in various embodiments, such bacteria selected from the group consisting essentially of *Lactobacillus acidophilus, Lactobacillus brevis, Lactobacillus buchneri, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus rhamnosus, Lactobacillus salivarius, Streptococcus thermophilus, Lactococcus lactis, Lactococcus plantarum, Lactococcus raffinolactis, Leuconostoc lactis, Leuconostoc mesenteroides, Enterococcus faecalis,* and *Enterococcus faecium;* an anti-allergic agent comprising as an active ingredient human-derived bifidobacteria selected from *Bifidobacterium infantis, Bifidobacterium breve, Bifidobacterium longum,* and *Bifidobacterium bifidum; Enterococcus faecalis* and *Lactobacillus reuteri,* and *Lactobacillus paracasei*.

In certain embodiments, a method for enhancing immunity includes the use of a mixed culture of bacterial cells of three to eight species of lactic acid bacteria. In particular mixed cultures, the following may be included: *Saccharomyces cerevisiae, Lactobacillus delbrueckii, Lactobacillus acidophilus, Lactobacillus plantarum, Lactobacillus fermentum, Lactobacillus casei, Lactobacillus rhamnosus, Lactococcus lactis* and *Streptococcus thermophilus; Enterococcus faecium; Bacillus coagulans; Leuconostoc, Pediococcus, Lactobacillus casei, Lactobacillus plantarum, Lactococcus lactis* subspecies *lactis, Lactococcus lactis* subspecies *cremoris; Lactobacillus plantarum; Pediococcus pentosaceus; Streptococcus thermophilus; Lactobacillus paracasei; Lactobacillus plantarum, Lactobacillus gasseri* and *Lactobacillus salivarius; Lactobacillus acidophilus* PM-A0002, *Lactobacillus gasseri, Lactobacillus salivarius, Lactobacillus acidophilus* PM-A0013; *Leuconostoc mesenteroides; Lactobacillus bulgaricus, Lactobacillus rhamnosus, Lactobacillus acidophilus, Lactobacillus paracasei; Bifidobacterium bifidum; Lactobacillus brevis; Enterococcus durans, Leuconostoc mesenteroides; Lactobacillus crispatus.* Still other embodiments of the invention may comprise extracts obtained from one or more of the following species: *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius,* and *Lactobacillus lactis*. In some embodiments, at least one strain from each of the above species of bacteria is used, while in other embodiments, one or more specific strains from the list above may be removed or substituted with one or more different strains. In particular, some embodiments of the present invention comprise an extract obtained from one or more of the following bacterial strains: *Lactobacillus fermentum* I-3929, *Lactobacillus rhamnosus* 71.38, *Lactobacillus plantarum* 71.39, *Lactobacillus johnsonii* 103782, and *Lactobacillus helveticus* 103146. The strains above are deposited according to the Budapest Treaty. *Lactobacillus fermentum* I-3929, *Lactobacillus rhamnosus* 71.38, *Lactobacillus plantarum* 71.39, *Lactobacillus johnsonii* 103782, and *Lactobacillus helveticus* 103146 are each deposited at the Collection Nationale de Culture des Microorganismes at the Institut Pasteur, 25 rue du Dr. Roux, 75724 Paris, France. *Lactobacillus fermentum* 1-3929 was deposited on Feb. 27, 2008. The other strains are among the depository's collections and may be obtained by contacting the depository. The following bacteria species may also be employed: *Lactobacillus acidophilus* PM-A0002 deposit number M 207038, *Lactobacillus gasseri* PM-A0005 deposit number M 207039, *Lactobacillus salivarius* PM-A0006 deposit number M 207040, *Lactobacillus johnsonii* PM-A0009 deposit number M 207041 and *Lactobacillus acidophilus* PM-A0013 deposit number M207042. While preferred embodiments of the present invention involve the use of manure-containing soils, other embodiments include compositions devoid of manure and that comprise just select genus and species of microbes, fungi, viruses, etc. in accordance with the method, system and various devices described herein.

In preferred embodiments, the environment whereby the expectant mother is exposed is devoid of significant levels of lead. It is speculated that the metal lead is a common environmental pollutant in inner cities and in older houses, released from factories and during mining operations. It is believed that lead disrupts normal immune system development, leading to increased frequency of the development of allergies and asthma. Lead exposure during critical, prenatal periods of development can impact immune system function well after birth. It is speculated that in the presence of lead exposure, the fetal immune system is changed so it overreacts to common particles in the environment. Thus, one aspect of the present invention is to avoid exposure of an expectant mother to lead, while at the same time, exposing such mother to significant levels of microbes and fungi derived from manure containing soil collected from certain farms, especially those that do not employ significant amounts of antibiotics in treating their cows, sheep, pigs, goats or poultry. Similarly, it is one aspect of the present invention for the expectant mother to desist from the use of anti-bacterial soap, as such use is believed to inhibit the immunity conferring benefits to be derived from the present invention. It is further believed that soil containing manure from bovines (as well as other farm animals) and where neither the animals nor the manure is treated with an anti-biotic, is more effective as a source of desired allergens responsible for conferring the protective immunologic attributes that pass from an expectant mother to her unborn child. In a preferred embodiment of the invention, the child, after he or she is born, is further exposed to the manure containing soil that the expectant mother was exposed to during the pregnancy. In such a manner, it is believed that the early exposure to allergens is reinforced and permits the immune system to fully protect the child from such allergens. In other words, the child's immune system is permitted to more fully mature under the influence of continued exposure to the same type of microbes and fungi as was the mother during pregnancy.

In other preferred embodiments, the administration of any antibiotic to a bovine—other than tylosin, is avoided. In this manner, the rich variety of microbes and fungi, which is believed responsible for conferring immunity sought to be achieved via exposure to manure from bovines, is retained. It is believed that the maternal microbial and fungal environment during pregnancy assists in programming the immune development of the child. It is postulated that prenatal environmental exposure alters gene expression via epigenetic mechanisms and induces physiological adaptations to the postnatal environment. Thus, one aspect of the present invention is directed to providing an environment in the months during pregnancy such that allergens purposefully provided and that are derived from manure-containing farm soils (especially those having manure from bovines that are not treated with antibiotics) is able to influence immune-mediated diseases. In more preferred embodiments, immunomodulatory effects are derived from such farm soil exposure in a residential room where purposeful dispersion of microbes and fungi from such soil is achieved via one or more devices. In such a manner prenatal, perinatal and postnatal interventions can be achieved to combat the allergy epidemic.

Other aspects of certain embodiments of the present invention involve testing to determine whether the expectant mother has been properly and sufficiently exposed to allergens so as to effectively create conditions such that her child will be effectively immunized in a manner that will reduce or preclude the prospect of allergic diseases being acquired by her infant. One of skill in the art will appreciate the many ways to conduct such tests to detect the various allergens at issue. These include, but are not limited to, analysis and kits employed according to US patent publications 20070059718 and 20070059774 to Toner, 20060252087 to Tang, 20040053352 to Ouyang and 20040142463 to Walker, 20120039806 to Lahoud; 20040166501 to Azimzai, each of which are incorporated in their entireties by this reference. In certain embodiments, tests are conducted at various stages of pregnancy, preferably initiated at a time early in the pregnancy and continuing periodically throughout the pregnancy. Thus, at least three times during the pregnancy, more preferably every other month of the pregnancy, and most preferably at least about every two weeks, tests are conducted to determine whether one of the frequency, duration, volume of soil, sufficient dispersion of allergens in a predetermined space inside the to-be mother's dwelling (determined in various manners, but preferably by airborne concentration of allergens and/or concentrations of immunogenic fragments of a polypeptides that indicate the presence of such allergens in the maternal or fetal blood) is sufficient to trigger the desired immune response. One will appreciate, however, that if early tests determine that the expectant mother is being exposed sufficiently to allergens via the system and method of the invention, then further testing can be reduced or eliminated as it will be apparent that the desired immunity issues have been addressed via sufficient exposure.

One aspect of the present invention relates to commercial availability of manure-containing soil having the desired characteristics described herein. A such, a collection and distribution aspect of the invention relates to an entity dedicated to determining particular locations where appropriate manure-containing soil can be collected (preferably farms where little to no antibiotics are employed; visiting such locations at least three and preferably more time a year to collect amounts of soil; packaging such soil in amounts and packages for shipment to various customers or other distributors such that a customer desiring soil samples for use in their residential (or possibly also in office settings) can order and obtain such soil in a state such that the microbes, fungi and other materials contained in such soil is suitable for use in a home environment, including the many variations set forth herein (e.g. as part of house plants; included in air circulating systems, etc.). Details as to how such samples may be packaged and shipped are found, for example, in US patent publication No. 20120029832 to Dodgson, which is incorporated in its entirety by this reference. Similarly, US patent publication No. 20070063026 to Mamaropolos, et al. is incorporated herein by this reference with respect to the various ways by which samples can be packaged, shipped, distributed, etc. In preferred embodiments, a customer would have a standing order to receive numerous shipments of soil samples, such samples collected relatively recently from the date of shipment (e.g. preferably within the same month from collection off the farm to shipment to a customer) such that the microbes included in such sample are viable for the purposes herein. Thus, a pregnant woman would start a course of air flow treatment in her home by providing the first soil sample in her home environment (via one of the ways described herein); expose herself to the allergens emanating from such soil samples; replace the sample with a "fresh" sample provided by the distributor thereof on a periodic basis, and continue such course for a time period extending beyond the birth of her baby, preferably extending 3 months thereafter, more preferably at least 6 months and most preferably at least a year. The timing of the cessation of soil sample exposure is believed to be appropriate at around the same time a woman may cease breast feeding, which is typically around on year form birth. Each of the samples sent would preferably originate from different farms and would have been collected at different times of year so as to expose the pregnant mother to a wide variety and amount of different allergens, thus providing a robust immune response in her infant.

One of skill in the art will also appreciate the many commercialization opportunities, including slogans for trademarks, that exist and that can be employed to advertise the present method and system. Go to that which has been abandoned. Search for the plant that combats death. The one worn by dancing women in ancient times. It flowers in the water and darkens your skin and it is part of the key.

While the above description has focused on allergic and autoimmune conditions, specifically those acquired by children who have not had their mothers exposed to such allergens during pregnancy, it is further believed that such exposure to manure-continuing soils in accordance with the present invention may also be useful in reducing the occurrence of deadly breast and colon cancers.

Certain embodiments of the present invention include a combination of particular bacterial strains, selected from the group consisting of *Prevotella; Lactobacillus johnsonii; Bacteroides fragilis, Lactobacillus ruminus,* and at least one of *B. longum* bv. *Infantis* isolate UCD272 or *B. longum* bv. *Infantis,* AY151398, together with an antibody, or fragment thereof, of IgE. Such composition is preferably formulated for nasal tissue delivery and administration in a human, such as by a nasal gel or by an inhalation delivery system well known in the art. The amount of bacterial and IgE in such a formulation may vary, but should be at least prepared in an effective amount dependent upon the mass of the human being administered, and is preferably The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments. As described herein, however, administration to a newborn infant in the first hours after birth is most preferred, and nasal formulations are especially preferred as administration can be promptly and effectively performed immediately after birth. Another embodiment is directed to a method of treating type 1 diabetes mellitus in a human patient comprising administering to a human patient in need thereof a therapeutically effective amount of a pharmaceutical formulation comprising at least two of: a helminthic parasite, an antibody, or fragment thereof, of IgE; and a bacterial component that includes one or more of the following: *Prevotella; Lactobacillus johnsonii; Bacteroides fragilis, Lactobacillus ruminus,* and at least one of *B. longum* bv. *Infantis* isolate UCD272 or *B. longum* bv. *Infantis,* AY151398.

Other embodiments are directed to a method of treating type 2 diabetes mellitus comprising administering to a human patient in need thereof a therapeutically effective amount of a pharmaceutical formulation comprising a helminthic parasite or a biologically active portion thereof, administered nasally immediately after the birth of a human to the infant.

In still other embodiments, preferably the helminthic parasite or portion thereof is selected from the group consisting of *S. mansoni, H. polygyrus, T. spiralis, T. trichiura* and *N. americanus*. The biologically active portion of the helminthic parasite may be selected from the group consisting of parasite extract, parasite eggs, parasite egg extract, parasite larvae, parasite larvae extract, parasite cercariae and parasite cercariae extract.

Yet other embodiments are directed to a method of treating an autism spectrum disorder in a human patient comprising administering to a human patient in need thereof a therapeutically effective amount of a pharmaceutical formulation comprising an effective amount of a bacterial formulation that comprises: *Prevotella; Lactobacillus johnsonii; Bacteroides fragilis, Lactobacillus ruminus,* and at least one of *B. longum* bv. *Infantis* isolate UCD272 or *B. longum* bv. *Infantis,* AY151398; and an effective amount of an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis.*

Yet another embodiment is directed to a method of treating psoriasis in a human patient comprising administering to a human patient in need thereof a therapeutically effective amount of a pharmaceutical formulation comprising an effective amount of a bacterial formulation that comprises: *Prevotella; Lactobacillus johnsonii; Bacteroides fragilis, Lactobacillus ruminus,* and at least one of *B. longum* bv. *Infantis* isolate UCD272 or *B. longum* bv. *Infantis,* AY151398; and an effective amount of an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis.*

In another embodiment, an antibody of IgE, or fragment thereof, is added to compositions of the present invention. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Thus, the Th2 immune response, culminating in eosinophilia and IgE production, is not only characteristic of allergy but also of infection by parasitic worms (helminths). Some contend that that IgE and its receptors evolved to help counter metazoan parasites. Allergens (IgE-antigens) are present in only a small minority of protein families and known IgE targets in helminths belong to these same families (e.g., EF-hand proteins, tropomyosin, and PR-1 proteins). During various helminth infections the Th2 response is moderated by parasite-expressed molecules.

It is believed that the IgE axis evolved to protect mammals against multi-cellular parasites, and allergies are yet another IgE-mediated phenomena. The parallels between allergy and the immune response to helminthes include, unlike most other inflammatory/infectious conditions, induction of strongly Th2-skewed responses associated with cytokines such as IL-4, IL-5, and IL-13. IgE, while a normally rare, tightly controlled antibody isotype is greatly elevated in helminth infection. It is thought that IgE, its receptors and distinctive cellular responses did not evolve to target harmless molecules occurring in plant pollen, dust-mites, or animal dander, but rather, evolved to counter parasites that were too large to be phagocytosed, and/or evolved to counter venoms, and that allergy is a misdirected anti-parasite response in hypersensitive people. It is believed that all known allergens have equivalents (of widely varying structure) in metazoan parasites.

Levels of anti-parasite IgE have been correlated with resistance to infection and helminths are powerful inducers of an IgE response. It is further believed that the global increase in allergy especially in urban areas, can be correlated with the decline in helminth infections. One aspect of the present invention is directed to the fact that environmental allergens are related to helminth counterparts and that the IgE response against such allergens is associated with host protection.

Very few protein families contain allergens and the molecules targeted by IgE in helminths are in these known allergen families. Nearly all families of allergens in animals, plants, or fungi have corresponding allergens in helminths. The muscle protein tropomyosin is an important IgE target in a number of nematode infections. Tropomyosin is highly conserved across many invertebrates and is responsible for much of the IgE cross-reactivity between Ascaris and dust-mites. Cockroach tropomyosin is a major allergen that also shows strong IgE cross-reactivity with the highly similar Ascaris molecule andt tropomyosin from filarial nematodes is recognized by IgE against dust-mite tropomyosin. While dust-mites are not metazoan parasites, they have close relatives that are (e.g., the scabies mite, Sarcoptes scabiei) and IgE response to Sarcoptes scabiei is involved in protection against repeat infestation.

Most proteins are not allergens. High thermal stability allows allergens to persist in the environment or survive cooking and digestion. Plant chitinases are contained in a multitude of plants, such as Heveine in latex, kiwi fruit, avocado and grapes, and are related to dust-mite allergens Der p 15 and Der p 18. Allergenicity is only reported in foods that are consumed uncooked, as type I chitinases are inactivated by heating.

Many helminthic parasites rely on production of proteases during tissue migration and such proteases are believed to be a factor underlying the parasites' intrinsic allergenicity. Proteins are believed to have inherent allergenicity because they have structural similarity to dominant antigens in metazoan parasites. The IgE system evolved to target Th2 responses at large multi-cellular parasites, organisms that are much more closely related to humans than bacterial, fungal, or viral pathogens. It is believed non-parasitic proteins are allergenic because of their homology with metazoan parasites. Allergenicity may largely depend upon a dissimilarity with human proteins. Moreover, most IgE epitopes are believed to be conformational (discontinuous) and are not identified by a primary sequence comparison. As helminths often have complex life-cycles, the expression profile of allergen-like molecules influences the host response. Thus, different stages of helminth development relates to exposure and development of an immune response due to distinct molecules produced at the various stages involved. Anti-protein IgE responses and host defense are two sides of the same coin. The link between the presence of parasite-specific IgE and resistance to infection is supported by epidemiological and experimental evidence, despite the detailed molecular basis underlying such resistance remaining less understood. One aspect to the present invention is directed to the purposeful activation of basophils, mast cells, and other IgE-bearing effect or cells to achieve protection. The activation of mast cells and eosinophils result in the release of proteases and toxic proteins shown to directly kill larval stages of parasites. Thus, one aspect of the present invention is directed to the IgE-dependent activation of basophils to release highly toxic polypeptides to kill parasites.

Another aspect of the present invention is directed to the treatment of expectant mothers with the compositions and formulations as described herein to trigger an appropriate response from individual women's immune systems such that autoimmune disease does not occur. Autoimmune diseases affect women 75 percent more often than men. It is believed that estrogen tends to increase autoimmune responses and during pregnancy the variations of hormones appears to trigger some autoimmune diseases. Thus, effective administration of the compositions and formulations of the present invention can preclude the development of such autoimmune diseases in pregnant women.

Parasitic helminths represent an extreme in the spectrum of pathogens, as large multicellular animals derived from free-living metazoan ancestors. Although commonly grouped together, the helminths in fact comprise two very distantly related taxa that diverged 600 million or more years ago, i.e., the roundworm nematodes and the flatworm plathelminths. Between these two main groups of distantly related helminth parasites, individual species of parasites have evolved to occupy a diverse range of niches within their hosts, using a wide range of infection strategies, yet with few exceptions the mammalian host responds to these diverse groups of organisms in a remarkably consistent and even stereotypical manner. Typically, this response involves the production of the cytokines interleukin-4 (IL-4), IL-5, IL-10, and IL-13, as well as immunoglobulin E (IgE) and the expansion and mobilization of specific effector cells, such as mast cells, eosinophils, and basophils. Collectively, this group of responses resembles the T-helper 2 (Th2) immune response. Th2 responses may serve the host by limiting the degree of helminthic organization. Genetically susceptible persons who are never exposed to helminths may lack a strong Th2 immune response and develop a poorly regulated and destructive intestinal Th1 response, leading to chronic colitis or ileitis.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other structures, methods and systems for carrying out the several purposes of the present invention to instruct and encourage the exposure of expectant mothers to allergens such that the number of T cells in the cord blood that feeds her unborn child is significantly above the number of T cells present in expectant mothers who had not been exposed to the allergens present in the manure-containing soil as described herein, thus lessening the occurrence of allergies of newborn babies. It is important, therefore, that the claims be regarded as including any such equivalent construction insofar as they do not depart from the spirit and scope of the present invention.

What is claimed is:

1. A method of reducing a likelihood of an allergic disease developing, comprising: dispersing, in the air of an urban dwelling where an expectant mother human female resides, a prophylactic immune stimulating composition comprising: at least 5 grams of bovine manure components from a bovine that has not been administered an antibiotic effective against one of *Lactobacillus johnsonii,* and *Bifidobacterium longum* bv. *Infantis,* and an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis*, wherein said step of dispersing includes exposing the expectant mother to said immune stimulating composition so that the expectant mother can inhale the immune stimulating composition laden air within the urban dwelling at least three times a week for at least a 5 minute time period, for at least the expectant mother's last trimester, and applying to the expectant mother's birth canal prior to the birth of her baby with a composition including a bacterial formulation that comprises at least one of: *Prevotella; Lactobacillus johnsonii; Bacteroides fragilis, Lactobacillus ruminus, Bifidobacterium longum* bv. *Infantis,* and an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis.*

2. The method of claim 1, wherein the immune stimulating composition is enhanced by the addition of at least one of the following: *L. infantitis, L. johnsonii,* and helminthes.

3. The method of claim 1, wherein the composition comprises an extract derived from at least two of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis.*

4. The method according to claim 1, further comprising providing an air flow device adapted to convey air about said bovine manure components and the urban dwelling.

5. The method according to claim 1, wherein said bovine manure components include at least one bacteroidetes selected from a phylum of bacteria of the group *Bacteroides, Flavobacteria,* and *Sphingobacteria,* and at least one gram-positive firmicute.

6. The method according to claim 1, wherein said immune stimulating composition further comprises at least 1000 bacteria selected from the group of *Bifidobacterium longum biovar infantis,* and *Lactobacillus johnsonii.*

7. The method according to claim 1, wherein said immune stimulating composition further comprises at least 1 gram of a helminthes extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus, Trichinella spiralis* and *Trichuris suis ova.*

8. The method according to claim 1, wherein the immune stimulating composition further includes a separate additive including at least one arabinogalactan.

9. The method according to claim 1, wherein the immune stimulating composition further includes cyclodextrin.

10. The method according to claim 1, wherein the immune stimulating composition includes *Lactococcus lactis.*

11. The method according to claim 1, wherein the immune stimulating composition includes *Lactococcus Latis* and at least one arabinogalactan.

12. A method of reducing a likelihood of an allergic disease developing, comprising: dispersing, in the air of an urban dwelling where an expectant mother human female resides, a prophylactic immune stimulating composition comprising: at least 5 grams of bovine manure components from a bovine that has not been administered an antibiotic effective against one of *Lactobacillus johnsonii,* and *Bifidobacterium longum bv. Infantis,* and an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis*, wherein said step of dispersing includes exposing the expectant mother to said immune stimulating composition so that the expectant mother can inhale the immune stimulating composition laden air within the urban dwelling at least three times a week for at least a 5 minute time period, for at least the expectant mother's last trimester, and applying to the expectant mother's birth canal prior to the birth of her baby with a composition including a bacterial formulation that comprises at least one of: *Prevotella; Lactobacillus johnsonii; Bacteroides fragilis, Lactobacillus ruminus, Bifidobacterium longum bv. Infantis.*

13. The method according to claim 12, wherein said bovine manure components include at least one bacteroidetes selected from a phylum of bacteria of the group *Bacteroides, Flavobacteria,* and *Sphingobacteria*, and at least one gram-positive firmicute.

14. The method according to claim 12, wherein the immune stimulating composition further includes a separate additive including at least one arabinogalactan.

15. The method according to claim 12, wherein the immune stimulating composition further includes cyclodextrin.

16. The method according to claim 12, wherein the immune stimulating composition includes *Lactococcus lactis.*

17. A method of reducing a likelihood of an allergic disease developing, comprising: dispersing, in the air of an urban dwelling where an expectant mother human female resides, a prophylactic immune stimulating composition comprising: at least 5 grams of bovine manure components from a bovine that has not been administered an antibiotic effective against one of *Lactobacillus johnsonii,* and *Bifidobacterium longum bv. Infantis,* and an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis*, wherein said step of dispersing includes exposing the expectant mother to said immune stimulating composition so that the expectant mother can inhale the immune stimulating composition laden air within the urban dwelling at least three times a week for at least a 5 minute time period, for at least the expectant mother's last trimester, and applying to the expectant mother's birth canal prior to the birth of her baby with a composition including an extract derived from a helminth selected from the group consisting of: *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis.*

18. The method according to claim 17, wherein the immune stimulating composition further includes a separate additive including at least one arabinogalactan.

19. The method according to claim 17, wherein the immune stimulating composition further includes cyclodextrin.

20. The method according to claim 17, wherein the immune stimulating composition includes *Lactococcus lactis.*

21. The method according to claim 1, wherein the immune stimulating composition includes *Clostridium clostridioforme.*

22. The method according to claim 1, wherein the allergic disease comprises one of asthma and food allergies.

23. The method according to claim 12, wherein the immune stimulating composition includes *Clostridium clostridioforme.*

24. The method according to claim 12, wherein the allergic disease comprises one of asthma and food allergies.

25. The method according to claim 17, wherein the immune stimulating composition includes *Clostridium clostridioforme.*

26. The method according to claim 17, wherein the allergic disease comprises one of asthma and food allergies.

\* \* \* \* \*